US008512711B2

(12) United States Patent
Lua et al.

(10) Patent No.: US 8,512,711 B2
(45) Date of Patent: Aug. 20, 2013

(54) VLP BASED VACCINE DELIVERY SYSTEM

(75) Inventors: Linda Hwee-Lin Lua, South Brisbane (AU); Anton Peter Jacob Middelberg, Brookfield (AU)

(73) Assignee: The University of Queensland (AU)

( * ) Notice: Subject to any disclaimer, the term of this patent is extended or adjusted under 35 U.S.C. 154(b) by 804 days.

(21) Appl. No.: 12/444,092

(22) PCT Filed: Oct. 4, 2007

(86) PCT No.: PCT/AU2007/001478
§ 371 (c)(1),
(2), (4) Date: Oct. 2, 2009

(87) PCT Pub. No.: WO2008/040060
PCT Pub. Date: Apr. 10, 2008

(65) Prior Publication Data
US 2010/0028375 A1 Feb. 4, 2010

(30) Foreign Application Priority Data
Oct. 4, 2006 (AU) ................. 2006905475

(51) Int. Cl.
*A61K 39/12* (2006.01)
*A61K 39/145* (2006.01)
*A61K 39/295* (2006.01)
*C12Q 1/70* (2006.01)

(52) U.S. Cl.
USPC ............... 424/204.1; 424/202.1; 424/206.1; 435/5

(58) Field of Classification Search
None
See application file for complete search history.

(56) References Cited

U.S. PATENT DOCUMENTS
4,703,004 A  10/1987  Hopp et al.

FOREIGN PATENT DOCUMENTS
WO   WO 2006/108658 A2   10/2006

OTHER PUBLICATIONS

Galarza et al. Virus-Like Particle (VLP) Vaccine Conferred Complete Protection against a Letha Influenza Virus Challenge. Viral Immunology 2005, vol. 18, No. 1, pp. 244-251.*
Van Borm et al. Highly Pathogenic H5N1 Influenza Virus in Smuggled Thai Eagles, Belgium. Emerging Infectious Diseases 2005, vol. 11, No. 5, pp. 702-705.*
Bulavaite, A., et al., "Construction of Recombinant Chimeric Proteins on the Basis of SV40 Virus Major Coat Protein VP1," *Biologija*, 2002, pp. 10-12, vol. 3.
Gleiter, S., et al., "Changing the Surface of a Virus Shell Fusion of an Enzyme to Polyoma VP1," *Protein Science*, 1999, pp. 2562-2569, vol. 8.
Neirynck, S., et al, "A Universal Influenza A Vaccine Based on the Extracellular Domain of the M2 Protein," *Nature Medicine*, 1999, pp. 1157-1163, vol. 5(10).
Palucha, A., et al., "Virus-Like Particles: Models for Assembly Studies and Foreign Epitope Carriers," *Progress in Nucleic Acid Research and Molecular Biology*, 2005, pp. 135-168, vol. 80.
Stubenrauch, K., et al., "Purification of a Viral Coat Protein by an Engineered Polyionic Sequence," *Journal of Chromatography B*, 2000, pp. 77-84, vol. 737.
Gedvilaite, A., et al., "Formation of Immunogenic Virus-Like Particles by Inserting Epitopes into Surface-Exposed Regions of Hamster Polyomavirus Major Capsid Protein," *Virology*, 2000, pp. 21-35, vol. 273.
Gedvilaite, A., et al., "Segments of Puumala Hantavirus Nucleocapsid Protein Inserted into Chimeric Polyomavirus-Derived Virus-Like Particles Induce a Strong Immune Response in Mice," *Viral Immunology*, 2004, pp. 51-68, vol. 17(1).
Neugebauer, M., et al., "Development of a Vaccine Marker Technology: Display of B Cell Epitopes on the Surface of Recombinant Polyomavirus-Like Pentamers and Capsoids Induces Peptide-Specific Antibodies in Piglets After Vaccination," *Biotechnology Journal*, 2006, pp. 1435-1446, vol. 1(12).
Shin, Y.C., and W.R. Folk, "Formation of Polyomavirus-Like Particles with Different VP1 Molecules That Bind the Urokinase Plasminogen Activator Receptor," *Journal of Virology*, 2003, pp. 11491-11498, vol. 77(21).
Zvirbliene, A., et al., "Generation of Monoclonal Antibodies of Desired Specificity Using Chimeric Polyomavirus-Derived Virus-Like Particles," *Journal of Immunological Methods*, 2006, pp. 57-70, vol. 311(1-2).
Aleksaite, E., and A. Gedvilaite, "Generation of Chimeric Hamster Polyomavirus VP1 Virus-Like Particles Harboring Three Tumor-Associated Antigens," *Biologija*, 2006, pp. 83-87, vol. 3.
Gleiter, S., and H. Lilie, "Coupling of Antibodies Via Protein Z on Modified Polyoma Virus-Like Particles," *Protein Science*, 2001, pp. 434-444, vol. 10(2).
Siray, H., et al., "An Immunodominant, Cross-Reactive B-Cell Epitope Region is Located at the C-Terminal Part of the Hamster Polyomavirus Major Capsid Protein VP1," *Viral Immunology*, 2000, pp. 533-545, vol. 13(4).
Stubenrauch, K., et al., "Conjugation of an Antibody Fv Fragment to a Virus Coat Protein: Cell-Specific Targeting of Recombinant Polyoma-Virus-Like Particles," *The Biochemical Journal*, 2001, pp. 867-873, vol. 356(3).
Hopp, T.P., et al., "A Short Polypeptide Marker Sequence Useful for Recombinant Protein Identification and Purification," *Nature*, 1998, pp. 1204-1210, vol. 6.

\* cited by examiner

*Primary Examiner* — Louise Humphrey
(74) *Attorney, Agent, or Firm* — Alston & Bird LLP

(57) ABSTRACT

An isolated protein comprising a VP1 amino acid sequence wherein one or more exposed loops within said VP1 has an insertion of an amino acid sequence from a virus protein other than VP1, and encoding nucleic acid, are provided. Typically, the virus protein other than VP1 is derived from an influenza virus and in particular, avian influenza virus. The isolated protein may have an insertion of amino acid sequence from a single protein or a plurality of proteins. Also provided are expression constructs, VLPs, pharmaceutical compositions, vaccines and methods of treatment that may be useful in the prophylactic and/or therapeutic treatment of any disease of viral origin, and in particular, influenza virus.

52 Claims, 27 Drawing Sheets

```
VP1            1  MAPKRKSGVSKCETKCTKACPRPAPVPKLLIKGGMEVLDLVTGPDSVTEIEAFLNPRMGQ  60
VP1-S1         1  MAPKRKSGVSKCETKCTKACPRPAPVPKLLIKGGMEVLDLVTGPDSVTEIEAELNPRMGQ  60
VP1-S4         1  MAPKRKSGVSKCETKCTKACPRPAPVPKLLIKGGMEVLDLVTGPDSVTEIEAFLNPRMGQ  60
VP1-S3         1  MAPKRKSGVSKCETKCTKACPRPAPVPKLLIKGGMEVLDLVTGPDSVTEIEAFLNPRMGQ  60
VP1-S1-S3-S4   1  MAPKRKSGVSKCETKCTKACPRPAPVPKLLIKGGMEVLDLVTGPDSVTEIEAFLNPRMGQ  60
                  ************************************************** ********

VP1           61  PPTPESLTEGGQYYGWSRGINLATSD-TEDSPGNNTLPTWSMAKLQLPMLNEDLTCDTLQ 119
VP1-S1        61  PPTPESLTEGGQYYGWSRGINLATSAGTEDSPGNNTLPTWSMAKLQLPMLNEDLTCDTLQ 120
VP1-S4        61  PPTPESLTEGGQYYGWSRGINLATSD-TEDSPGNNTLPTWSMAKLQLPMLNEDLTCDTLQ 119
VP1-S3        61  PPTPESLTEGGQYYGWSRGINLATSD-TEDSPGNNTLPTWSMAKLQLPMLNEDLTCDTLQ 119
VP1-S1-S3-S4  61  PPTPESLTEGGQYYGWSRGINLATSAGTEDSPGNNTLPTWSMAKLQLPMLNEDLTCDTLQ 120
                  *************************  ********************************

VP1          120  MWEAVSVKTEVVGSGSLLDVHGFNKPTDTVNTKGISTPVEGSQYHVFAVGGEPLDLQGLV 179
VP1-S1       121  MWEAVSVKTEVVGSGSLLDVHGFNKPTDTVNTKGISTPVEGSQYHVFAVGGEPLDLQGLV 180
VP1-S4       120  MWEAVSVKTEVVGSGSLLDVHGFNKPTDTVNTKGISTPVEGSQYHVFAVGGEPLDLQGLV 179
VP1-S3       120  MWEAVSVKTEVVGSGSLLDVHGFNKPTDTVNTKGISTPVEGSQYHVFAVGGEPLDLQGLV 179
VP1-S1-S3-S4 121  MWEAVSVKTEVVGSGSLLDVHGFNKPTDTVNTKGISTPVEGSQYHVFAVGGEPLDLQGLV 180
                  ************************************************************

VP1          180  TDARTKYKEEGVVTIKTITKKDMVNKDQVLNPISKAKLDKDGMYPVEIWHPDPAKNENTR 239
VP1-S1       181  TDARTKYKEEGVVTIKTITKKDMVNKDQVLNPISKAKLDKDGMYPVEIWHPDPAKNENTR 240
VP1-S4       180  TDARTKYKEEGVVTIKTITKKDMVNKDQVLNPISKAKLDKDGMYPVEIWHPDPAKNENTR 239
VP1-S3       180  TDARTKYKEEGVVTIKTITKKDMVNKDQVLNPISKAKLDKDGMYPVEIWHPDPAKNENTR 239
VP1-S1-S3-S4 181  TDARTKYKEEGVVTIKTITKKDMVNKDQVLNPISKAKLDKDGMYPVEIWHPDPAKNENTR 240
                  ************************************************************

VP1          240  YFGNYTGGTT-TPPVLQFTNTLTTVLLDENGVGPLCKGEGLYLSCVDIMGWRVTR-NYDV 297
VP1-S1       241  YFGNYTGGTT-TPPVLQFTNTLTTVLLDENGVGPLCKGEGLYLSCVDIMGWRVTRSAYDV 298
VP1-S4       240  YFGNYTGGTHVTPPVLQFTNTLTTVLLDENGVGPLCKGEGLYLSCVDIMGWRVTR-NYDV 298
VP1-S3       240  YFGNYTGGTT-TPPVLQFTNTLTTVLLDENGVGPLCKGEGLYLSCVDIMGWRVTR-NYDV 297
VP1-S1-S3-S4 241  YFGNYTGGTHVTPPVLQFTNTLTTVLLDENGVGPLCKGEGLYLSCVDIMGWRVTRSAYDV 300
                  *********  ****************************************** ***

VP1          298  HHWRGLPRYFKITLRKRWVKNPYPMASLISSLFNNMLPQVQGQPMEGENTQVEEVRVYDG 357
VP1-S1       299  HHWRGLPRYFKITLRKRWVKNPYPMASLISSLFNNMLPQVQGQPMEGENTQVEEVRVYDG 358
VP1-S4       299  HHWRGLPRYFKITLRKRWVKNPYPMASLISSLFNNMLPQVQGQPMEGENTQVEEVRVYDG 358
VP1-S3       299  HHWRGLPRYFKITLRKRWVKNPYPMASLISSLFNNMLPQVQGQPMEGENTQVEEVRVYDG 358
VP1-S1-S3-S4 301  HHWRGLPRYFKITLRKRWVKNPYPMASLISSLFNNMLPQVQGQPMEGENTQVEEVRVYDG 360
                  ************************************************************

VP1          358  TEPVPGDPDMTRYVDRFGKTKTVFPGN 384
VP1-S1       359  TEPVPGDPDMTRYVDRFGKTKTVFPGN 385
VP1-S4       359  TEPVPGDPDMTRYVDRFGKTKTVFPGN 385
VP1-S3       359  TEPVPGDPDMTRYVDRFGKTKTVFPGN 385
VP1-S1-S3-S4 361  TEPVPGDPDMTRYVDRFGKTKTVFPGN 387
                  ***************************
```

FIGURE 1

```
VP1-S1      1  MAPKRKSGVSKCETKCTKACPRPAPVPKLLIKGGMEVLDLVTGPDSVTEIEAFLNPRMGQ   60
VP1-S1B     1  MAPKRKSGVSKCETKCTKACPRPAPVPKLLIKGGMEVLDLVTGPDSVTEIEAFLNPRMGQ   60
VP1-S1A     1  MAPKRKSGVSKCETKCTKACPRPAPVPKLLIKGGMEVLDLVTGPDSVTEIEAFLNPRMGQ   60
VP1-S1M2e   1  MAPKRKSGVSKCETKCTKACPRPAPVPKLLIKGGMEVLDLVTGPDSVTEIEAFLNPRMGQ   60
VP1-S1hM2e  1  MAPKRKSGVSKCETKCTKACPRPAPVPKLLIKGGMEVLDLVTGPDSVTEIEAFLNPRMGQ   60
               ************************************************************

VP1-S1      61 PPTPESLTEGGQYYGWSRGINLATSA----------------------GTEDSPGNNTL   97
VP1-S1B     61 PPTPESLTEGGQYYGWSRGINLATSAPNDAAEQTKL---YQ---NPTTYGTEDSPGNNTL  114
VP1-S1A     61 PPTPESLTEGGQYYGWSRGINLATSAPYNGKSS---------------GTEDSPGNNTL  104
VP1-S1M2e   61 PPTPESLTEGGQYYGWSRGINLATSASLLTEVETPTRNEWECRCSDSSDGTEDSPGNNTL  120
VP1-S1hM2e  61 PPTPESLTEGGQYYGWSRGINLATSASLLTEVETPIRNEWGCRCNDSSDGTEDSPGNNTL  120
               **************************                    ***********

VP1-S1      98  PTWSMAKLQLPMLNEDLTCDTLQMWEAVSVKTEVVGSGSLLDVHGFNKPTDTVNTKGIST 157
VP1-S1B     115 PTWSMAKLQLPMLNEDLTCDTLQMWEAVSVKTEVVGSGSLLDVHGFNKPTDTVNTKGIST 174
VP1-S1A     105 PTWSMAKLQLPMLNEDLTCDTLQMWEAVSVKTEVVGSGSLLDVHGFNKPTDTVNTKGIST 164
VP1-S1M2e   121 PTWSMAKLQLPMLNEDLTCDTLQMWEAVSVKTEVVGSGSLLDVHGFNKPTDTVNTKGIST 180
VP1-S1hM2e  121 PTWSMAKLQLPMLNEDLTCDTLQMWEAVSVKTEVVGSGSLLDVHGFNKPTDTVNTKGIST 180
                ************************************************************

VP1-S1      158 PVEGSQYHVFAVGGEPLDLQGLVTDARTKYKEEGVVTIKTITKKDMVNKDQVLNPISKAK 217
VP1-S1B     175 PVEGSQYHVFAVGGEPLDLQGLVTDARTKYKEEGVVTIKTITKKDMVNKDQVLNPISKAK 234
VP1-S1A     165 PVEGSQYHVFAVGGEPLDLQGLVTDARTKYKEEGVVTIKTITKKDMVNKDQVLNPISKAK 224
VP1-S1M2e   181 PVEGSQYHVFAVGGEPLDLQGLVTDARTKYKEEGVVTIKTITKKDMVNKDQVLNPISKAK 240
VP1-S1hM2e  181 PVEGSQYHVFAVGGEPLDLQGLVTDARTKYKEEGVVTIKTITKKDMVNKDQVLNPISKAK 240
                ************************************************************

VP1-S1      218 LDKDGMYPVEIWHPDPAKNENTRYFGNYTGGTTTPPVLQFTNTLTTVLLDENGVGPLCKG 277
VP1-S1B     235 LDKDGMYPVEIWHPDPAKNENTRYFGNYTGGTTTPPVLQFTNTLTTVLLDENGVGPLCKG 294
VP1-S1A     225 LDKDGMYPVEIWHPDPAKNENTRYFGNYTGGTTTPPVLQFTNTLTTVLLDENGVGPLCKG 284
VP1-S1M2e   241 LDKDGMYPVEIWHPDPAKNENTRYFGNYTGGTTTPPVLQFTNTLTTVLLDENGVGPLCKG 300
VP1-S1hM2e  241 LDKDGMYPVEIWHPDPAKNENTRYFGNYTGGTTTPPVLQFTNTLTTVLLDENGVGPLCKG 300
                ************************************************************

VP1-S1      278 EGLYLSCVDIMGWRVTRNYDVHHWRGLPRYFKITLRKRWVKNPYPMASLISSLFNNMLPQ 337
VP1-S1B     295 EGLYLSCVDIMGWRVTRNYDVHHWRGLPRYFKITLRKRWVKNPYPMASLISSLFNNMLPQ 354
VP1-S1A     285 EGLYLSCVDIMGWRVTRNYDVHHWRGLPRYFKITLRKRWVKNPYPMASLISSLFNNMLPQ 344
VP1-S1M2e   301 EGLYLSCVDIMGWRVTRNYDVHHWRGLPRYFKITLRKRWVKNPYPMASLISSLFNNMLPQ 360
VP1-S1hM2e  301 EGLYLSCVDIMGWRVTRNYDVHHWRGLPRYFKITLRKRWVKNPYPMASLISSLFNNMLPQ 360
                ************************************************************

VP1-S1      338 VQGQPMEGENTQVEEVRVYDGTEPVPGDPDMTRYVDRFGKTKTVFPGN 385
VP1-S1B     355 VQGQPMEGENTQVEEVRVYDGTEPVPGDPDMTRYVDRFGKTKTVFPGN 402
VP1-S1A     345 VQGQPMEGENTQVEEVRVYDGTEPVPGDPDMTRYVDRFGKTKTVFPGN 392
VP1-S1M2e   361 VQGQPMEGENTQVEEVRVYDGTEPVPGDPDMTRYVDRFGKTKTVFPGN 408
VP1-S1hM2e  361 VQGQPMEGENTQVEEVRVYDGTEPVPGDPDMTRYVDRFGKTKTVFPGN 408
                ************************************************
```

```
DQ343152  101  PANDLCYPGDFNDYEELKHLLSRINHFEKIQIIPKSSWSNHEASSGVRSACPYNGKSSFFRNVVWLIKKNSAYPTIKRSYNNTNQEDLLILMGIHHPNDA  200
DQ343151  101  PANDLCYPGDFNDYEELKHLLSRINHFEKIQIIPKSSWSNHEASSGVSSACPYLGKSSFFRNVVWLIKKNSAYPTIKRSYNNTNQEDLLVLMGIHHPNDA  200
DQ343150  101  PANGLCYPGDFNDYEELKHLLSRINMFEKIQIIPKSSWSDHGASSGVSSACSYILGKPSFFRNVVWLIKKNNTYPPIKVSYNNTNQEDLLVLMGIHHPNDE  200
DQ236672  101  PANDLCYPGNFNDYEELKHLLSRINHFEKIQIIPKSSWSDHEASSGVSSACPYQGRSSFFRNVVWLIKKDNAYPTIKRSYNNTYPTIKRSYNNTNQEDLLVLMGIHHPNDA  200
DQ236085  101  PVNDLCYPGDFNDYEELKHLLSRINHFEKIQIIPKSSWSSHEASLGVSSACPYQGKSSFFRNVVWLIKKNSTYPTIKRSYNNTYPTIKRSYNNTNQEDLLVLMGIHHPNDA  200
DQ236077  101  PVNDLCYPGDFNDYEELKHLLSRINHFEKIQIIPKSSWSSHEASLGVSSACPYQGKSSFFRNVVWLIKKNSTYPTIKRSYNNTYPTIKRSYNNTNQEDLLILMGIHHPNDA  200
DQ211925  101  PANDLCYPGDFNDYEELKHLLSRINHFEKIQIIPKSSWSNHEASSGVSSACPYNGKSSFFRNVVWLIKKNSAYPTIKRSYNNTNQEDLVLVLMGIHHPNDA  200
DQ182483  101  PVNDLCYPGDFNDYEELKHLLSRINHFEKIQIIPKSSWSSHEASLGVSSACPYQGRSFFRNVVWLIKKNSTYPTIKRSYNNTNQEDLLVLMGIHHPNDA  200
DQ023145  101  PANDLCYPGDFNDYEELKHLLSRINHFEKIQIIPKSSWSNHDASSGVSSACPYHGRSSFFRNVVWLIKKNSAYPTIKRSYNNTNQEDLLVLMGIHHPNDA  200
AY741221  101  PANDLCYPGDFNDYEELKHLLSRINHFEKIQIIPKSSWSDHEASSGVSSACPYQGSPSFFRNVVWLIKKNSTYPTIKRSYNNTNPEDLLVLMGIHHPNDA  200
AY741219  101  PANDLCYPGDFNDYEELKHLLSRINHFEKIRIIPKSSWSNHDASSGVSSACPYLGKPSFFRNVVWLIKKNSTYPTIKRGYNNTPEDLLVLMGIHHPNDA  200
AY741217  101  PANDLCYPGDFNDYEELKHLLSRINHFEKIQIIPKSSWSDHEASSGVSSACPYLGKPSFFRNVVWLIKKNSTYPTIKRGYNNTYPTIKRSYNNTNQADLLVLMGIHHPNDA  200
AY741215  101  PANDLCYPGDFNDYEELKHLLSRINHFEKIQIIPKSSWSDHEASSGVSSACPYQGNPSFFRNVVWLIKKSAYPTIKRSYNNTYPTIKRSYNNTNQEDLLVLMGIHHPNDA  200
AY741213  101  PANDLCYPGDFNDYEELKHLLSRINHFEKIQIIPKSSWSSHEASLGVSSACPYQGKSSFFRNVVWLIKKNSTYPTIKRSYNNTYPTIKRSYNNTNQEDLLVLMGIHHPNDA  200
AY646175  101  PVNDLCYPGDFNDYEELKHLLSRINHFEKIQIIPKSSWSSHEASLGVSSACPYQGKSSFFRNVVWLIKKNSTYPTIKRSYNNTNQEDLLVLMGIHHPNDA  200
AY646167  101  PVNDLCYPGDFNDYEELKHLLSRINHFEKIQIIPKSSWSSHEASLGVSSACPYQGKSSFFRNVVWLIKKNSTYPTIKRSYNNTNQEDLLVLMGIHHPNDA  200

AY555153  101  PVNDLCYPGDFNDYEELKHLLSRINHFEKIQIIPKSSWSSHEVSLGVSSACPYQGKSSFFRNVVWLIKKNSTYPTIKRSYNNTNQEDLLVLMGIHHPNDA  200
AB239125  101  PVNDLCYPGDFNDYEELKHLLSRINHFEKIQIIPKSSWLSHEASLGVSSACPYQGKSSFFRNVVWLIKKDNAYPTIKRSYNNTYPTIKRSYNNTNQEDLLVLMGIHHPNDA  200
AB233322  101  PANDLCYPGDFNDYEELKHLLSRINHFEKIQIIPKSSWSDHEASSGVSSACPYQGRSSFFRNVVWLIKKDNAYPTIKRSYNNTYPTIKRSYNNTNQEDLLVLMGIHHPNDA  200
AB233321  101  PANDLCYPGNFNDYEELKHLLSRINHFEKIQIIPKSSWSDHEASSGVSSACPYQGRSSFFRNVVWLIKKDNAYPTIKRSYNNTYPTIKRSYNNTNQEDLLVLMGIHHPNDA  200
AB233320  101  PANDLCYPGNFNDYEELKHLLSRINHFEKIQIIPKSSWSDHEASSGVSSACPYQGRSSFFRNVVWLIKKDNAYPTIKRSYNNTYPTIKRSYNNTNQEDLLVLMGIHHPNDA  200
AB233319  101  PANDLCYPGNFNDYEELKHLLSRINHFEKIQIIPKSSWSDHEASSGVSSACPYQGRSSFFRNVVWLIKKDNAYPTIKRSYNNTNQEDLLVLMGIHHPNDA  200
AB212649  101  PSNDLCYPGNFNDYEELKHLLSRINHFEKIQIIPKSSWSDHEASSGVSSACPYQGRSSFFRNVVWLITKNSAYPTIKNSYNNTNQEDLLVLMGIHHPNDA  200
```

FIGURE 12 (2 OF 5)

| | | |
|---|---|---|
| DQ343152 | 201 | AEQTKLYQNPITYI SVGTSTLNQRLVPKIATRSKVNGQSGRMEFFWTILKPNDAINFESNGNFIAPEYAYKIVKKGDSAIMKSELEYGNCNTKCQTPMGA 300 |
| DQ343151 | 201 | AEQIKLYQNPTTYI SVGTSTLNQRLVPKIATRSKVNGQSGRMEFFWTILKPNDAINFESNGNFIAPEYAYKIVKKGDSAIMKSELEYGNCNTKCQTPMGA 300 |
| DQ343150 | 201 | AEQIKIYQNPTTYI SVGTSTLNQRLVPKIATRSKVNGQSGRMEFFWTILKPNDAINFDSNGNFIAPEYAYKIVKKGDSAIMKSELEYGNCNTKCQTPMGA 300 |
| DQ323672 | 201 | AEQTRLYQNPTTYI SVGTSTLNQRLVPKIATRSKVNGQSGRMEFFWTILKPNDAINFDSNGNFIAPENAYKIVKKGDSTIMKSELEYGNCNTKCQTPIGA 300 |
| DQ236085 | 201 | AEQTRLYQNPTTYI SVGTSTLNQRLVPKIATRSKVNGQSGRMEFFWTILKPNDAINFESNGNFIAPENAYKIVKKGDSTIMKSELEYGNCNTKCQTPIGA 300 |
| DQ236077 | 201 | AEQTKLYQNPTTYI SVGTSTLNQRLVPKIATRSKVNGQSGRMEFFWTILKPNDAINFESNGNFIAPEYAYKIVKKGDSTIMKSELEYGNCNTKCQTPMGA 300 |
| DQ211925 | 201 | AEQTRLYQNPTTYI SVGTSTLNQRLVPRIATRSKVNGQSGRMEFFWTILKPNDAINFESNGNFIAPEYAYKIVKKGDSAIMKSELEYGNCNTKCQTPMGA 300 |
| DQ182483 | 201 | AEQTKLYQNPTTYI SVGTSTLNQRLVPEIATRPKVNGQSGRMEFFWTILKPNDAINFESNGNFIAPEYAYKIVKKGDSTIMKSELEYGNCNTKCQTPMGA 300 |
| DQ023145 | 201 | AEQTKLYQNPTTYI SVGTSTLNQRLVPKIATRSKVNGQSGRMEFFWTILKPNDAINFESNGNFIAPEYAYKIVKKGDSAIMKSELEYGNCNTKCQTPMGA 300 |
| AY741221 | 201 | AEQIKLYQNPTTYI SVGTSTLNQRLVPKIATRSKVNGQSGRMEFFWTILKPNDAINFESNGNFIAPEYAYKIVKKGDSAIMKSELEYGNCNTKCQTPMGA 300 |
| AY741219 | 201 | AEQIKLYQNPTTYI SVGTSTLNQRLVPKIATRSKVNGQSGRMEFFWTILKPNDAINFESNGNFIAPEYAYKIVKKGDSAIMKSELEYGNCNTKCQTPVGA 300 |
| AY741217 | 201 | AEQIKLYQNPTTYI SVGTSTLNQRLVPKIATRSKVNGQSGRMEFFWTILKPNDAINFESNGNFIAPEYAYQIVKKGDSAIMKSELEYGNCNTKCQTPMGA 300 |
| AY741215 | 201 | AEQIKLYQNPTTYI SVGTSTLNQRLVPKIATRSKVNGQSGRMEFFWTILKPNDAINFESNGNFIAPEYAYKIVKKGDSAIMKSELEYGNCNTKCQTPMGA 300 |
| AY741213 | 201 | AEQTKLYQNPTTYI SVGTSTLNQRLVPRIATRSKVNGQSGRMEFFWTILKPNDAINFESNGNFIAPEYAYKIVKKGDSAIMKSELEYGNCNTKCQTPMGA 300 |
| AY646175 | 201 | AEQTKLYQNPTTYI SVGTSTLNQRLVPRIATRSKVNGQSGRMEFFWTILKPNDAINFESNGNFIAPEYAYKIVKKGDSAIMKSELEYGNCNTKCQTPMGA 300 |
| AY646167 | 201 | AEQTKLYQNPTTYI SVGTSTLNQRLVPRIATRSKVNGQSGRMEFFWTILKPNDAINFESNGNFIAPEYAYKIVKKGDSAIMKSELEYGNCNTKCQTPMGA 300 |
| AY555153 | 201 | AEQTRLYQNPTTYI SVGTSTLNQRLVPKIATRSKVNGQSGRMEFFWTILKPNDAINFESNGNFIAPEYAYKIVKKGDSTIMKSELEYGNCNTKCQTPMGA 300 |
| AB239125 | 201 | AEQTRLYQNPTTYI SVGTSTLNQRLVPKIATRSKVNGQSGRMEFFWTILKPNDAINFESNGNFIAPENAYKIVKKGDSTIMKSELEYGNCNTKCQTPIGA 300 |
| AB233322 | 201 | AEQTRLYQNPTTYI SVGTSTLNQRLVPKIATRSKVNGQSGRMEFFWTILKPNDAINFESNGNFIAPENAYKIVKKGDSTIMKSELEYGNCNTKCQTPIGA 300 |
| AB233321 | 201 | AEQTRLYQNPTTYI SVGTSTLNQRLVPKIATRSKINGQSGRMEFFWTILKPNDAINFESNGNFIAPEYAYKIVKKGDSTIMKSELEYGNCNTKCQTPIGA 300 |
| AB233320 | 201 | AEQTRLYQNPTTYI SVGTSTLNQRLVPKIATRSKVNGQSGRMEFFWTILKPNDAINFESNGNFIAPENAYKIVKKGDSTIMKSELEYGNCNTKCQTPIGA 300 |
| AB233319 | 201 | AEQTRLYQNPTTYI SVGTSTLNQRLVPKIATRSKVNGQSGRMEFFWTILKPNDAINFESNGNFIAPENAYKIVKKGDSTIMKSELEYGNCNTKCQTPIGA 300 |
| AB212649 | 201 | AEQTRLYQNPTTYI SVGTSTLNQRLVPKIATRSKVNGQSGRMEFFWTILKPNDAISFESNGNFIAPEYAYKIVKKGDSAIMKSELEYGNCNTKCQTPMGA 300 |

| | | | |
|---|---|---|---|
| DQ343152 | 501 | GTYDYPRYSEEARLNREEISGVKLESMGTYQILSIYSTVASSLALAIMVAGLSLWMCSNGSLQCRICI | 568 |
| DQ343151 | 501 | GTYDYPQYSEEARLNREEISGVKLESMGTYQILSIYSTVVSSLALAIMVAGLSLWMCSNGSLQCRICI | 568 |
| DQ343150 | 501 | GTYDYPQYSEEARLNREEISGVKLESGTYQILSIYSTVASSLALAIMVAGLSLWMCSNGSLQCRICI | 568 |
| DQ323672 | 501 | GTYDYPQYSEEARLKREEISGVKLESIGTYQILSIYSTVASSLALAIMVAGLSLWMCSNGSLQCRICI | 568 |
| DQ236085 | 501 | GTYDYPQYSEEARLNREEISGVKLESIGIYQILSIYSTVASSLALAIMVAGLSLWMCSNGSLQCRICI | 568 |
| DQ236077 | 501 | GTYDYPQYSEEARLKREEISGVKLESIGIYQILSIYSTVASSLALAIMVAGLSLWMCSNGSLQCRICI | 568 |
| DQ211925 | 501 | GTYDYPRYSEEARLNREEISGVKLESIGTYQILSIYSTVASSLALAIMVAGLSLWMCSNGSLQCRICI | 568 |
| DQ182483 | 501 | GTYDYPQYSEEARLKREEISGVKLESIGTYQILSIYSTVASSLALAIMVAGLSLWMCSNGSLQCRICI | 568 |
| DQ023145 | 501 | GTYDYPQYSEEARLNREEISGVKLESIGTYQILSIYSTVASSLALAIMVAGLSLWMCSNGSLQCRICI | 568 |
| AY741221 | 501 | GTYDYPQYSEEARLNREEISGVKLESIGTYQILSIYSTVVSSLALAIMVAGLSLWMCSNGSLQCRICI | 568 |
| AY741219 | 501 | GTYDYPQYTEEARLNREEISGVKLESIGTYQILSIYSTVVSSLALAIMVAGLSLWMCSNGSLQCRICI | 568 |
| AY741217 | 501 | GTYDYRLDSEEARLNREEISGVKLESIGTYQILSIYSTVASSLALAIMVAGLSLWMCSNGSLQCRICI | 568 |
| AY741215 | 501 | GTYDYPQYSEEARLNREEISGVKLESIGTYQILSIYSTVASSLALAIMVAGLSLWMCSNGSLQCRICI | 568 |
| AY741213 | 501 | GTYDYPQYSEEARLKREEISGVKLESIGIYQILSIYSTVASSLALAIMVAGLSLWMCSNGSLQCRICI | 568 |
| AY646175 | 501 | GTYDYPQYSEEARLKREEISGVKLESIGIYQILSIYSTVASSLALAIMVAGLSLWMCSNGSLQCRICI | 568 |
| AY646167 | 501 | GTYDYPQYSEEARLKREEISGVKLESIGIYQILSIYSTVASSLALAIMVAGLSLWMCSNGSLQCRICI | 568 |
| AY555153 | 501 | GTYDYPQYSEEARLKRGEISGVKLESIGIYQILSIYSTVASSLALAIMVAGLSLWMCSNGSLQCRICI | 568 |
| AB239125 | 500 | GTYDYPQYSEEALKREEISGVKLESIGIYQILSIYSTVASSLALAIMVAGLSLWMCSNGSLQCRICI | 567 |
| AB233322 | 501 | GTYDYPQYSEEARLKREEISGVKLESIGTYQILSIYSTVASSLALAIMVAGLSLWMCSNGSLQCRICI | 568 |
| AB233321 | 501 | GTYDYPQYSEEARLKREEISGVKLESIGTYQILSIYSTVASSLALAIMVAGLSLWMCSNGSLQCRICI | 568 |
| AB233320 | 501 | GTYDYPQYSEEARLKREEISGVKLESIGTYQILSIYSTVASSLALAIMVAGLSLWMCSNGSLQCRICI | 568 |
| AB233319 | 501 | GTYDYPQYSEEARLKREEISGVKLESIGTYQILSIYSTVASSLALAIMVAGLSLWMCSNGSLQCRICI | 568 |
| AB212649 | 500 | GTYDYPQYSEEARLKREEISGVKLESIGTYQILSIYSTVASSLALAIMVAGLSLWMCSNGSLQCRICI | 567 |
| | | *** .*.*.*.*********.********************************** | |

```
U97740    201 PSTDREQTKLYVRASGRVTVSTKRSQQTVIPNIGSRPWVRGLSSRISIYWTIVKPGDILLLINSTGNLIAPRGYFKIRTGKSSIMRSDAPIGTCSSECITP 300
P03437    201 PSTNQEQTSLYVQASGRVTVSTRRSQQTIIPNIGSRPWVRGLSSRISIYWTIVKPGDVLVINSNGNLIAPRGYFKMRTGKSSIMRSDAPIDTCISECITP 300
J02132    201 PSTNQEQTSLYVQASGRVTVSTRRSQQTIIPNIGSRPWVRGLSSRISIYWTIVKPGDVLVINSNANLIAPRGYFKMRTGKSSIMRSDAPIDTCISECITP 300
J02090    201 PSTNQEQTSLYVQASGRVTVSTRRSQQTIIPNIGSRPWVRGLSSRISIYWTIVKPGDVLVINSNGNLIAPRGYFKMRTGKSSIMRSDAPIDTCISECITP 300
DQ508929  201 PSTDQEQTSLYVQASGRVTVSTKRSQQTVIPNIGSRPWVRGLSSRISIYWTIVKPGDILVINSNGNLIAPRGYFKMRTGKSSIMRSDAPIGTCISECITP 300
DQ508865  201 PSTDSDQISIYAQASGRVTVSTKRSQQTVIPNIGSSPWRGVSSRISIYWTIVKPGDILLINSTGNLIAPRGYFKIRSGKSSIMRSDAPIGKCNSECITP 300
DQ508849  201 PXTEKEQTNLYVRASGRVTVSTKRSQQTVIPNIGSXPWVRGLSSRISIYWTIVKPGDILLINSTGNLIAPRGYFKIRTGKSSIMRSDAPIGTCSSECITP 300
DQ508833  201 PSTDREQTNLYVRASGRVTVSTKRSQQTVIPNIGSRPWVRGLSSRISIYWTIVKPGDILLINSTGNLIAPRGYFKIRTGKSSIMRSDAPIDTCISECITP 300
DQ508825  201 PSTDKEQTKLYVRASGRVTVSTKRSQQTVIPNIGSRPWVRGLSSGISIYWTIVKPGDILLINSNGNLIAPRGYFKIRTGKSSIMRSDAPIGTCSSECITP 300

AY779254  201 PSTDRDQTSLYVQASGRVTVSTKRSQQTVIPNIGFRPWVRGISSSISIYWTIVKPGDILLITSTGNLIAPRGYFKIRSGKSSIMRSDAPIDNCSECITP 300
AY779253  201 PSTDRDQTSLYVQASGRVTVSTKRSQQTVIPNIGFRPWVRGISSSISIYWTIVKPGDILLITSTGNLIAPRGYFKIRSGKSSIMRSDAPIDNCNSECITP 300
AB019356  201 PSTDSDQTSLYAQASGRVTVSTKRSQQTVIPNIGSRPWVRGVSSRISIYWTIVKPGDILLINSTGNLIAPRGYFKIRSGKSSIMRSDAPIGKCNSECITP 300
AB019354  201 PSTDSDQTSLYVQASGRVTVSTKRSQQTVIPNIGSRPWVRGISSRISIYWTIVKPGDILVINSTGNLIAPRGYFKIRNGKSSIMRSDAPIDNCSECVTP 300
AAA43099  201 PSTDQEQTSLYVQASGRVTVSTKRSQQTVIPNIGSRPWVRGLSSRISIYWTIVKPGDILVINSNGNLIAPRGYFKMRTGKSSIMRSDAPIGTCISECITP 300
               ** . *  .        ***. **  *****.*****   **** ********* ** .**.***********  *.*********** ** ****

U97740    301 NGSIPNDKPFQNVNRITYGACPRYVKQNTLKLATGMRNVPEKQTRGIFGAIAGFIENGWEGMVNGWYGFRHQNSEGTGQAADLKSTQAAIDQINGKLNRL 400
P03437    301 NGSIPNDKPFQNVNKITYGACPKYVKQNTLKLATGMRNVPEKQTRGLFGAIAGFIENGWEGMIDGWYGFRHQNSEGTGQAADLKSTQAAIDQINGKLNRV 400
J02132    301 NGSIPNDKPFQNVNKITYGACPKYVKQNTLKLATGMRNVPEKQTRGLFGAIAGFIENGWEGMIDGWYGFRHQNSEGTGQAADLKSTQAAIDQINGKLNRV 400
J02090    301 NGSIPNDKPFQNVNKITYGACPKYVKQNTLKLATRMRNVPEKQTRGLFGAIAGFIENGWEGMIDGWYGFRHQNSEGTGQAADLKSTQAAIDQINGKLNRV 400
DQ508929  301 NGSIPNDKPFQNVNKITYGACPKYVKQNTLKLATGMRNVPEKQTRGIFGAIAGFIENGWEGMIDGWYGFRHQNSEGTGQAADLKSTQAAINQINGKLNRL 400
DQ508865  301 NGSIPNDKPFQNVNRITYGACPRYVKQNTLKLATGMRNVPEKQTRGIFGAIAGFIENGWEGMVDGWYGFRHQNSEGTGQAADLKSTQAAINQINGKLNRL 400
DQ508849  301 NGSIPNDKPFQNVNRITYGACPRYVKQNTLKLATGMRNVPEKQTRGIFGAIAGFIENGWEGMVDGWYGFRHQNSEGTGQAADLKSTQAAIDQINGKLNRL 400
DQ508833  301 NGSIPNDKPFQNVNRITYGACPRYVKQNTLKLATGMRNVPEKQTRGIFGAIAGFIENGWEGMVDGWYGFRHQNSEGTGQAADLKSTQAAIDQINGKLNRL 400
DQ508825  301 NGSIPNDKPFQNVNRITYGACPRYVKQNTLKLATGMRNVPEKQTRGIFGAIAGFIENGWEGMVDGWYGFRHQNSEGTGQAADLKSTQAAIDQINGKLNRL 400
AY779254  301 NGSIPNDKPFQNVNRITYGACPRYVKQNTLKLATGMRNVPEKQTRGIFGAIAGFIENGWEGMVDGWYGFRHQNSEGTGQAADLKSTQAAINQITGKLNRV 400
AY779253  301 NGSIPNDKPFQNVNRITYGACPRYVKQNTLKLATGMRNVPEKQTRGIFGAIAGFIENGWEGMVDGWYGFRHQNSEGTGQAADLKSTQAAINQINGKLNRV 400
AB019356  301 NGSIPNDKPFQNVNRITYGACPRYVKQNTLKLATGMRNVPEKQTRGIFGAIAGFIENGWEGMVDGWYGFRHQNSEGTGQAADLKSTQAAINQINGKLNRL 400
AB019354  301 NGSIPNDKPFQNVNRITYGACPRYVKQNTLKLATGMRNVPEKQTRGLFSAIAGFIENGWEGMIDGWYGFRHQNSEGTGQPADLKSTQAAINQINGKLNRV 400
AAA43099  301 NGSIPNDKPFQNVNKITYGACPKYVKQNTLKLATGMRNVPEKQTRGIFGAIAGFIENGWEGMIDGWYGFRHQNSEGTGQAADLKSTQAAIDQINGKLNRV 400
              **************.******:************** ********:*.************** ************* *********::**.******
```

| | | | |
|---|---|---|---|
| U97740 | 401 | IEKTNEKFHQIEKEFSEVEGRIQDLEKYVEDTKIDLWSYNAELLVALENQHTIDLTDSEMNKLFEKTRKQLRENAEDMGNGCFKIYHKCDNACIGSIRNG | 500 |
| P03437 | 401 | IEKTNEKFHQIEKEFSEVEGRIQDLEKYVEDTKIDLWSYNAELLVALENQHTIDLTDSEMNKLFEKTRQLRENAEMGNGCFKIYHKCDNACIESIRNG | 500 |
| J02132 | 401 | IEKTNEKFHQIEKEFSEVEGRIQDLEKYVEDTKIDLWSYNAELLVALENQHTIDLTDSEMNKLFEKTRQLRENAEDMGNGCFKIYDKCDNACIESIRNG | 500 |
| J02090 | 401 | IEKTNEKFHQIEKEFSEVEGRIQDLEKYVEDTKIDLWSYNAELLVALENQHTIDLTDSEMNKLFEKTRQLRENAEEMGNGCFKIYHKCDNACIESIRNG | 500 |
| DQ508929 | 401 | IEKTNEKFHQIEKEFSEVEGRIQDLEKYVEDTKIDLWSYNAELLVALENQHTIDLTDSEMNKLFEKTRRQLRENAEDMGNGCFKIYHKCDNACIGSIRNG | 500 |
| DQ508865 | 401 | IEKTNEKFHQIEKEFSEVEGRIQDLEKYVEDTKIDLWSYNAELLVALENQHTIDLTDSEMNKLFEKTKKQLRENAEDMGNGCFKIYHKCDNACIGSIRNG | 500 |
| DQ508849 | 401 | IEKTNEKFHQIEKEFSEVEGRIQDLEKYVEDTKIDLWSYNAELLVALENQHTIDLTDSEMNKLFERTKKQLRENAEDMGNGCFKIYHKCDNACIGSIRNG | 500 |
| DQ508833 | 401 | IEKTNEKFHQIEKEFSEVEGRIQDLEKYVEDTKIDLWSYNAELLVALENQYTIDLTDSEMNKLFEKTRKQLRENAEDMGNGCFKIYHKCDNACIGSIRNG | 500 |
| DQ508825 | 401 | IEKTNEKFHQIEKEFSEVEGRIQDLEKYVEDTKIDLWSYNAELLVALENQHTIDLTDSEMNKLFEKTRKQLRENAEDMGNGCFKIYHKCDNACIGSIRNG | 500 |
| AY779254 | 401 | IKKTNEKFHQIEKEFSEVEGRIQDLEKYVEDTKIDLWSYNAELLVALENQHTIDLTDSEMNKLFEKTRQLRENAEDMGNGCFKIYHKCDNACIGSIRNG | 500 |
| AY779253 | 401 | IKKTNEKFHQIEKEFSEVEGRIQDLEKYVEDTKIDLWSYNAELLVALENQHTIDLTDSEMNKLFERTRKQLRENAEDMGNGCFKIYHKCDNACIGSIRNG | 500 |
| AB019356 | 401 | IEKTNEKFHQIEKEFSEVEGRIQDLEKYVEDTKIDLWSYNAELLVALENQHTIDLTDSEMNKLFERTRKQLRENAEDMGNGCFKIYHKCDNACIGSIRNG | 500 |
| AB019354 | 401 | IEKTNEKFHQIEKEFSEVEGRIQDLEKYVEDTKIDLWSYNAELLVALENQHTIDLTDSEMNKLFERTRKQLRENAEDMGNGCFKIYHKCDNACIGSIRNG | 500 |
| AAA43099 | 401 | IEKTNEKFHQIEKEFSEVEGRIQDLEKYVEDTKIDLWSYNAELLVALENQHTIDLTDSEMNKLFEKTSRQLRENAEDMGNGCFKIYHKCDNACIGSIRNG | 500 |
| | | * *********************************************.*********.*******.*** *** | |

| | | | |
|---|---|---|---|
| U97740 | 501 | TYDHDVYRDEALNNRFQIKGVELKSGYKDWILWISFAISCFLLCVVLLGFIMWACQKGNIRCNICI | 566 |
| P03437 | 501 | TYDHDVYRDEALNNRFQIKGVELKSGYKDWILWISFAISCFLLCVVLLGFIMWACQKGNIRCNICI | 566 |
| J02132 | 501 | TYDHDVYRDEALNNRFQIKGVELKSGYKDWILWISFAISCFLLCVVLLGFIMWACQRGNIRCNICI | 566 |
| J02090 | 501 | TYDHDVYRDEALNNRFQIKGVELKSGYKDWILWISFAISCFLLCVVLLGFIMWACQRGNIRCNICI | 566 |
| DQ508929 | 501 | TYDHDVYRDEALNNRFQIKGVELKSGYKDWILWISFAISCFLLCVVLLGFIMWACQKGNIRCNICI | 566 |
| DQ508865 | 501 | TYDHDVYRDEALNNRFQIKGVELKSGYKDWILWISFAISCFLLCVVLLGFIMWACQKGNIRCNICI | 566 |
| DQ508849 | 501 | TYDHDVYRDEALNNRFQIKGVELKSGYKDWILWISFAISCFLLCVVLLGFIMWACQKGNIRCNICI | 566 |
| DQ508833 | 501 | TYDHDVYRDEALNNRFQIKGVELKSGYKDWILWISFAISCFLLCVVLLGFIMWACQKGNIRCNICI | 566 |
| DQ508825 | 501 | TYDHDVYRDEALNNRFQIKGVELKSGYKDWILWISFAISCFLLCVVLLGFIMWACQKGNIRCNICI | 566 |
| AY779254 | 501 | TYDHDVYRDEALNNRFQIKGVELKSGYKDWILWISFAISCFLLCVVLLGFIMWACQKGNIRCNICI | 566 |
| AY779253 | 501 | TYDHDVYRDEALNNRFQIKGVELKSGYKDWILWISFAISCFLLCVVLLGFIMWACQKGNIRCNICI | 566 |
| AB019356 | 501 | TYDHDVYRDEALNNRFQIKGVELKSGYKDWILWISFAISCFLLCVVLLGFIMWACQKGNIRCNICI | 566 |
| AB019354 | 501 | TYNHDVYRDEALNNRFQIKGVELKSGYKDWILWISFAISCFLLCVVLLGFIMWACQKGNIRCNICI | 566 |
| AAA43099 | 501 | TYDHDVYRDEALNNRFQIKGVELKSGYKDWILWISFAISCFLLCVVLLGFIMTACQKGNIRCNICI | 566 |
| | |  **************************************************.********* | |

FIGURE 13 (3 OF 3)

| | | | |
|---|---|---|---|
| VP1-S1   |   1 | MAPKRKSGVSKCETKCTKACPRPAPVPKLLIKGGMEVLDLVTGPDSVTEI |  50 |
| VP1-S1H3A|   1 | MAPKRKSGVSKCETKCTKACPRPAPVPKLLIKGGMEVLDLVTGPDSVTEI |  50 |
| VP1-S1H3B|   1 | MAPKRKSGVSKCETKCTKACPRPAPVPKLLIKGGMEVLDLVTGPDSVTEI |  50 |
| | | ************************************************** | |
| VP1-S1   |  51 | EAFLNPRMGQPPTPESLTEGGQYYGWSRGINLATSA-------------- |  86 |
| VP1-S1H3A|  51 | EAFLNPRMGQPPTPESLTEGGQYYGWSRGINLATSAKRGP---------G |  91 |
| VP1-S1H3B|  51 | EAFLNPRMGQPPTPESLTEGGQYYGWSRGINLATSAPSTNQEQTSLYVQA | 100 |
| | | ***********************************              | |
| VP1-S1   |  87 | ---GTEDSPGNNTLPTWSMAKLQLPMLNEDLTCDTLQMWEAVSVKTEVVG | 133 |
| VP1-S1H3A|  92 | SG-GTEDSPGNNTLPTWSMAKLQLPMLNEDLTCDTLQMWEAVSVKTEVVG | 140 |
| VP1-S1H3B| 101 | SGRGTEDSPGNNTLPTWSMAKLQLPMLNEDLTCDTLQMWEAVSVKTEVVG | 150 |
| | |    ***********************************************| |
| VP1-S1   | 134 | SGSLLDVHGFNKPTDTVNTKGISTPVEGSQYHVFAVGGEPLDLQGLVTDA | 183 |
| VP1-S1H3A| 141 | SGSLLDVHGFNKPTDTVNTKGISTPVEGSQYHVFAVGGEPLDLQGLVTDA | 190 |
| VP1-S1H3B| 151 | SGSLLDVHGFNKPTDTVNTKGISTPVEGSQYHVFAVGGEPLDLQGLVTDA | 200 |
| | | ************************************************** | |
| VP1-S1   | 184 | RTKYKEEGVVTIKTITKKDMVNKDQVLNPISKAKLDKDGMYPVEIWHPDP | 233 |
| VP1-S1H3A| 191 | RTKYKEEGVVTIKTITKKDMVNKDQVLNPISKAKLDKDGMYPVEIWHPDP | 240 |
| VP1-S1H3B| 201 | RTKYKEEGVVTIKTITKKDMVNKDQVLNPISKAKLDKDGMYPVEIWHPDP | 250 |
| | | ************************************************** | |
| VP1-S1   | 234 | AKNENTRYFGNYTGGTTTPPVLQFTNTLTTVLLDENGVGPLCKGEGLYLS | 283 |
| VP1-S1H3A| 241 | AKNENTRYFGNYTGGTTTPPVLQFTNTLTTVLLDENGVGPLCKGEGLYLS | 290 |
| VP1-S1H3B| 251 | AKNENTRYFGNYTGGTTTPPVLQFTNTLTTVLLDENGVGPLCKGEGLYLS | 300 |
| | | ************************************************** | |
| VP1-S1   | 284 | CVDIMGWRVTRNYDVHHWRGLPRYFKITLRKRWVKNPYPMASLISSLFNN | 333 |
| VP1-S1H3A| 291 | CVDIMGWRVTRNYDVHHWRGLPRYFKITLRKRWVKNPYPMASLISSLFNN | 340 |
| VP1-S1H3B| 301 | CVDIMGWRVTRNYDVHHWRGLPRYFKITLRKRWVKNPYPMASLISSLFNN | 350 |
| | | ************************************************** | |
| VP1-S1   | 334 | MLPQVQGQPMEGENTQVEEVRVYDGTEPVPGDPDMTRYVDRFGKTKTVFP | 383 |
| VP1-S1H3A| 341 | MLPQVQGQPMEGENTQVEEVRVYDGTEPVPGDPDMTRYVDRFGKTKTVFP | 390 |
| VP1-S1H3B| 351 | MLPQVQGQPMEGENTQVEEVRVYDGTEPVPGDPDMTRYVDRFGKTKTVFP | 400 |
| | | ************************************************** | |
| VP1-S1   | 384 | GN | 385 |
| VP1-S1H3A| 391 | GN | 393 |
| VP1-S1H3B| 401 | GN | 403 |
| | | **   | |

FIGURE 14

```
VP1-S4       1  MAPKRKSGVSKCETKCTKACPRPAPVPKLLIKGGMEVLDLVTGPDSVTEI   50
VP1-S4H3A    1  MAPKRKSGVSKCETKCTKACPRPAPVPKLLIKGGMEVLDLVTGPDSVTEI   50
VP1-S4H3

```
VP1-S4       1 MAPKRKSGVSKCETKCTKACPRPAPVPKLLIKGGMEVLDLVTGPDSVTEI  50
VP1-S4A      1 MAPKRKSGVSKCETKCTKACPRPAPVPKLLIKGGMEVLDLVTGPDSVTEI  50
VP1-S4B      1 MAPKRKSGVSKCETKCTKACPRPAPVPKLLIKGGMEVLDLVTGPDSVTEI  50
VP1-S4hM2e   1 MAPKRKSGVSKCETKCTKACPRPAPVPKLLIKGGMEVLDLVTGPDSVTEI  50
               **************************************************

VP1-S4      51 EAFLNPRMGQPPTPESLTEGGQYYGWSRGINLATSDTEDSPGNNTLPTWS 100
VP1-S4A     51 EAFLNPRMGQPPTPESLTEGGQYYGWSRGINLATSDTEDSPGNNTLPTWS 100
VP1-S4B     51 EAFLNPRMGQPPTPESLTEGGQYYGWSRGINLATSDTEDSPGNNTLPTWS 100
VP1-S4hM2e  51 EAFLNPRMGQPPTPESLTEGGQYYGWSRGINLATSDTEDSPGNNTLPTWS 100
               **************************************************

VP1-S4     101 MAKLQLPMLNEDLTCDTLQMWEAVSVKTEVVGSGSLLDVHGFNKPTDTVN 150
VP1-S4A    101 MAKLQLPMLNEDLTCDTLQMWEAVSVKTEVVGSGSLLDVHGFNKPTDTVN 150
VP1-S4B    101 MAKLQLPMLNEDLTCDTLQMWEAVSVKTEVVGSGSLLDVHGFNKPTDTVN 150
VP1-S4hM2e 101 MAKLQLPMLNEDLTCDTLQMWEAVSVKTEVVGSGSLLDVHGFNKPTDTVN 150
               **************************************************

VP1-S4     151 TKGISTPVEGSQYHVFAVGGEPLDLQGLVTDARTKYKEEGVVTIKTITKK 200
VP1-S4A    151 TKGISTPVEGSQYHVFAVGGEPLDLQGLVTDARTKYKEEGVVTIKTITKK 200
VP1-S4B    151 TKGISTPVEGSQYHVFAVGGEPLDLQGLVTDARTKYKEEGVVTIKTITKK 200
VP1-S4hM2e 151 TKGISTPVEGSQYHVFAVGGEPLDLQGLVTDARTKYKEEGVVTIKTITKK 200
               **************************************************

VP1-S4     201 DMVNKDQVLNPISKAKLDKDGMYPVEIWHPDPAKNENTRYFGNYTGGTTT 250
VP1-S4A    201 DMVNKDQVLNPISKAKLDKDGMYPVEIWHPDPAKNENTRYFGNYTGGTTT 250
VP1-S4B    201 DMVNKDQVLNPISKAKLDKDGMYPVEIWHPDPAKNENTRYFGNYTGGTTT 250
VP1-S4hM2e 201 DMVNKDQVLNPISKAKLDKDGMYPVEIWHPDPAKNENTRYFGNYTGGTTT 250
               **************************************************

VP1-S4     251 PPVLQFTNTLTTVLLDENGVGPLCKGEGLYLSCVDIMGWRVTRS------ 294
VP1-S4A    251 PPVLQFTNTLTTVLLDENGVGPLCKGEGLYLSCVDIMGWRVTRSPYNGK- 299
VP1-S4B    251 PPVLQFTNTLTTVLLDENGVGPLCKGEGLYLSCVDIMGWRVTRSPNDAAE 300
VP1-S4hM2e 251 PPVLQFTNTLTTVLLDENGVGPLCKGEGLYLSCVDIMGWRVTRSSLLTEV 300
               *******************************************

VP1-S4     295 ----------------AYDVHHWRGLPRYFKITLRKRWVKNPYPMASLI 327
VP1-S4A    300 --------------SS-AYDVHHWRGLPRYFKITLRKRWVKNPYPMASLI 334
VP1-S4B    301 QTKLYQN------PTTYAYDVHHWRGLPRYFKITLRKRWVKNPYPMASLI 344
VP1-S4hM2e 301 ETPIRNEWGCRCNDSSDAYDVHHWRGLPRYFKITLRKRWVKNPYPMASLI 350
                                *********************************

VP1-S4     328 SSLFNNMLPQVQGQPMEGENTQVEEVRVYDGTEPVPGDPDMTRYVDRFGK 377
VP1-S4A    335 SSLFNNMLPQVQGQPMEGENTQVEEVRVYDGTEPVPGDPDMTRYVDRFGK 384
VP1-S4B    345 SSLFNNMLPQVQGQPMEGENTQVEEVRVYDGTEPVPGDPDMTRYVDRFGK 394
VP1-S4hM2e 351 SSLFNNMLPQVQGQPMEGENTQVEEVRVYDGTEPVPGDPDMTRYVDRFGK 400
               **************************************************

VP1-S4     378 TKTVFPGN 385
VP1-S4A    385 TKTVFPGN 393
VP1-S4B    395 TKTVFPGN 403
VP1-S4hM2e 401 TKTVFPGN 409
               ********
```

FIGURE 18

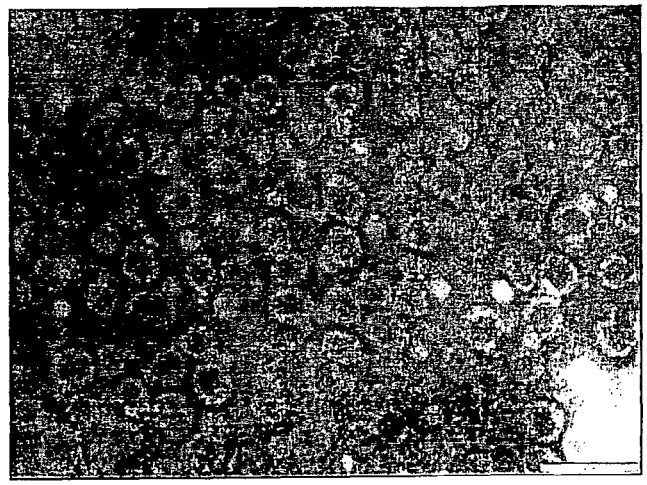
A
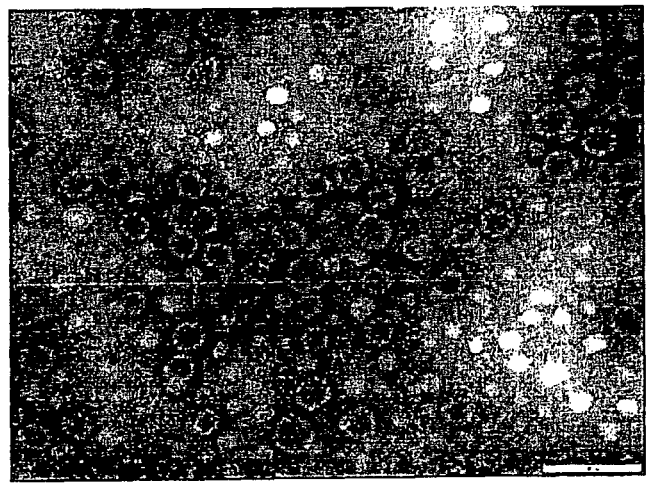
B
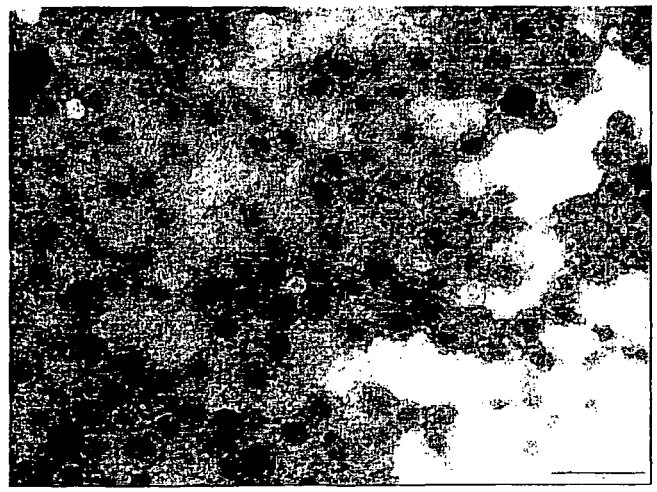
C
FIGURE 23

VLP BASED VACCINE DELIVERY SYSTEM

FIELD OF THE INVENTION

This invention relates to virus-like particles. More particularly, this invention relates to engineered protein molecules for the production of chimeric polyoma virus-like particles.

BACKGROUND TO THE INVENTION

Not more so than in the modern era of global travel has the potential catastrophic consequences of a pandemic arising from respiratory-borne pathogens been so acute. As such there is a striking need for quick and efficient large-scale vaccine production. Influenza virus poses a particular threat because of its capacity to evade the adaptive immune response by mutation. Furthermore, the existence of a sizeable animal reservoir in birds of influenza increases the chance of rapid emergence.

Influenza viruses continuously undergo antigenic variation (antigenic drift and antigenic shift) to evade the immune system of the host. The antigenic variation of influenza viruses forms the primary basis for the occurrence of annual influenza epidemics and occasional pandemics and necessitates constant evolution of vaccine composition. Existing vaccine production methods for influenza rely upon either use of embryonated eggs or cell culture, which are complex and time-consuming processes. Manufacture using these methods also requires specialized and costly infrastructure not widely available. In particular, the current lead time for initial delivery of even small amounts of influenza vaccine is several months following identification of a new pandemic strain. Clearly this amount of time is unacceptable in view of the estimated 1.2 billion high-risk people that will need rapid vaccination with the new and possibly as-yet-unknown vaccine in the event of an influenza pandemic. Further, the ideal method of pandemic prevention is initial containment of outbreaks by rapid vaccination of the entire population in the geographical risk region, not only high-risk young and old. This must occur rapidly and certainly faster than is possible using current vaccine biomanufacturing technologies. The issues of speed and scale are daunting considering the complexity and slowness of existing influenza vaccine technologies, and the need for specialized infrastructure.

Virus-like particles (VLPs) provide a potentially powerful tool in a number of applications including as vaccines, as vehicles for delivery of small molecules and in gene therapy. The potential efficacy of VLP-based vaccines has been postulated for some time and has been demonstrated for cervical cancer vaccines. It is thought that the particulate nature of VLPs induces a more effective immune response than denatured or soluble proteins as immunogens.

VLPs have the added advantage that at no stage during biomanufacture is an infectious virus created. This is distinct to existing embryonated egg technologies and some cell-culture technologies where (i) the starting point of manufacture is the creation of an infectious virus, necessitating high biocontainment during manufacture, and (ii) the virus may be disassembled during processing to remove infectivity (i.e. to reduce the possibility that the vaccine itself might cause disease). This disassembly process has the disadvantage that the virus structure is destroyed and consequently that less-effective denatured or soluble immunogens are administered.

SUMMARY OF THE INVENTION

Due to increasing concern over the imminent threat of pandemic arising from respiratory-borne pathogens, there exists a need for broad-spectrum vaccines which can be rapidly and easily manufactured at large-scale and in swift response to disease outbreak In one broad form, the present invention is directed to a rapid response vaccine manufacturing technology against epidemic virus such as influenza but is not limited thereto. A preferred advantage of the present invention is an automated method using direct PCR ligation to create a multiplicity of antigenic VLPs presenting different parts of a protein of interest.

In another broad form, the invention is directed to generation of a VP1-based VLP which has been engineered and/or modified to include a foreign protein, or a fragment thereof on the surface of said VLP.

In a first aspect, the invention provides an isolated protein comprising a murine polyomavirus VP1 amino acid sequence wherein one or more exposed loops of said murine polyomavirus VP1 amino acid sequence has an insertion of an amino acid sequence of a virus protein other than murine polyomavirus VP1, or a fragment of said virus protein other than murine polyomavirus VP1.

It is contemplated that in particular embodiments that said one or more exposed loops comprise an insertion site selected from the group consisting of site 1, site 3 and site 4.

Preferably, the one or more exposed loops comprise an insertion site selected from the group consisting of site 1 and site 4.

Preferably, the virus protein other than murine polyomavirus VP1 is derived from influenza virus.

Suitably, although not limited thereto, the influenza virus is a H5N1 strain inclusive of variants and newly arising strains such as those resulting from antigenic drift and antigenic shift.

It is envisaged that the virus protein other than murine polyomavirus VP1 can be any class of viral protein which is capable of eliciting an immune response such as, but not limited to, transmembrane proteins, structural proteins and non-structural proteins, or a fragment thereof.

In one embodiment, the virus protein other than murine polyomavirus VP1 is an influenza virus protein selected from the group consisting of hemagglutinin (HA), neuraminidase (NA), nuclear protein (NP), matrix protein M1 and matrix protein M2.

Preferably, the virus protein other than murine polyomavirus VP1 is selected from the group consisting of HA and M2.

Advantageously, the virus protein other than VP 1 corresponds to a hypervariable region of HA.

Preferably, the virus protein other than murine polyomavirus VP1 corresponds to an exposed loop of HA selected from the group consisting of loop A, loop B, loop C, loop D and loop E.

More preferably, the exposed loop of HA is selected from the group consisting of loop A and loop B.

The invention further contemplates that the virus protein other than murine polyomavirus VP1 may be either the same protein in each insertion site or a different protein in each insertion site.

In a second aspect, the invention provides for an isolated nucleic acid encoding the isolated protein of the first aspect.

In one embodiment, the invention provides an isolated nucleic acid encoding a murine polyomavirus VP1 amino acid sequence which has been adapted to receive within one or more exposed loops of said murine polyomavirus VP1 amino acid sequence, an isolated nucleic acid encoding a virus protein other than murine polyomavirus VP1.

In a third aspect, the invention provides an expression construct comprising an isolated nucleic acid according to the second aspect operably-linked to one or more regulatory sequences in an expression vector.

In a fourth aspect, the invention provides a host cell comprising the expression construct of the third aspect.

Preferably, the host cell is selected from the group consisting of a prokaryotic cell and an insect cell.

More preferably, the host cell is a bacterium.

In a fifth aspect, the invention provides a virus-like particle (VLP) comprising one or more isolated proteins of the first aspect.

In a sixth aspect, the invention provides a method of producing an isolated nucleic acid including the step of inserting into each of one or more nucleotide sequences that encode one or more exposed loops of a murine polyomavirus VP1 protein, a nucleotide sequence encoding a virus protein other than murine polyomavirus VP1, or a fragment of said nucleotide sequence encoding a virus protein other than murine polyomavirus VP1.

In a seventh aspect, the invention provides a method of producing a VLP including the steps of:
 (a) introducing the isolated nucleic acid of the second aspect or the expression construct of the third aspect into a host cell;
 (b) culturing said host cell under conditions which facilitate production of the isolated protein of the first aspect;
 (c) optionally purifying the isolated protein of the first aspect; and
 (d) assembling the isolated protein purified according to step (c) to produce the VLP.

In an eighth aspect, the invention provides a pharmaceutical composition comprising an isolated protein, isolated nucleic acid or VLP according to any of the aforementioned aspects and a pharmaceutically acceptable carrier, diluent or excipient.

Preferably, the pharmaceutical composition of the invention is an immunotherapeutic composition.

More preferably, the pharmaceutical composition is a vaccine.

Compositions according to this aspect may be used either prophylactically or therapeutically.

In a ninth aspect, the invention provides a method of treating an animal including the step of administering the pharmaceutical composition of the eighth aspect to prophylactically or therapeutically treat a disease, disorder or condition. It will be appreciated that the disease, disorder or condition can be caused by any infectious organism for which a disease-specific or highly-disease associated antigen is, or will be known.

Preferably, the disease, disorder or condition is caused by a virus such as influenza virus, but is not limited thereto. More preferably, the disease, disorder or condition is caused by an avian influenza virus.

In a tenth aspect, the invention provides a method of immunising an animal including the step of administering the pharmaceutical composition of the eighth aspect to said animal to thereby induce immunity in said animal.

An animal can be selected from the group consisting of humans, domestic livestock, laboratory animals, performance animals, companion animals, poultry and other animals of commercial importance, although without limitation thereto.

Preferably, the animal is a mammal.

More preferably, the animal is a human.

Throughout this specification, unless the context requires otherwise, the words "comprise", "comprises" and "comprising" will be understood to imply the inclusion of a stated integer or group of integers but not the exclusion of any other integer or group of integers.

BRIEF DESCRIPTION OF THE FIGURES

In order that the invention may be readily understood and put into practical effect, preferred embodiments will now be described by way of example with reference to the accompanying figures wherein like reference numerals refer to like parts and wherein:

FIG. 1 Amino acid sequences of generic vectors. The sequences can be identified as follows: VP1 (SEQ ID NO:87); VP1-S1 (SEQ ID NO: 88); VP1-S4 (SEQ ID NO:89); VP1-S3 (SEQ ID NO:90); VP1-S1-S3-S4 (SEQ ID NO:91).

FIG. 2 Amino acid sequences of VP1-S1 vectors with inserted peptides. The sequences can be identified as follows: VP1-S1 (SEQ ID NO: 88); VP1-S1B (SEQ ID NO:92); VP1-S1A (SEQ ID NO:93); VP1-S1M2e (SEQ ID NO:94); VP1-S1hM2e (SEQ ID NO:95).

FIG. 12 Amino acid sequence alignment of HA across various strains of H5N1 subtype of influenza A virus. The boxed regions marked "A" and "B" represent loops A and B respectively. The sequences of full length HA, loop A and loop B respectively may be identified as follows: DQ343152 (SEQ ID NO: 96; SEQ ID NO: 1 and SEQ ID NO:24); DQ343150 (SEQ ID NO:97; SEQ ID NO: 2 and SEQ ID NO:25); DQ343151 (SEQ ID NO: 98; SEQ ID NO: 3 and SEQ ID NO:26); DQ323672 (SEQ ID NO:99; SEQ ID NO: 4 and SEQ ID NO:27); DQ236085 (SEQ ID NO:100; SEQ ID NO: 5 and SEQ ID NO:28); DQ236077 (SEQ ID NO:101;

SEQ ID NO: 6 and SEQ ID NO:29); DQ211925 (SEQ ID NO:102; SEQ ID NO: 7 and SEQ ID NO:30); DQ182483 (SEQ ID NO:103; SEQ ID NO: 8 and SEQ ID NO:31); DQ023145 (SEQ ID NO:104; SEQ ID NO: 9 and SEQ ID NO:32); AY741221 (SEQ ID NO:105; SEQ ID NO:10 and SEQ ID NO:33); AY741219 (SEQ ID NO:106; SEQ ID NO:11 and SEQ ID NO:34); AY741217 (SEQ ID NO:108; SEQ ID NO:12 and SEQ ID NO:35); AY741215 (SEQ ID NO:109; SEQ ID NO:13 and SEQ ID NO:36); AY741213 (SEQ ID NO:110; SEQ ID NO:14 and SEQ ID NO:37); AY646175 (SEQ ID NO:111; SEQ ID NO:15 and SEQ ID NO:38); AY646167 (SEQ ID NO:112; SEQ ID NO:16 and SEQ ID NO:39); AY555153 (SEQ ID NO:113; SEQ ID NO:17 and SEQ ID NO:40); AB239125 (SEQ ID NO:114; SEQ ID NO:18 and SEQ ID NO:41); AB233322 (SEQ ID NO:115; SEQ ID NO:19 and SEQ ID NO:42); AB233321 (SEQ ID NO:116; SEQ ID NO:20 and SEQ ID NO:43); AB233320 (SEQ ID NO:117; SEQ ID NO:21 and SEQ ID NO:44); AB233319 (SEQ ID NO:118; SEQ ID NO:22 and SEQ ID NO:45); AB212649 (SEQ ID NO:119; SEQ ID NO:23 and SEQ ID NO:46).

FIG. 13 Amino acid sequence alignment of HA across various strains of H3N2 subtype of influenza A virus. The boxed regions marked "A" and "B" represent loops A and B respectively. The sequences of full length HA, loop A and loop B respectively may be identified as follows: U97740 (SEQ ID NO:120; SEQ ID NO: 47 and SEQ ID NO:61); P03437 (SEQ ID NO:121; SEQ ID NO: 48 and SEQ ID NO:62); J02132 (SEQ ID NO:122; SEQ ID NO:49 and SEQ ID NO:63); J02090 (SEQ ID NO:123; SEQ ID NO:50 and SEQ ID NO:64); DQ508929 (SEQ ID NO:124; SEQ ID NO:51 and SEQ ID NO:65); DQ508865 (SEQ ID NO:125; SEQ ID NO:52 and SEQ ID NO:66); DQ508849 (SEQ ID NO:126; SEQ ID NO:53 and SEQ ID NO:67); DQ508833 (SEQ ID NO: 127; SEQ ID NO: 54 and SEQ ID NO:68); DQ508825 (SEQ ID NO: 128; SEQ ID NO:55 and SEQ ID NO:69); AY779254 (SEQ ID NO:129; SEQ ID NO:56 and SEQ ID NO:70); AY779253 (SEQ ID NO:130; SEQ ID NO:57 and SEQ ID NO:71); AB019356 (SEQ ID NO:131; SEQ ID NO:58 and SEQ ID NO:72); AB019354 (SEQ ID NO:132; SEQ ID NO:59 and SEQ ID NO:73); AAA43099 (SEQ ID NO:133; SEQ ID NO:60 and SEQ ID NO:74).

FIG. 14 Amino acid sequence alignment of VP1 vectors carrying HA loop A and loop B of influenza strain H3N2 inserted in S1 of VP1. The sequences can be identified as follows: VP1-S1 (SEQ ID NO:88); VP1-S1H3A (SEQ ID NO:134); VP1-S1H3B (SEQ ID NO:135).

FIG. 15 Amino acid sequence alignment of VP1 vectors carrying HA loop A and loop B of influenza strain H3N2 inserted into S4 of VP1. The sequences can be identified as follows: VP1-S4 (SEQ ID NO:89), VP1-S4-H3A (SEQ ID NO:136), VP1-S4H3B (SEQ ID NO:137).

Figure 16:
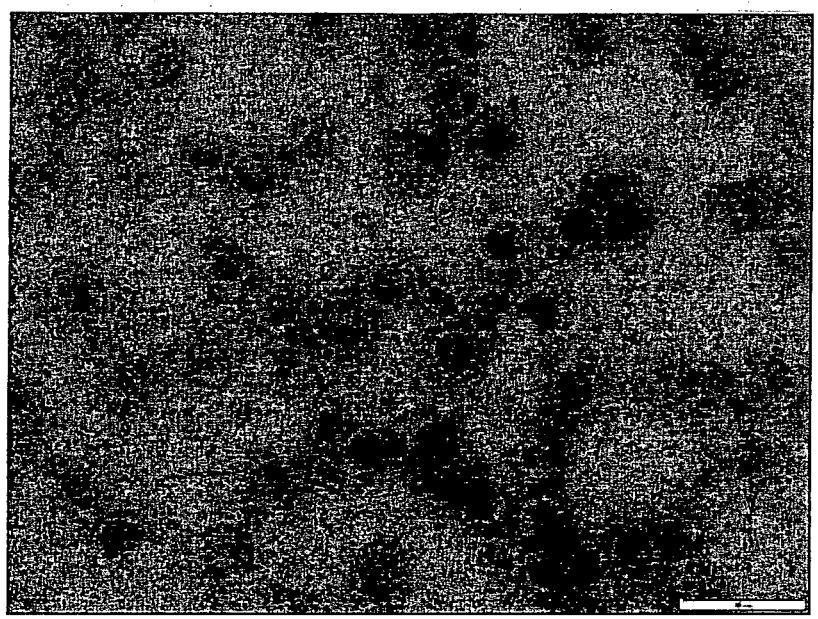

FIG. 16 EM images of VP1-H3-S1A VLPs. Magnification is 200,000× (Scale-bar 100 nm).

Figure 17:
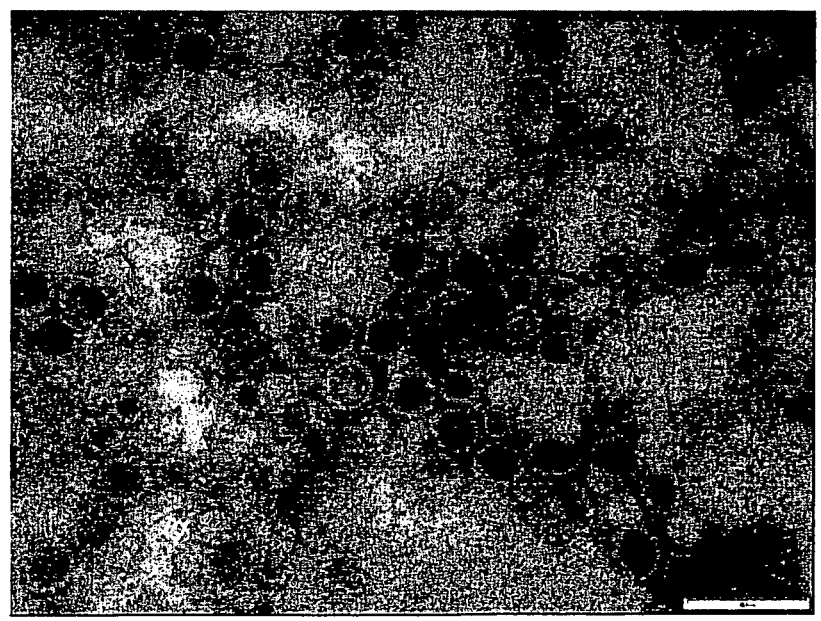

FIG. 17 EM images of VP1-H3-S 1B VLPs. Magnification is 200,000×. (Scale-bar 100 nm).

FIG. 18 Amino acid sequence alignment of VP1 vectors carrying HA loop A and loop B of influenza strain H5N1 inserted into S4 of VP1. The sequences can be identified as follows: VP1-S4 (SEQ ID NO:89), VP1-S4A (SEQ ID NO:138), VP1-S4B (SEQ ID NO:139), VP1-S4hM2e (SEQ ID NO:140).

Figure 19A:
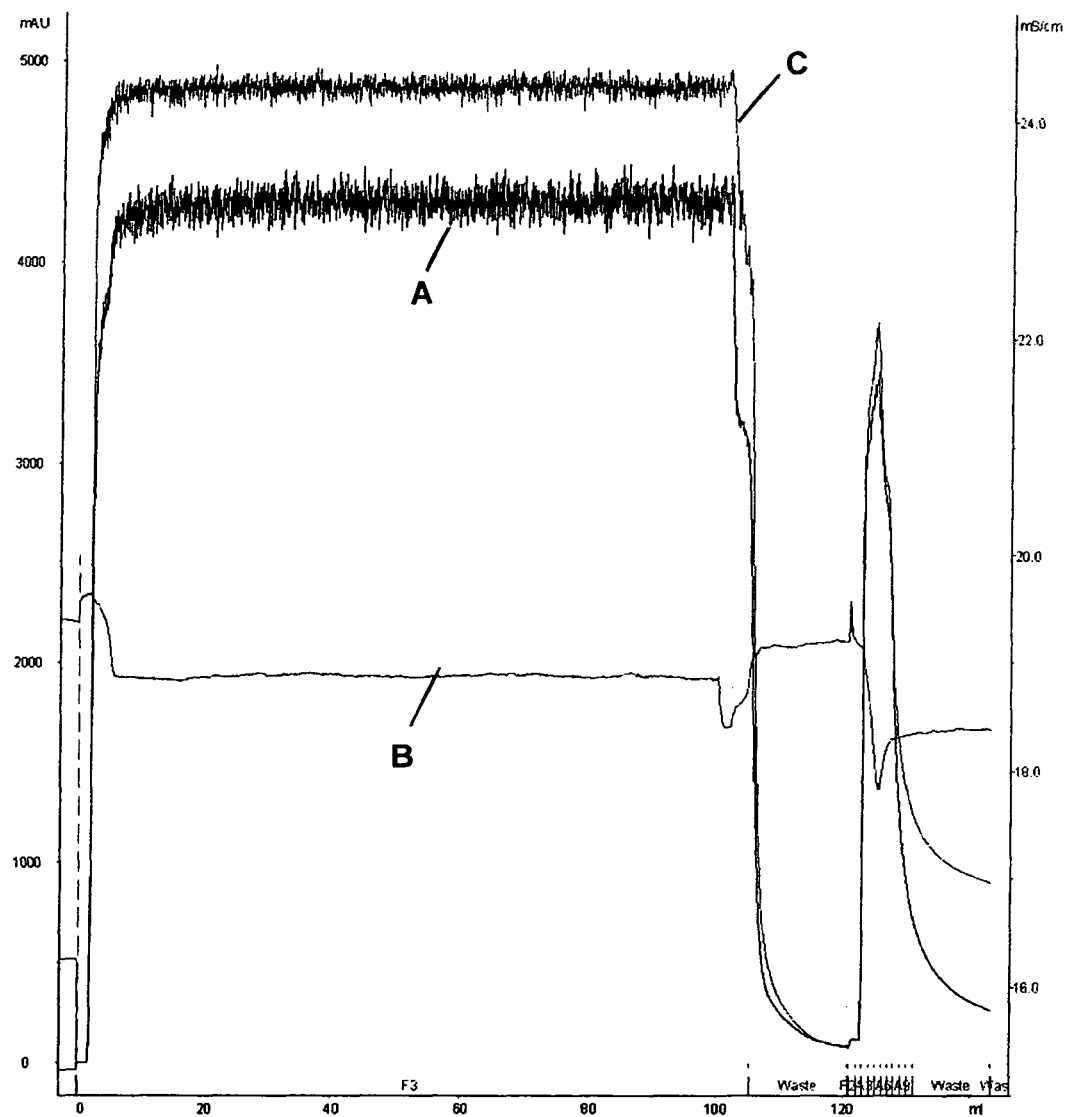
Figure 19B:
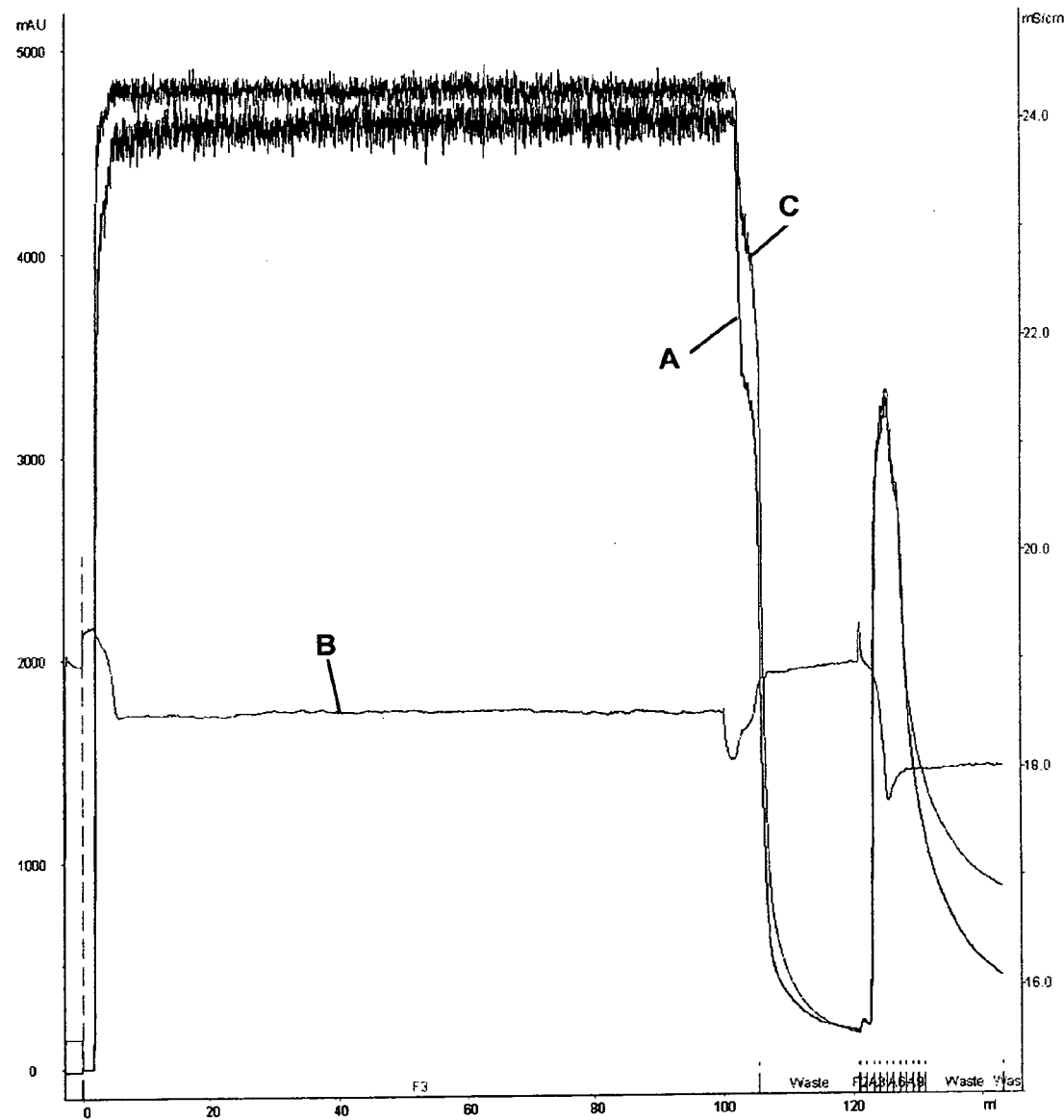

FIG. 19 Purification of GST-VP1-S4A (FIG. 19A) and GST-VP1-S4B (FIG. 19B) using GSTrap HP column. X-axis is volume in ml; Y1 is absorbance in mAU; Y2 is conductivity in mS/cm. Line A represents the UV trace at 280 nm; Line C represents UV trace at 260 nm; Line B represents the conductivity trace; the vertical dashed line is the injection point of sample onto the column.

Figure 20A:
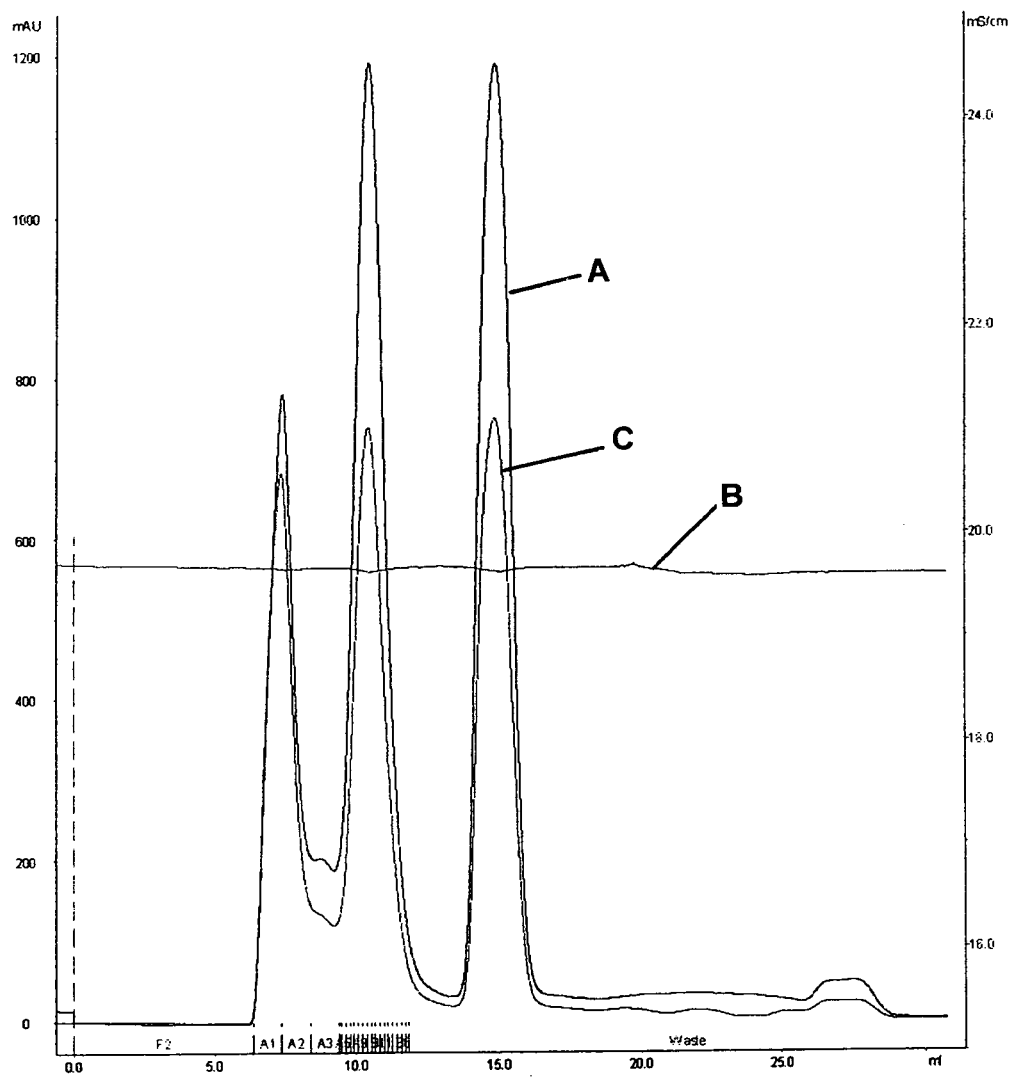
Figure 20B:
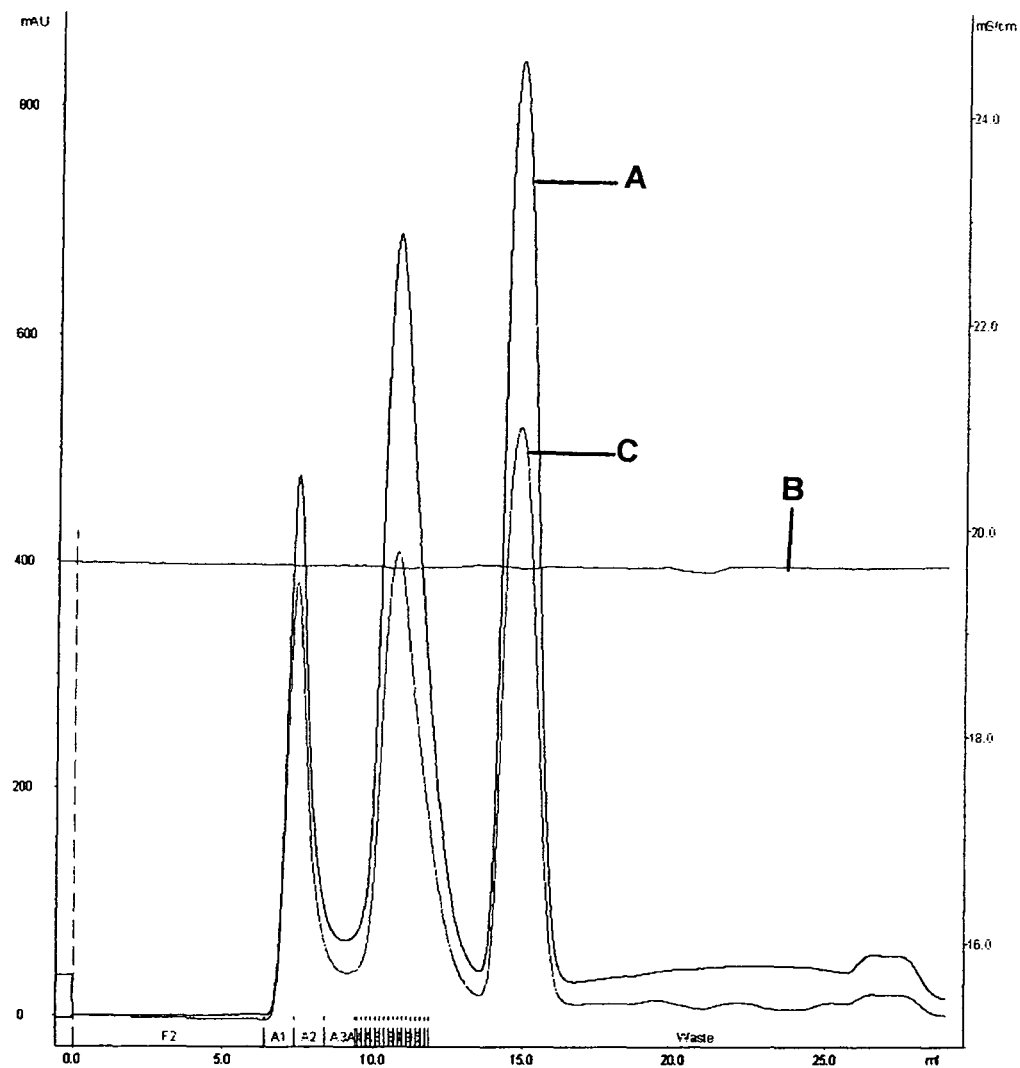

FIG. 20 Separation of thrombin digestion and capsomere purification of GST-VP1-S4A (FIG. 20A) and GST-VP1-S4B (FIG. 20B) on a Superdex S200 10/300 GL size exclusion column (GE Healthcare). X-axis is volume in ml; Y1 is absorbance in mAU; Y2 is conductivity in mS/cm. Line A represents the UV trace at 280 nm; Line C represents UV trace at 260 nm; Line B represents conductivity trace; the vertical dashed line is the injection point of sample onto the column.

Figure 21:
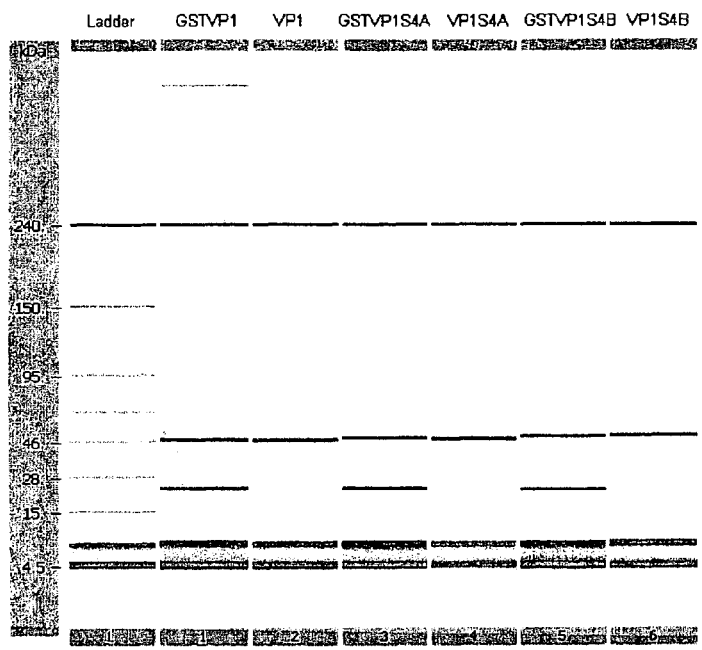

FIG. 21 Comparison of GST-VP1 with GST-VP1-S4A and GST-VP1-S4B by bioanalyzer analysis.

Figure 22:
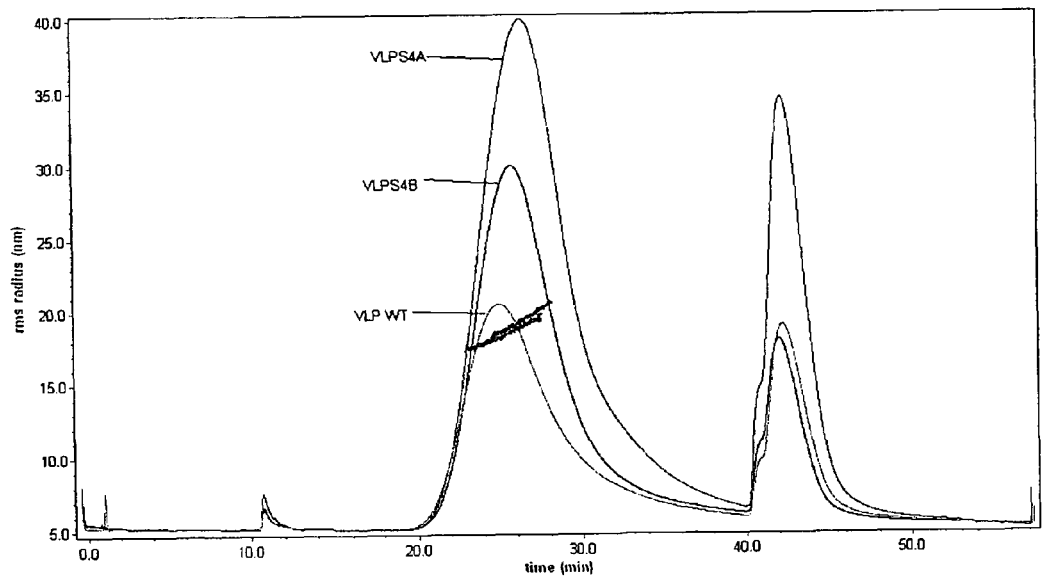

FIG. 22 AFFF plot showing assembled GST-VP1-S4A and GST-VP1-S4B VLPs. X-axis is time (minutes) and Y-axis is rms radius (nm).

FIG. 23 EM images of VP1-S4A (FIG. 23 A), VP1-S4B (FIG. 23 B) and wild-type VP1 (FIG. 23 C). Magnification of all images is 200,000× (scale-bar 100 nm).

DETAILED DESCRIPTION OF THE INVENTION

The isolated proteins of the present invention and VLPs derived therefrom provide a new and advantageous broad spectrum vaccine for treatment of emerging diseases and, in particular, influenza. Surprisingly, the inventors have utilised the natural mechanism which viruses have evolved to evade adaptive immunity to produce a broad-spectrum vaccine which can be manufactured rapidly in response to a new viral threat, has low manufacturing costs and low requirements for specialised infrastructure during manufacture, and complies with regulatory standards.

In particular, present conventional approaches in eukaryotes to VLP vaccine production principally rely upon in vivo assembly of the VLP from overexpression of the viral proteins and extensive ex vivo post-expression processing to separate the VLP from structurally related contaminants, DNA and harmful unrelated viruses that may be present as a result of the cell culture process or else through contamination during the extended times required for cell culture. Separation of the VLP from viruses having closely related physical properties presents a significant processing challenge. VLP vaccines to influenza based on eukaryotic expression of full-length HA and M protein, with or without co-expression of NA, also incorporate an ill-defined membrane which is labile during processing, giving complex and heterogeneous VLP structures following purification. These problems with existing VLP vaccines remain largely unresolved for influenza vaccines, particularly for complex structures such as those comprising HA, M and/or NA protein that must be assembled in vivo.

The present invention overcomes the purification-separation problems and avoids the creation of a VLP having a complex structure including a labile membrane. By creating a simple minimalist VLP structure, this invention enables disassembly-reassembly processing of the VLP structure.

For culture methods that create a relatively simple VLP structure in vivo, that is for example a VLP comprising one foreign protein, such VLPs can be disassembled and the VLP protein purified with high efficiency using conventional technologies widely available at large scale. Purified protein can be sterile filtered to ensure removal of adventitious virus, as routinely practised for conventional protein therapeutics. Following the preparation of purified sterile-filtered protein, the VLP is recreated in vitro through appropriate chemical control of the reactor environment.

For culture methods that do not create a VLP structure in vivo (e.g. using fast-growing bacterium such as *E. coli*), the process of manufacture is further speeded and simplified. In such cases the current invention is not predicated on the availability of specialised infrastructure nor extended cultivation times, allowing for rapid production in diverse manufacturing sites using technologies widely available for the production of protein therapeutics. The use of a simple and minimalist VLP structure allows for the creation of a VLP structure through in vitro assembly after protein expression and purification.

Regardless of the culture method employed, the approach of present invention of in vitro assembly following protein purification and sterile filtering provides for precise control of the VLP assembly step. The assembly of the VLP structure is under control of the process operator thus removing limitations inherent for in vivo assembly approaches. This improved control overcomes problems with conventional VLP technologies, and in particular, for influenza VLP vaccines, and produces a superior VLP which has higher morphological homogeneity. Precise control of VLP assembly also allows for the incorporation of precisely defined antigenic DNA sequences into the growing VLP structure, under the control of the process operator, giving opportunity for rapid evolution of vaccine design.

Isolated Proteins

It is appreciated by a person of skill in the art that VP1 from polyomavirus is particularly well suited to the present invention. Preferably, the VP1 is derived from murine polyomavirus.

Although not wishing to be bound by any particular theory, the presence of loops on the surface of a virus particle provide ideal candidates for recognition by the immune system. Such loops are particularly suitable if tolerant to insertion of foreign sequences without disruption to the protein structure.

Although not limited thereto, VP1 comprises four surface exposed loops which span around about residues 82-89, 221-224, 247-249 and 292-297 and are referred to as site 1, site 2, site 3 and site 4 respectively. In the context of the present invention, typically, although not exclusively, at least one exposed loop site has an insertion. It can be appreciated that to facilitate generation of a more potent or, alternatively a broad-spectrum VLP, one, two, three or four sites may comprise an insertion.

Preferably, one, two or three exposed loops comprise an insertion. More preferably, the one or more exposed loops comprising an insertion are selected from the group consisting of site 1, site 3 and site 4.

In more preferred embodiments, the one or more exposed loops comprising an insertion are selected from the group consisting of site 1 and site 4.

The isolated protein of the invention may be referred to hereinafter as a "VP1 chimera". By "chimera" is meant a fusion between at least two proteins or a fusion between fragments of said at least two proteins. Typically, although not exclusively, the proteins are unrelated however it is readily contemplated that the proteins may be homologues.

By "protein" is meant an amino acid polymer. The amino acids may be natural or non-natural amino acids, D- or L-amino acids as are well understood in the art.

The term "protein" includes and encompasses "peptide", which is typically used to describe a protein having no more than fifty (50) amino acids and "polypeptide", which is typically used to describe a protein having more than fifty (50) amino acids.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native or recombinant form.

The invention also contemplates use of a fragment of the VP1 chimera or alternatively, a fragment of the virus protein other than VP1.

In one embodiment, a "fragment" includes a protein comprising an amino acid sequence that constitutes less than 100% of an amino acid sequence of an entire VP1 or a virus protein other than VP1.

In the general embodiments which contemplate a fragment of the VP1 chimera, preferably the fragment comprises less than 99%, 98%, 97%, 96%, 95%, 94%, 93%, 92%, 91%, 90%, 85%, 80%, 75% or 70%, but greater than 50%, of the entire protein.

In the other general embodiments which contemplate a fragment of the virus protein other than VP1, preferably the fragment comprises less than 99%, 98%, 97%, 96%, 95%, 94%, 93%, 92%, 91%, 90%, 85%, 80%, 75%, 70%, 65%, 60%, 55% or 50% but can also relate to a peptide as hereinbefore described.

Preferably, the fragment is a "biologically active" fragment, which retains biological, structural and/or physical activity of a given protein, or an encoding nucleic acid. In the context of VP1, the biologically active fragment preferably has the ability to self-assemble and form VLPs.

The choice of which virus protein other than VP1 to insert into the exposed loops can be made taking into account the particular desired end result. The invention is well suited to proteins which are involved in eliciting an immune response to a pathogen such as, but not limited to, influenza virus, human immunodeficiency virus, hepatitis C virus, Ebola virus, measles virus, parainfluenza virus and respiratory syncytial virus. The invention is particularly suited to proteins that are subject to continuous alteration in circulating epidemic strains. It is envisaged that fragments which correspond to antigenic epitopes of the virus protein other than VP1 can be used for insertion.

By "corresponds to" in the context of the present invention, is meant an amino acid sequence which shares primary sequence characteristics of another amino acid sequence but is not necessarily derived or obtained from the same source as said another amino acid sequence.

In one embodiment, the virus protein other than VP1 is a protein from influenza virus such as HA, NP, NA, M1 or M2.

In a preferred embodiment, the virus protein other than VP1 is selected from the group consisting of HA and M2.

In another preferred embodiment, the virus protein other than VP1 is a domain of M2. Typically, although not exclusively, the domain of M2 is an ectodomain.

In particular preferred embodiments, the virus protein other than VP1 corresponds to an exposed loop of HA selected from the group consisting of loop A, loop B, loop C, loop D and loop E, or a fragment thereof. Preferably, the exposed loop of HA is selected from the group consisting of loop A, loop B, loop C and loop E. More preferably, the exposed loop of HA is selected from the group consisting of loop A and loop B.

In other particular preferred embodiments, the fragment of a virus protein other than VP1 is an antigenic epitope. In more preferred embodiments, the fragment is an antigenic epitope of HA. In even more preferred embodiments, the fragment is an antigenic epitope of an exposed loop of HA selected from the group consisting of loop A, loop B, loop C and loop E.

A person skilled in the art will appreciated that viruses have evolved a number of mechanisms to evade the host cell immune response and, as a consequence, lead to generation of escape mutants. One such mechanism is the presence of a region within a virus protein/s with a high degree of variability, the so named hypervariable region.

It will further be appreciated that the variability within an antigenic epitope between virus subtypes, and in particular influenza virus subtypes, can be substantial. Advantageously, although not exclusively, loop A and loop B comprise a minimal region which display a high degree of variability across virus subtypes.

Therefore in general embodiments where the virus protein other than VP1 is HA derived from a H5 subtype of influenza virus, at least one consensus amino acid sequence for an antigenic epitope of loop A is PYqGKSS (SEQ ID NO:75) (there is common q<-->N and K<-->R variability) whereas at least one consensus sequence for an antigenic epitope of loop B is PNDAAEQTKLYQNPTTY (SEQ ID NO:76) (there is common K<-->R variability), although without limitation thereto.

In other general embodiments where the virus protein other than VP1 is HA derived from a H3 subtype of influenza virus, at least one consensus amino acid sequence for an antigenic epitope of loop A is KRGPgSG (SEQ ID NO:77) (there is common PgS<-->PaS variability) whereas at least one consensus amino acid sequence for an antigenic epitope of loop B is PSTNQEQTsLYVQASGR (SEQ ID NO:78) (there is common TsL<-->TNL variability), although without limitation thereto.

In yet other general embodiments where the virus protein other than VP1 is HA derived from a H1 subtype of influenza virus, at least one consensus amino acid sequence for an antigenic epitope of loop A is SHKGKSS (SEQ ID NO:79), whereas at least one consensus amino acid sequence of loop B is PSNIEDQKTIYRKENAY (SEQ ID NO:80), although without limitation thereto.

The present invention also contemplates variants of the virus protein other than VP1.

In light of the foregoing, it will be appreciated that a variant includes within its scope a natural variant such as, although not limited to, a variant arising from natural antigenic variation of a virus wherein one or more residues are different to at least one consensus sequence. It will be appreciated that an absence of primary amino acid consensus sequence between antigenic epitopes from different virus subtypes is not unexpected considering the propensity for a number of viruses, including influenza, to undergo antigenic shift and antigenic drift in order to generate escape mutants. Hence a variant includes variation within the subtypes of a virus and/or variation between subtypes of a virus, but is not limited thereto. By way of example only, at least one consensus amino acid sequence for loop A derived from a H5 variant of influenza A virus is PYNGKSS (SEQ ID NO: 81) whereas the corresponding region in HA from H3 subtype is KRGPGSG (SEQ ID NO: 82).

According to the aforementioned embodiments, variants are contemplated where the substitutions in amino acid sequences are conservative in nature.

Exemplary variant antigenic epitopes of loop A and loop B from HA are listed in FIG. 12 and FIG. 13.

Therefore it is further contemplated that either a hypervariable region or a conserved region of a virus protein other than VP1 may be inserted into the VP1 chimera, or a combination thereof.

The invention therefore also contemplates variants of epitopes, isolated proteins and encoding nucleic acids which share an appropriate level of sequence identity with isolated proteins and encoding nucleic acids as set forth herein.

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, U) or amino acid residue occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

In particular embodiments, variants will share at least 30%, 40%, 50%, 55%, 60%, 65%, 70%, 75%, 80%, 85% or 90% and more preferably at least 95%, 96%, 97%, 98% or 99% sequence identity with the isolated proteins and/or isolated nucleic acids of the invention. It will be appreciated that a variant comprises all integer values less than 100%, for example the percent value as set forth above and others.

The VP1 chimera may also comprise one or more additional amino acid sequences. "Additions" of amino acids may include fusion of a VP1 protein of the invention or a fragment thereof with other proteins or peptides. The other protein may, by way of example, assist in the purification of the protein. For instance, these include a polyhistidine tag, maltose binding protein (MBP), green fluorescent protein (GFP), Protein A or glutathione S-transferase (GST). Other additions include "epitope tags" such as FLAG and c-myc epitope tags. It is further contemplated that more than one fusion partner may be included into the isolated protein.

Well known examples of fusion partners include, but are not limited to, glutathione-S-transferase (GST), Fc portion of human IgG, maltose binding protein (MBP), NusA and hexahistidine ($HIS_6$), which are particularly useful for isolation of the fusion protein by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

In some cases, the fusion partners also have protease cleavage sites, such as for Factor $X_a$, Thrombin or human rhinovirus 3C protease, which allow the relevant protease to partially digest the fusion protein of the invention and thereby liberate the recombinant protein of the invention therefrom. The liberated protein can then be isolated from the fusion partner by subsequent chromatographic separation.

The invention also contemplates chemical derivatives of the VP1 chimera, such as produced using techniques described in CURRENT PROTOCOLS IN PROTEIN SCIENCE Chapter 15, for example.

In particularly preferred embodiments, the isolated protein or VP1 chimera of the present invention comprises an amino acid sequence selected from the group consisting of SEQ ID NO:92; SEQ ID NO:93; SEQ ID NO:94; SEQ ID NO:95;

SEQ ID NO:134; SEQ ID NO:135; SEQ ID NO:136; SEQ ID NO:137; SEQ ID NO:138; SEQ ID NO:139; and SEQ ID NO:140.

Isolated Nucleic Acids and Expression Constructs

It will be appreciated from the foregoing and also from pharmaceutical compositions described in more detail hereinafter, that the invention also provides use of an isolated nucleic acid encoding the VP1 chimeric protein of the invention. Non-limiting examples of isolated nucleic acids are provided in FIGS. 1 and 2.

The term "nucleic acid" as used herein designates single- or double-stranded mRNA, RNA, cRNA and DNA inclusive of cDNA, genomic DNA and DNA-RNA hybrids. Nucleic acids may also be conjugated with fluorochromes, enzymes and peptides as are well known in the art.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

It can be readily appreciated by a person of skill in the art that the isolated nucleic acids of the present invention may be produced and manipulated using an assortment of recombinant techniques. Examples of preparation of such isolated nucleic acids is given in Examples 1 and 2.

In a preferred embodiment, the nucleotide sequences encoding the one or more exposed loops of VP1 are adapted to receive an isolated nucleic acid encoding a virus protein other than VP1. By "adapted to receive" is meant the manipulation, by recombinant means or other, of nucleotide sequences in order to facilitate insertion, excision or mutagenesis of native or foreign nucleotide sequences. By way of example only, a nucleotide sequence may be engineered to incorporate new restriction enzyme sites in order to improve the speed and efficiency of cloning procedures. Although not limited thereto, restriction enzymes that do not create an overhang are the most amenable to high speed cloning of amplification products generated by PCR with super high-fidelity polymerases such as Pfx. A nucleotide sequence adapted in such a manner is also amenable to high-throughput screening of vaccine candidates.

A person of skill in the art would readily appreciate that mutagenesis can be performed using an assortment of recombinant techniques. Non-limiting examples of suitable techniques include random mutagenesis (e.g., transposon mutagenesis), oligonucleotide-mediated (or site-directed) mutagenesis, PCR mutagenesis and cassette mutagenesis.

In a preferred embodiment, the isolated nucleic acid comprises a nucleotide sequence encoding the VP1 chimera wherein the nucleotide sequence of one or more exposed loops has been mutated to include a recognition site for a restriction enzyme which generates blunt-ends.

The invention also contemplates variant VP1 nucleic acids having one or more codon sequences altered by taking advantage of codon sequence redundancy.

A particular example of a variant VP1 nucleic acid is optimization of a nucleic acid sequence according to codon usage, as is well known in the art. This can effectively "tailor" a nucleic acid for optimal expression in a particular organism, or cells thereof, where preferential codon usage has been established.

The invention further contemplates an expression construct comprising an isolated nucleic acid encoding the VP1 chimera operably-linked to one or more regulatory sequences in an expression vector.

An "expression vector" may be either a self-replicating extra-chromosomal vector such as a plasmid, or a vector that integrates into a host genome, inclusive of vectors of viral origin such as adenovirus, lentivirus, poxvirus and flavivirus vectors as are well known in the art.

By "operably linked" is meant that said regulatory nucleotide sequence(s) is/are positioned relative to the recombinant nucleic acid of the invention to initiate, control, regulate or otherwise direct transcription and/or other processes associated with expression of said nucleic acid.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences, enhancer or activator sequences and nucleic acid packaging signals.

Preferably, said promoter is operable in a bacterial cell. Non-limiting examples include T7 promoter, tac promoter and T5 promoter.

Inducible/repressible promoters (such as tet-repressible promoters and IPTG-, alcohol-, metallothionine- or ecdysone-inducible promoters) are well known in the art and are contemplated by the invention, as are tissue-specific promoters such as α-crystallin promoters. It will also be appreciated that promoters may be hybrid promoters that combine elements of more than one promoter (such as SRα promoter).

The expression construct may also include a fusion partner (typically provided by the expression vector) so that the VP1 chimera is expressed as a fusion protein with said fusion partner, as hereinbefore described. Expression constructs may also include a selection marker nucleic acid that confers transformed host cell resistance to a selection agent. Selection markers useful for the purposes of selection of transformed bacteria include bla, kanR and tetR while transformed eukaryotic cells may be selected by markers such as hygromycin, G418 and puromycin, although without limitation thereto.

Expression constructs may be introduced into cells or tissues, inclusive of cells capable of VLP production, by any of a number of well known methods typically referred to as "transfection" "transduction", "transformation" and the like. Non-limiting examples of such methods include transformation by heat shock, electroporation, DEAE-Dextran transfection, microinjection, liposome-mediated transfection (e.g. lipofectamine, lipofectin), calcium phosphate precipitated transfection, viral transformation, protoplast fusion, microparticle bombardment and the like.

It is readily contemplated that any recombinant protein expression system may be used for the present invention such as bacterial, yeast, plant, mammalian and insect-based expression systems but is not limited thereto.

In one preferred embodiment, recombinant protein expression occurs in cells of prokaryotic origin. Suitable host cells for recombinant protein expression are bacterial cells such as *Escherichia coli* (BL21 and various derivative strains thereof which have been optimised for certain applications, such as Rosetta, for example).

Methodology for Production of VLPs One broad application of the isolated proteins, isolated nucleic acids and expression constructs of the present invention is a platform technology for production of a vaccine. In particular, the present invention facilitates rapid assembly and production of VLPs in vitro.

Many methods are well known in the art for VLP assembly. Pattenden and co-workers (2005, Trends in Biotechnology 10: 523-529) provides a non-limiting example of such methodology. The present invention readily contemplates both in vivo and in vitro approaches to VLP assembly however the invention is particularly suited to in vitro processes for assembly of VLPs. Advantages conferred by in vitro methods include high compositional consistency and a process which is readily controlled and amenable to scale-up.

Typically, although not exclusively, in vitro assembly method of VLPs comprises overexpression of a pentameric subunit of a self-assembly protein, such as VP1 or the VP1 chimera of the present invention, in a recombinant expression system as described above. Although not limited thereto, advantageously the recombinant protein is expressed in the soluble fraction of the cell. The recombinant protein may be subsequently purified using a combination of tag removal, filtration and/or chromatography techniques, followed by sterile filtration, which are well known in the art. This lack of a requirement for specialised infrastructure and the use of well-known readily scaleable operations makes the current invention distinctly advantageous. Subsequent self-assembly of these subunits into a VLP is achieved by means of controlled changes in the physicochemical environment containing these subunits. By way of example only, assembly of VLPs may be more favourable under high salt or alternatively, low salt conditions. Inclusion and/or removal of low-molecular weight compounds such as glycerol and carbohydrates may also facilitate the assembly reaction. Methods typically known in the art such as buffer exchange by dialysis, dilution or size exclusion chromatography may be utilised to effect the changes in the physicochemical conditions of the subunits, but is not limited thereto.

A recombinant protein may be conveniently prepared by a person skilled in the art using standard protocols as for example described in Sambrook et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

By "purify", "purified" and "purification", particularly in the context of recombinant protein purification, is meant enrichment of a recombinant protein so that the relative abundance and/or specific activity of said recombinant protein is increased compared to that before enrichment.

By "chromatography" such as in the context of chromatographic steps of the invention, is meant any technique used for the separation of biomolecules (eg protein and/or nucleic acids) from complex mixtures that employs two phases: a stationary bed phase and a mobile phase that moves through the stationary bed. Molecules may be separated on the basis of a particular physicochemical property such as charge, size, affinity and hydrophobicity.

Chromatography may be performed by a person skilled in the art using standard protocols as for example described in CURRENT PROTOCOLS IN PROTEIN SCIENCE Eds. Coligan et al., (John Wiley & Sons, Inc. 1995-1999) which is incorporated by reference herein, in particular Chapters 8 and 9.

The invention also readily contemplates overexpression of the isolated proteins and isolated nucleic acids of the present invention to generate an intact VLP, which obviates the need for an in vitro assembly process. A person skilled in the art will appreciate that there are a variety of expression systems which are suited for this application such as, but not limited to, mammalian-based and insect-based expression systems. In general embodiments, the baculovirus expression system is particularly amenable to expression of an intact VLP of the invention.

It will be appreciated that because of the flexibility of the present invention, a VLP assembled according to the method of the present invention may comprise a VP1 backbone with the following combinations inserted into the exposed loops: (a) a single protein from a single virus; (b) a plurality of different proteins from the same virus; or (c) a mixture of proteins from various viruses. The present invention is also readily amenable to production of a mixed population of VLPs wherein one or more VP1 chimeras according to (a), (b) or (c) are assembled into VLPs to thereby produce a multivalent vaccine delivery system. The present invention is also contemplates production of a mixed population of VLPs by means of introduction of one or more expression constructs into a cell.

Pharmaceutical and Immunotherapeutic Compositions, Vaccines and Methods of Treatment The present invention provides a VP1 chimera which exploits the self-assembly capacity of VP1 and the potential immunogenicity of exposed loops as a vehicle for delivery for VLP production and vaccine delivery. However, the invention more broadly provides a pharmaceutical composition not limited to use in vaccine delivery, but inclusive of pharmaceutical compositions in several forms such as vessels for the delivery of a number of palliatives such as, but not limited to, small molecules, catalytic nucleic acids such as ribozymes and nucleic acids for gene therapy.

The pharmaceutical composition may further comprise a pharmaceutically-acceptable carrier, diluent or excipient.

In a preferred form, the pharmaceutical composition of the invention is an immunogenic composition comprising an isolated protein, isolated nucleic acid or VLP and an immunologically acceptable carrier, diluent or excipient.

By "immunogenic" is meant capable of eliciting an immune response, preferably a protective immune response, upon administration to a host.

Thus in a particular form, the immunogenic composition of the invention may be a vaccine which induces a protective immune response when administered to a host.

It will be appreciated that compositions, vaccines and methods of treatment may be used therapeutically or prophylactically.

Suitably, the immunogenic composition and/or vaccine of the invention is administrable to an animal host, inclusive of domestic animals, livestock, performance animals and humans.

Any suitable procedure is contemplated for producing vaccine compositions. Exemplary procedures include, for example, those described in New Generation Vaccines (1997, Levine et al., Marcel Dekker, Inc. New York, Basel, Hong Kong) which is incorporated herein by reference.

As hereinbefore described, the immunogenic composition and/or vaccine of the invention may include an "immunologically-acceptable carrier, diluent or excipient".

Useful carriers are well known in the art and include for example: thyroglobulin; albumins such as human serum albumin; toxins, toxoids or any mutant crossreactive material (CRM) of the toxin from tetanus, diptheria, pertussis, *Pseudomonas, E. coli, Staphylococcus*, and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a T cell epitope of a bacterial toxin, toxoid or CRM may be used. In this regard, reference may be made to U.S. Pat. No. 5,785,973 which is incorporated herein by reference.

The "immunologically-acceptable carrier, diluent or excipient" includes within its scope water, bicarbonate buffer, phosphate buffered saline or saline and/or an adjuvant as is well known in the art.

As will be understood in the art, an "adjuvant" means one or more substances that enhances the immunogenicity and/or efficacy of a vaccine composition. Non-limiting examples of suitable adjuvants include squalane and squalene (or other oils of animal origin); block copolymers; detergents such as Tween®-80; Quil® A, mineral oils such as Drakeol or Marcol, vegetable oils such as peanut oil; *Corynebacterium*-derived adjuvants such as *Corynebacterium parvum; Propionibacterium*-derived adjuvants such as *Propionibacterium acne; Mycobacterium bovis* (Bacille Calmette and Guerin or BCG); interleukins such as interleukin 2 and interleukin 12; monokines such as interleukin 1; tumour necrosis factor; interferons such as gamma interferon; surface active substances such as hexadecylamine, octadecylamine, octadecyl amino acid esters, lysolecithin, dimethyldioctadecylammonium bromide, N,N-dicoctadecyl-N',N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; combinations such as saponin-aluminium hydroxide or Quil-A aluminium hydroxide; liposomes; ISCOM® and ISCOMATRIX® adjuvant; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol' EMA; acrylic copolymer emulsions such as Neocryl A640 (e.g. U.S. Pat. No. 5,047,238); vaccinia or animal poxvirus proteins; sub-viral particle adjuvants such as cholera toxin, or mixtures thereof.

Any safe route of administration may be employed for providing a patient with the immunotherapeutic composition of the invention. For example, oral, rectal, parenteral, sublingual, buccal, intravenous, intra-articular, intra-muscular, intra-dermal, subcutaneous, intranasal, inhalational, intraocular, intraperitoneal, intracerebroventricular, transdermal and the like may be employed. Intra-muscular and subcutaneous injection is appropriate, for example, for administration of immunogenic compositions and vaccines.

Dosage forms include tablets, dispersions, powders, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

Immunotherapeutic compositions of the invention may be used to prophylactically or therapeutically immunize animals such as humans.

However, other animals are contemplated, preferably vertebrate animals including domestic animals such as livestock and companion animals.

Immune responses may be induced against viruses by expressing appropriately immunogenic proteins and peptide epitopes inclusive of polyepitopes using the vaccine of the invention. A non-limiting list of potential viruses include influenza virus, human immunodeficiency virus, hepatitis C virus, Ebola virus, measles virus, parainfluenza virus and respiratory syncytial virus.

It is envisaged that an immune response involves induction of antibodies and/or T-cells.

So that the invention may be readily understood and put into practical effect, the following non-limiting Examples are provided.

EXAMPLES

Example 1

Construction of Generic Vectors Carrying VP1 Sequences Able to Accept Antigenic Peptide Sequences Murine polyomavirus VP1 sequence (GenBank accession number: M34958) was cloned between the BamHI and XhoI sites within the multiple cloning site of the commercial vector pGEX-4T-1 (GE healthcare). Surface-exposed loops of polyomavirus VP1 are known as Site 1, Site 2, Site 3 and Site 4. These sites can tolerate insertion of peptide sequences without disrupting the structure of VP1.

Sites 1-4 (S1-4) were identified on murine polyomavirus VP1 (GenBank accession number: M34958). Three unique blunt-end restriction sites were created in the S1, S3 and S4 of VP1. No restriction site was created in S2 as it is not a favourable site for insertion of foreign peptides. Blunt-end restriction sites were chosen, as they allowed rapid cloning of any peptide sequences into VP1 without the need to create sticky ends on vectors/inserts. This strategy also removes the possibility of incompatible restriction sites that may be present on target peptide sequence.

The amino acid sequence of VP1 present in the generic vectors is depicted in FIG. 1. S1 of VP1 was mutated to include NaeI restriction site (LATSDTED; SEQ ID NO: 107 mutated to LATSAGTED; SEQ ID NO: 141). S3 of VP1 was mutated to include PmlI restriction site (GTT: SEQ ID NO: 142 mutated to GTHV; SEQ ID NO: 143). S4 of VP1 was mutated to include AfeI restriction site (TRNYDV; SEQ ID NO: 144 mutated to TRSAYDV; SEQ ID NO: 145).

Resulting generic vectors with modified VP1 sequences to enable the insertion of one or multiple foreign peptides are: pGEX4T1-VP1 S1, pGEX4T1-VP1 S3, pGEX4T1-VP1 S4, pGEX4T1-VP1 S1/S4 and pGEX4T1-VP1 S1/S3/S4.

Example 2

Construction and Sequencing of Vectors Expressing a Foreign Antigen

Construction and Sequencing of Vectors Carrying HA Epitopes from Loop A and Loop B of H5N1:

E. coli codon optimised oligonucleotides were designed for epitopes A (7 amino acids, PYNGKSS) and B (17 amino acids, PNDAAEQTKLYQNPTTY) for insertion into generic vectors. The sequences of epitopes A and B are of H5N1 (A/Vietnam/3028/2004).

Resulting constructs carrying either HA epitopes A or B are pGEX4T 1-VP1 S1A, pGEX4T1-VP1 S1/S3/S4 1A, pGEX4T1-VP1 S1/S3/S4 3A, pGEX4T1-VP1 S1/S3/S4 4A, pGEX4T1-VP1 SIB, pGEX4T1-VP1 S1/S3/S4 1B, pGEX4T1-VP1 S1/S3/S4 3B and pGEX4T1-VP1 S1/S3/S4 4B.

Construction of Vectors Carrying M2e:

E. coli codon optimised oligonucleotides were designed to insert M2e peptide (SLLTEVETPTRNEWECRCSDSSD; SEQ ID NO: 83) into the generic vectors.

Resulting constructs carrying M2e are designated pGEX4T1-VP1 S1M2e, pGEX4T1-VP1 S1/S3/S4 1M2e, pGEX4T1-VP1 S1/S3/S4 3M2e and pGEX4T1-VP1 S1/S3/S4 4M2e.

Construction of Vectors Carrying hM2e:

hM2e (23 amino acids) antibody is commercially available and has been shown to target the specific hM2e amino acid sequence (SLLTEVETPIRNEWGCRCNDSSD; SEQ ID NO: 84).

E. coli codon optimised oligos for hM2e were designed to insert hM2e into the generic vectors. This system is used as a proof-of-concept model since no commercial antibody against other cloned peptides is available.

Resulting constructs carrying hM2e are designated as follows pGEX4T1-VP1 S1hM2e, pGEX4T1-VP1 S1/S3/S4 1hM2e, pGEX4T1-VP1 S1/S3/S4 3hM2e and pGEX4T1-VP1 S1/S3/S4 4hM2e.

The amino acid sequence of VP1-S1 with inserted peptides from representative constructs is exemplified in FIG. 2.

Example 3

Expression and Purification GST-VP1-S1A and Assembly of VP1-S1A into Multimerically-Defined VLPs Expression VP1-S1A protein was expressed in Rosetta (DE3) pLysS (Novagen) as a glutathione-s-transferase-VP1-S1A (GST-VP1-S1A) fusion protein using the pGEX-4T-1-VP1-S1A expression vector. For solid agar medium, 15 g/L of agar was added to Luria-Bertani (LB) medium (10 g/L tryptone, 5 g/L yeast extract, 10 g/L NaCl, pH 7.0). Liquid medium used for cell cultures was Terrific Broth (TB) containing 12 g/L peptone, 24 g/L yeast extract, 0.4% (v/v) glycerol, 2.31 g/L $KH_2PO_4$ and 12.54 g/L $K_2HPO_4$. All media used were supplemented with 50 µg/mL of ampicillin and 34 µg/mL of chloramphenicol. Overnight cultures were set up by inoculating single colonies of the transformed cells into 5 mL of TB medium and cultivated at 30° C. on a rotary shaker at 180 rpm. After incubation of 16 hours, the overnight cultures were diluted 1000 times into 400 mL cultures in 2 L baffled flasks. These cultures were cultivated to an $OD_{600}$ of 0.5 at 37° C. and then cooled to 26° C. under running tap water and subsequently induced with IPTG at final concentration of 0.2 mM. The induced cultures were then cultivated at 26° C. for a further 16 hours and harvested by centrifugation at 8000 g, 4° C. for 30 mins.

Purification of VP1-S1A Capsomeres

Two pellets from 2×400 mL cultures were re-suspended in 150 mL of buffer L (200 mM NaCl, 40 mM Tris, 5 mM dithiothreitol, 1 mM EDTA, 5% v/v glycerol, pH 8 with HCl). The cell suspension was passed through a high-pressure homogenizer (Niro-Soavi) once at 1000 bar; dilution gave a final volume of 175 mL. The resulting homogenate was centrifuged at 16000 g, 4° C. for 30 mins and the supernatant which contained soluble GST-VP1-S1A was filtered through an 0.45 µm syringe filters (Millipore) giving a recovery of 135 mL.

Protein purification was performed with an Äkta Explorer system from GE Healthcare. GST-VP1-S1A in the clarified homogenate was captured using a GSTrap™ HP 5 mL column from GE Healthcare pre-equilibrated with buffer L. The bound GST-VP1-S1A was eluted with elution buffer (Buffer L with 10 mM reduced glutathione). Eluted samples were stored at −80° C. until required.

Purified thawed GST-VP1-S1A was buffer exchanged into buffer L by desalting (Desalting column 15/12, in-house packed) on the Akta Explorer system.

The eluate was pooled and loaded onto a 5 mL GSTrap™ HP column equilibrated in buffer L. Elution was achieved with elution buffer (buffer L with 10 mM reduced glutathione). Eluate (4.2 mg/mL) was stored at −80° C.

The eluate from above was thawed on ice and 8 M urea was added to a final concentration of 0.5 M (to inhibit capsomere aggregation after release from the solubilising GST tag). Thrombin (20 U/mg of GST-VP1-S1A, Sigma) was added followed by 3 hours incubation at room temperature on a roller.

500 µL of thrombin treated capsomere was injected onto a Superdex S200 10/300 GL size exclusion column (GE Healthcare) equilibrated in buffer L supplemented with 0.5 M urea, to separate capsomeres from aggregates, GST and thrombin. Capsomere fractions eluting at a volume of 10-12 mL were pooled, aliquoted and frozen at −80° C. for subsequent VLP assembly.

Assembly of Capsomeres into Multimerically-Defined VLPs

Figure 8:
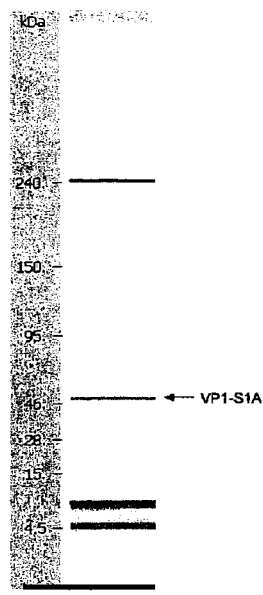
FIG. 8 Purified VP1-S1A sample after separation by size exclusion chromatography on a Superdex 200. Lower and upper bands are calibration markers introduced into the purified sample during analysis preparation (i.e. are system peaks).

The starting material after S200 separation is shown in FIG. 8. Capsomeres were assembled by dialysis against buffer 1 (0.5 M (NH$_4$)$_2$SO$_4$, 20 mM Tris, pH 7.4, 5% (v/v) glycerol, 1 mM CaCl$_2$) for 17.5 hours, and then against buffer 2 (200 mM NaCl, 20 mM Tris, pH 7.4, 5% (v/v) glycerol, 1 mM CaCl$_2$) for another 24 hours. Dialysis was at room temperature with a 10,000 MWCO dialysis membrane.

Physical Characterisation of Multimerically-Defined VLPs

Figure 9:
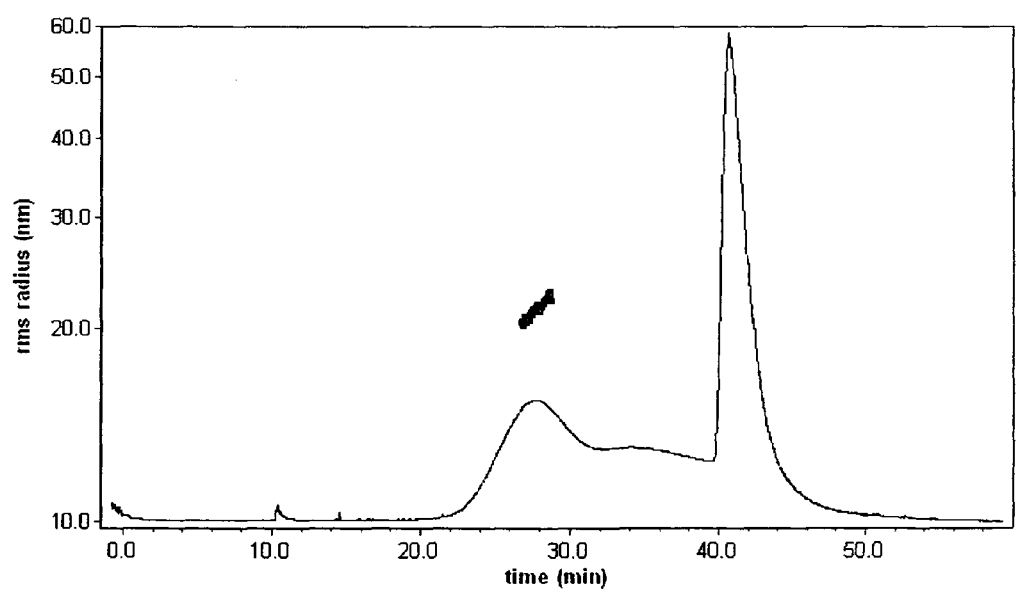
FIG. 9 AFFF plot showing assembled VLPs. X-axis is time (minutes) and Y-axis is rms radius (nm).

Assembled VLPs were analysed by both asymmetric field-flow fractionation (AFFF, Wyatt Technologies) and electron microscopy (EM). The Eclipse AFFF system purchased from Wyatt Technology Corporation. The separation channel comprised a polyetheretherketone (PEEK) lower block fitted with a stainless steel frit. The upper block was an aluminum frame to which a replaceable polycarbonate inlay was secured. The spacer used was trapezoidal with a thickness of 350 µm and a length of 26.5 cm. The breadths of the spacer near the channel inlet and outlet were 1.5 and 0.5 cm, respectively. A regenerated cellulose membrane with a molecular weight cut-off of 10 kDa was utilized as the accumulation wall. The cross-flow and injection flow rates were each monitored and regulated by a LiquiFlow device (Bronkhorst). For precise control of the focusing point, motor-driven needle valves were also used to regulate the focus and injection flows. The channel pressure was monitored by a pressure sensor, and overpressure of the channel module was prevented by means of a pressure-relief valve. Separation methods were written using the Eclipse software, which served to control the AFFF system. AFFF analysis of VLP samples were performed in GL buffer 2. The flow rate through the detectors was maintained at 0.75 mL/min during operation. A typical AFFF separation involved an initial increase of crow flow from zero to 0.75 mL/min in elution mode. The cross-flow rate was then maintained when the focusing mode was started. 100 µL of sample was then injected into the channel through the injection port at 0.2 mL/min, after which focusing was maintained for another 7 mins. To minimize the perturbations of detector signals at the switching between focusing and elution modes, a stream of bypass flow was maintained through the detectors during focusing mode at 0.75 mL/min. At the end of focusing mode, the analytes were eluted under the same cross-flow rate for 30 mins, after which the cross-flow rate was ramped down to zero to allow elution of highly retained analytes. The results of the AFFF analysis are shown in FIG. 9.

Figure 3:
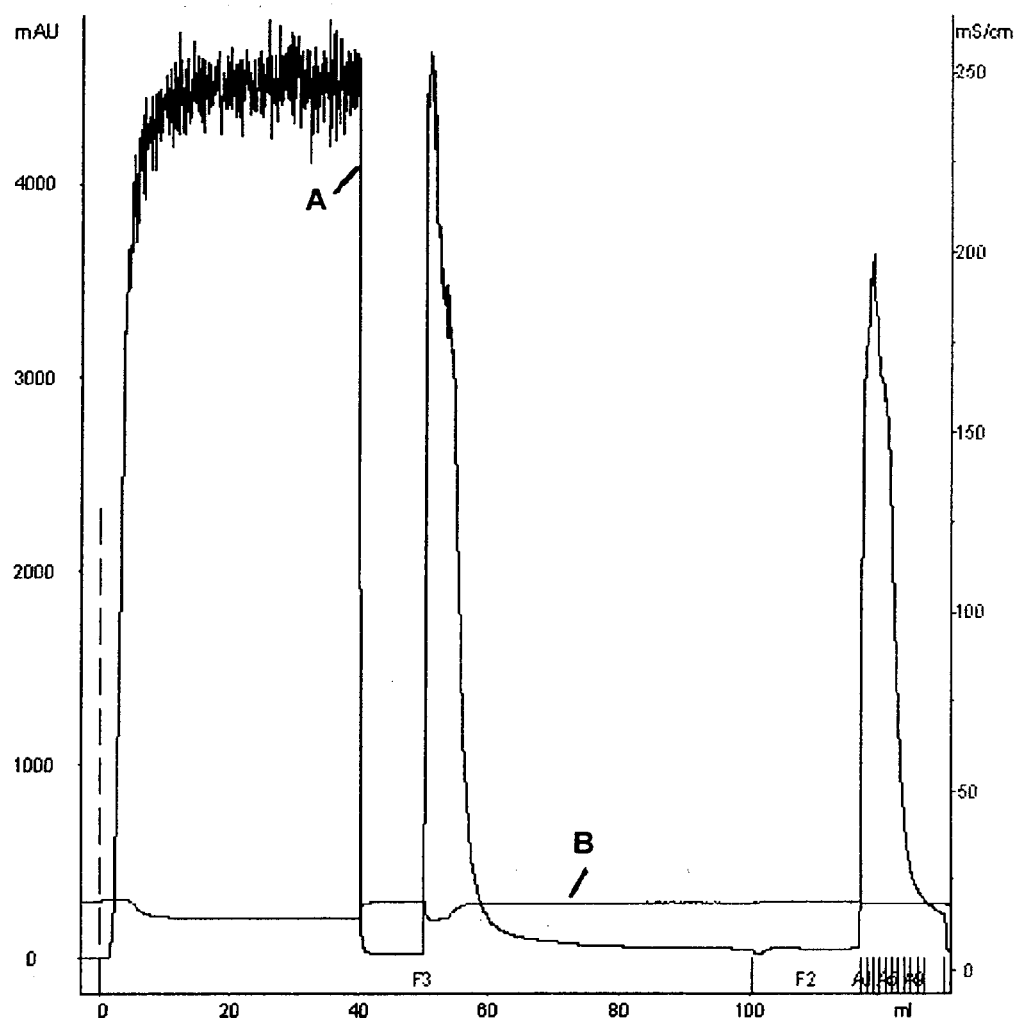
FIG. 3 Purification of GST-VP1-S1A using GSTrap HP column. X-axis is volume in ml; Y1 is absorbance in mAU; Y2 is conductivity in mS/cm. Line A represents the UV trace at 280 nm; Line B represents conductivity trace; the vertical dashed line is the injection point of sample onto the column.
Figure 4:
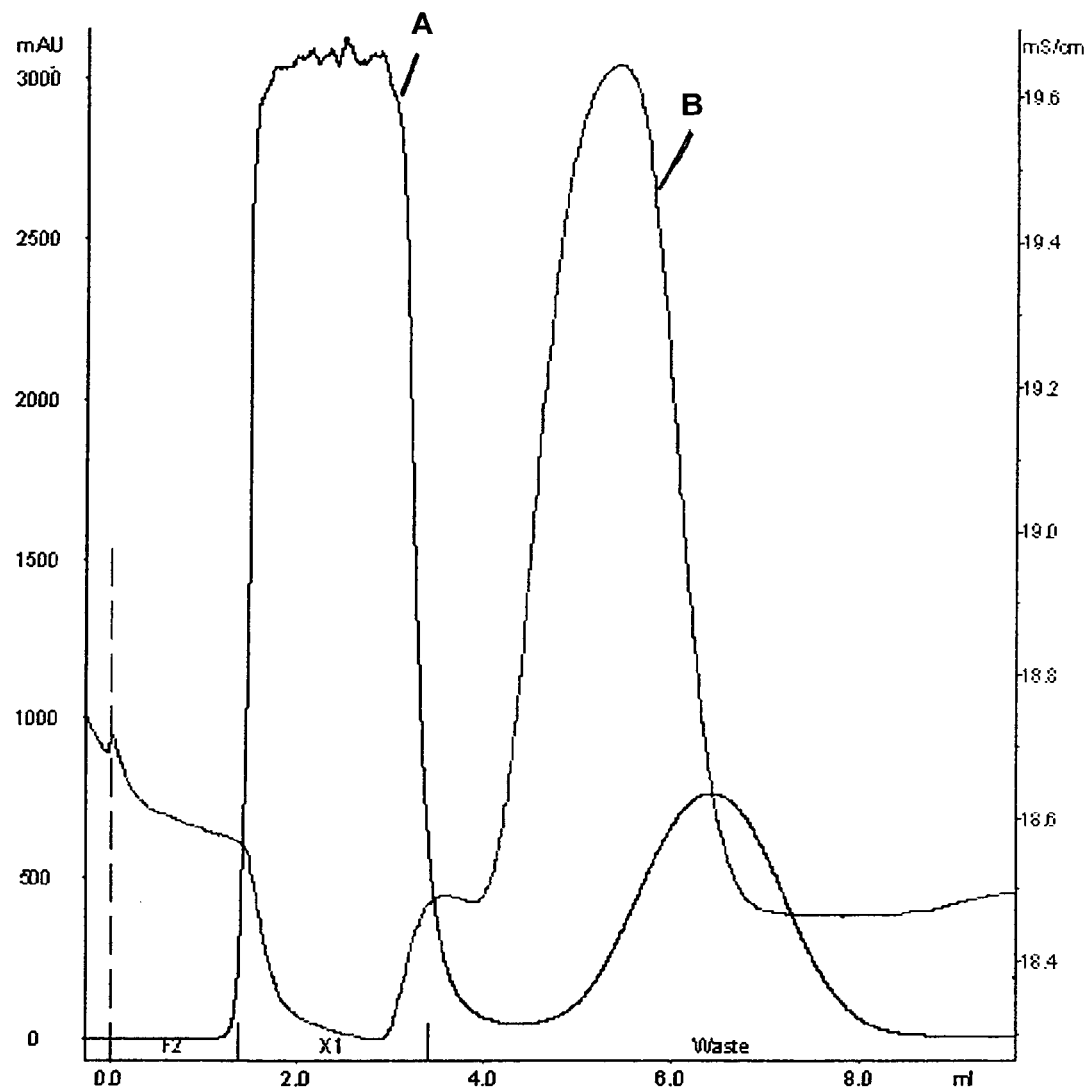
FIG. 4 Buffer exchange on a desalting column. X-axis is volume in ml; Y1 is absorbance in mAU; Y2 is conductivity in mS/cm. Line A represents the UV trace at 280 nm; Line B represents the conductivity trace; the vertical dashed line is the injection point of sample onto the column.
Figure 5:
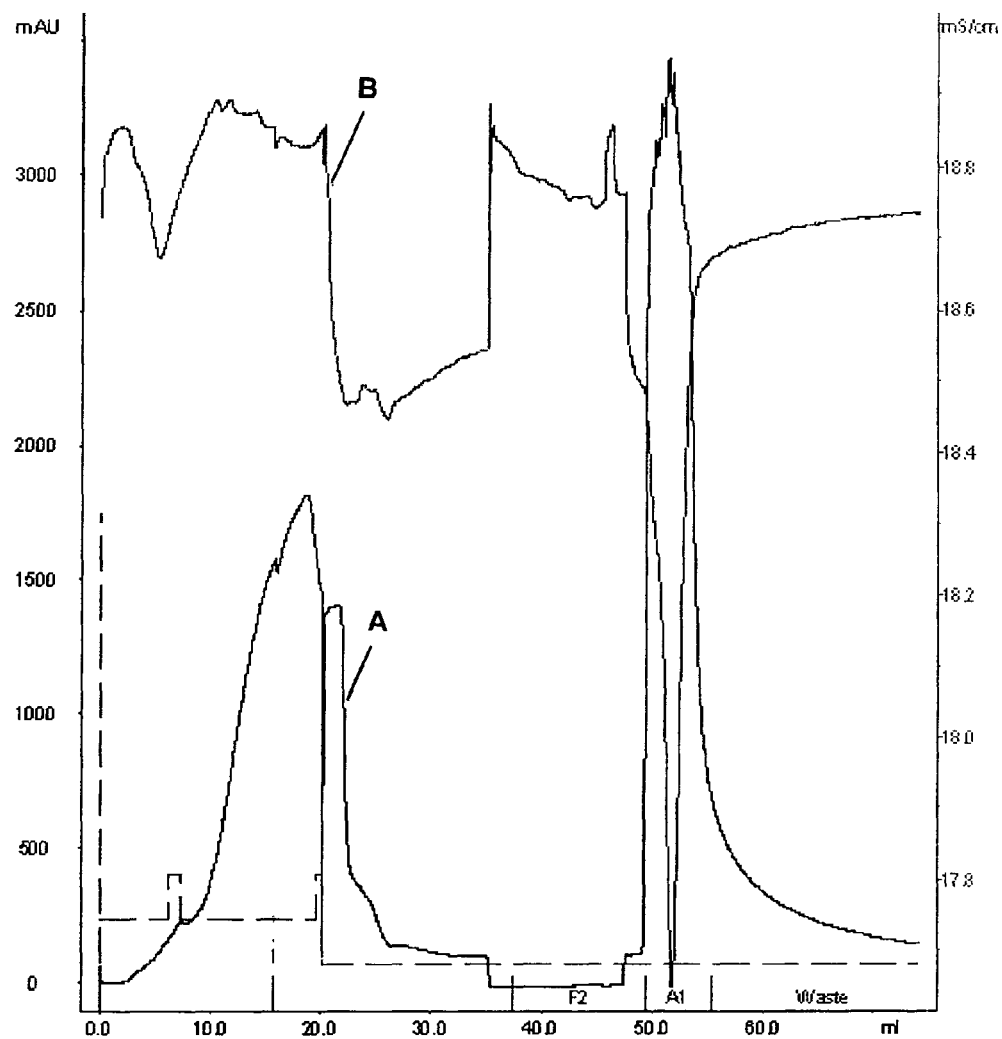
FIG. 5 Second purification of GST-VP1-S1A on GSTrap HP column. X-axis is volume in ml; Y1 is absorbance in mAU; Y2 is conductivity in mS/cm. Line A represents the UV trace at 280 nm; Line B represents the conductivity trace; the vertical dashed line is the injection point of sample onto the column; the horizontal dashed line is the P960 flow.
Figure 6:
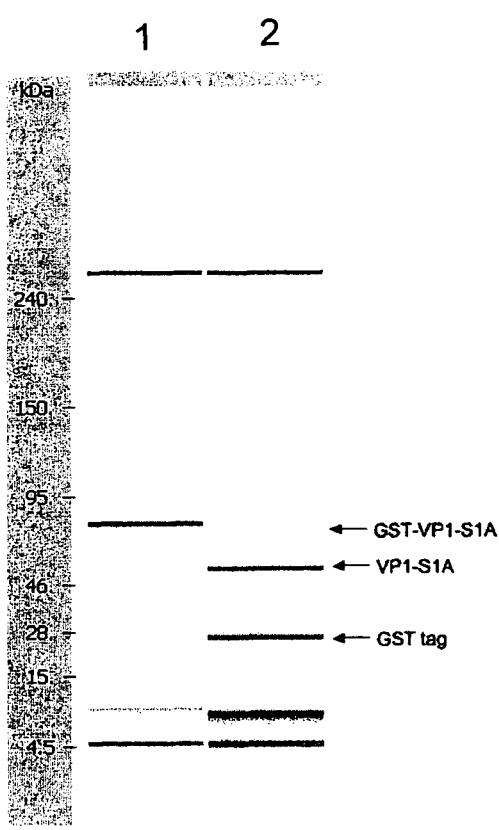
FIG. 6 Lane 1: eluate after second GST affinity purification; Lane 2: cleavage of GST tag from VP1-S1A.
Figure 7:
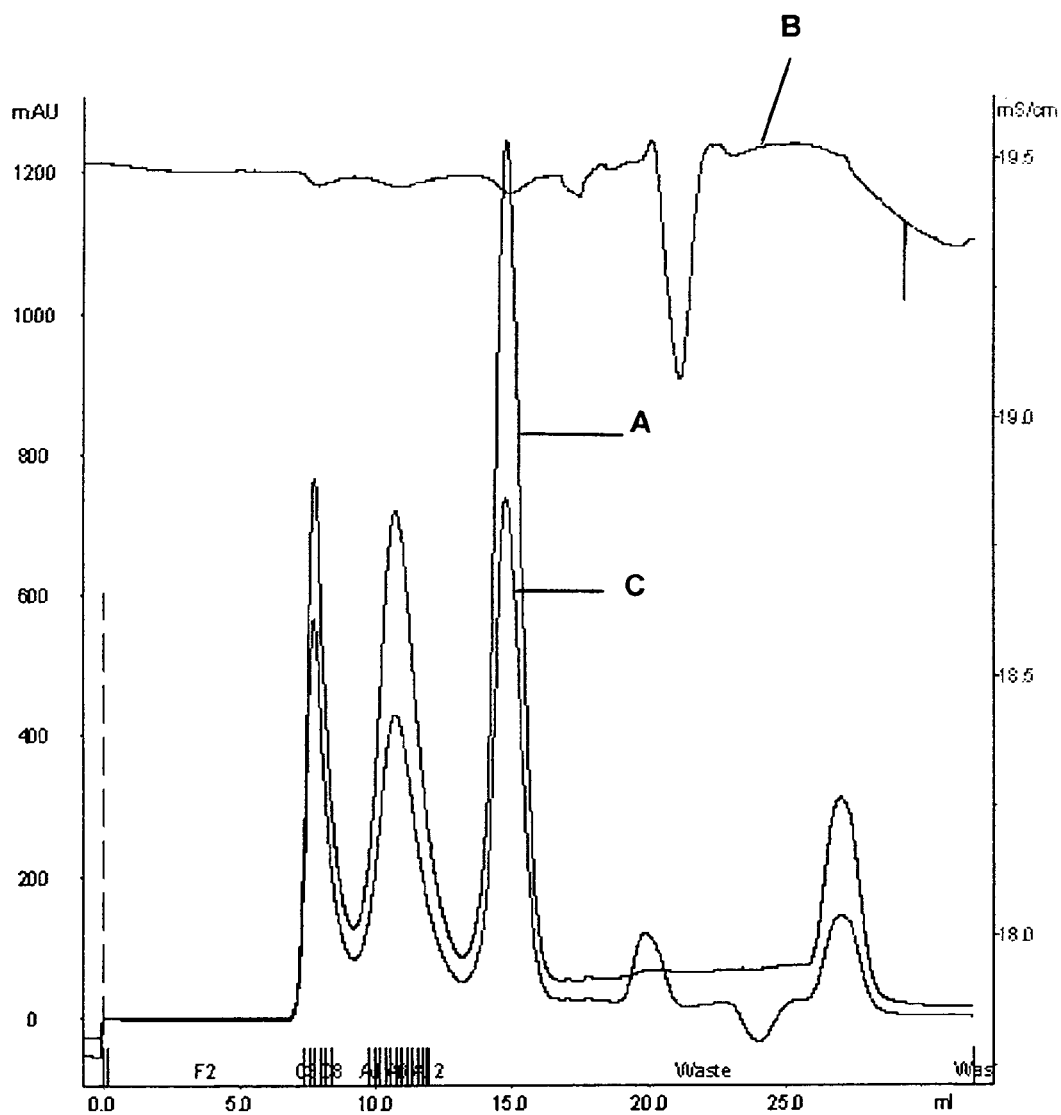
FIG. 7 Size exclusion separation on Superdex 200 to purify VP1-S1A after thrombin treatment. X-axis is volume in ml; Y1 is absorbance in mAU; Y2 is conductivity in mS/cm. Line A represents UV trace at 280 nm; Line C represents UV trace at 260 nm; line B represents the conductivity trace; the vertical dashed line is the injection point of sample onto the column.
Figure 10:
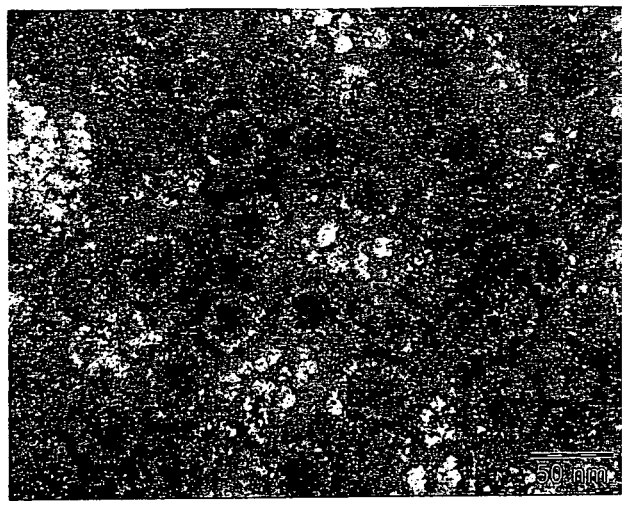
FIG. 10 Electron micrograph images showing assembled VLPs.

For EM, 2 µL of samples were applied to glow-discharged, Formvar carbon-coated grids. The remaining liquid on the grids were drained off after 2 mins, and the grids were then negatively stained with 2% uranyl acetate for 20 s. The samples on the grids were viewed under the Philips TECNAI 12 electron microscope and digital images were acquired using the integrated CCD camera and image acquisition software. EM images showing assembled VLPs are in FIG. 10. The results show that (i) protein was produced at high expression levels and purified to high homogeneity using conventional chromatographic operations and with efficient removal of the tag (FIG. 6), and (ii) this protein could be efficiently assembled into VLP structures (FIG. 10) having a size appropriate for VP1 VLPs (FIG. 9).

Example 4

Expression of VP1-S1hM2e Capsomeres and Antibody Challenge

GST-VP1-S1hM2e protein was prepared as described in example 3 for GST-VP1-S1A. Protein was purified only once by GST chromatography and stored at −80° C.

Figure 11:
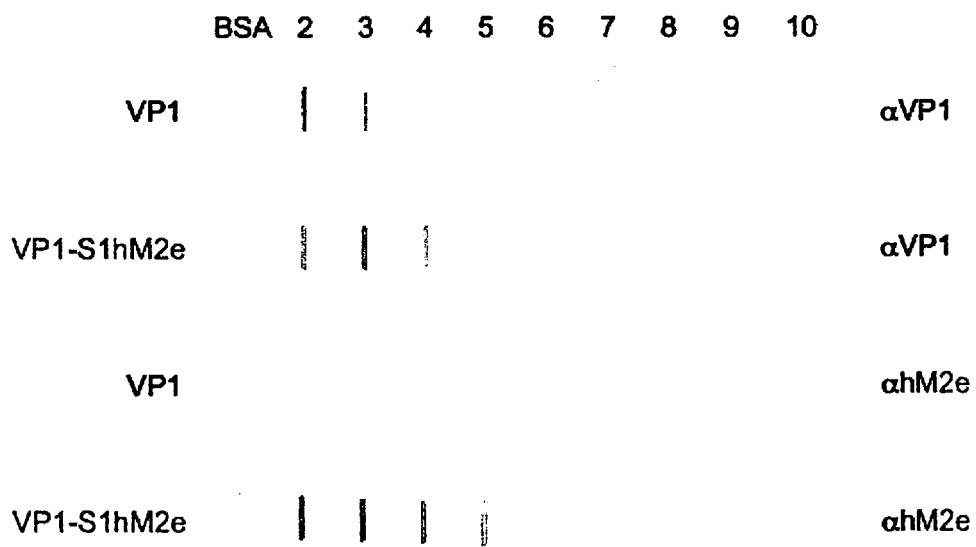
FIG. 11 Slot blot showing hM2e antibody reacting with VP1-S1hM2e capsomeres.

GST-VP1-S1hM2e protein was thawed and challenged in a slot blot with mouse monoclonal [14C2] antibody to influenza A virus M2 protein from Abcam (Cambridge, UK) recognizing the hM2e sequence inserted into S1 of VP1 (αhM2e), or else αVP1 antibody (Dr Ke An, Kansas State University). FIG. 11 shows the result of slot blot analysis. As a negative control, VP1 native VLPs (prepared by expression in baculovirus) were challenged with the same antibodies. VP1 concentrations ranged from 10 µg/ml (lane 2) to 0.1 pg/ml (lane 10) with 200 µL loaded per well. Negative control was BSA. The membrane was blocked, challenged with primary antibody, washed 3× in PBS/0.1% Tween, and challenged with secondary antibody followed by chromogenic development.

FIG. 11 shows conclusively that the antibody to the hM2e epitope recognised the chimeric VP1 containing the hM2e sequence, but did not react with the unmodified VP1 protein, suggesting that this epitope will be well presented to the immune system.

Example 5

Sequence Alignment of HA from Subtypes of Influenza Virus

A sequence alignment of HA from various strains of H5 and H3 subtypes of influenza was performed. The results of this alignment are presented in FIG. 12 and FIG. 13.
The consensus H5N1 sequence for the epitopes is:

```
A:  PYqGKSS (there is a common q <--> N and K <-->
    R variability)

B:  PNDAAEQTKLYQNPTTY (there is a common K <-->
    R variability)
```

Note the q<-->N variability in A between the consensus. There is also K<-->R variability in both A&B. All of these mutations are conservative (e.g. K<-->R preserves the charge structure). The variability between H5 types is in the A&B regions is small compared with the variability across virus variants.

Mem71 is a H3 variant. The sequence was obtained and aligned; the corresponding peptide loops are:

```
A:  KRGPqSG (there is common PgS <--> PaS
    variability)

B:  PSTNQEQTsLYVQASGR (there is common TsL <--> TNL
    variability)
```

Again the variability is conservative, although there is a lack of primary sequence consensus with H5.

Although the alignment is not presented, starting with H1N1 accession P18875, a consensus was generated by Blastp against UNIPROT and then ClustalW then CONSP. The resulting loops A and B are:

```
A:      SHKGKSS             (SEQ ID NO: 85)

B:      PSNIEDQKTIYRKENAY   (SEQ ID NO: 86)
```

Example 6

Immunization with VLPs and Challenge Experiments in Animal Model

Challenge will be intranasally with Mem71 at week 5, after vaccination at week 0 and week 3 with VP1-S1 VLPs containing inserted peptide antigen from loops A (KRGPGSG; SEQ ID NO: 81) and loops B (PSTNQEQTSLYVQASGR; SEQ ID NO: 78) of the H3 Mem71 virus.

Two doses of 3 μg of HA will be given in the form of split Mem71 virus vaccine as a positive control as this will give complete protection after two doses.

Assuming that HA is 30% of the virion, this would be the equivalent of 9 μg/dose of virus. Whole, unsplit virus is more immunogenic than split. A volume of 50 μL of VLP vaccine will be injected. The carrier VLP with no insertion will also be tested.

The challenge design is:
VLP Testing

| Mouse group | # of animals | Immunogen | Challenge (Mem71, $10^{4.5}$ pfu) |
|---|---|---|---|
| 1 | 8 | VLP 1 (H3 Peptide A (KRGPGSG) inserted into VP1-S1) | + |
| 2 | 8 | VLP 2 (H3 Peptide B PSTNQEQTSLYVQA SGR inserted into VP1-S1) | + |
| 3 | 8 | wt VLP (VP1 with no insertion) | + |
| 4 | 8 | Split Mem/Bel (3 ug/dose) | + |
| 5 | 8 | PBS | + |

Week 0

*s.c.—base of tail injection

Duration of Study: 7 weeks, continuous monitoring

Vaccination: week 0 ($1^{st}$ shot sc), week 3 ($2^{nd}$ shot sc), intranasal challenge week 5.

Mice: 40 BALB/c mice

Readouts: ELISA, HAI, and virus neutralisation assay of serum post primary and secondary vaccinations and plaque assay on lung homogenates 5 days post challenge Vaccine samples: 50 μL injected per se shot. VLPs were expressed in baculovirus, purified by sucrose and CsCl ultra-centrifugation, and dialysed into PBS. See Example 8 for experimental detail of how VLPs used as vaccine samples were prepared. Final composition was 77 μg of VLP protein and 45 μg Al(OH)$_3$ adjuvant per 50 μL dose. Endotoxin was tested to ensure acceptability.

Example 7

Construction and Sequencing of Vectors Carrying HA Loop A and Loop B of Influenza Strain H3N2 Inserted in S1 and S4 for Expression in *E. Coli* and Insect Cells FIG. 14 and FIG. 15 present two alignments. First one shows insertion of loop A and loop B in S1 of VP1 (FIG. 14), second one shows insertion of loop A and loop B in S4 of VP1 (FIG. 15).

Resulting constructs are pGEX4T1-VP1 S1H3A, pGEX4T1-VP1 S1H3B, pGEX4T1-VP1 S4H3A, and pGEX4T1-VP1 S4H3B for expression in *E. coli* and pENTR-VP1 S1H3A and pENTR-VP1 S1H3B for expression in insect cells.

Example 8

Preparation of VLPs for Challenge Experiments Using Baculovirus

The Following VLPs were Prepared for Challenge Experiments Detailed in Example 6:
VP1-H3-S1A: VP1 containing H3N2 loop A peptide inserted into the S1 site of VP1
VP1-H3-S1B: VP1 containing H3N2 loop B peptide inserted into the S1 site of VP1
VP1-wt: wild-type VP1 sequence not containing any insertion nor modification VP1 proteins for the above constructs were heterologously expressed in *Spodoptera frugiperda* (Sf9) cells infected with recombinant baculovirus encoding the chosen VP1 chimeric protein. Cells were harvested approximately 72 h postinfection, pelleted by centrifugation, and frozen at −80° C. For preparation of VLPs (all the steps were performed at 4° C.), cell pellets were resuspended in Lysis buffer (50 mM MOPS, 500 mM NaCl, 0.002% Tween 80, pH 7.0) and lysed with Branson Ultra-sonics Sonifier. Homogenized lysate was then centrifuged at 16,000×g for 30 min. The supernatant containing soluble VLPs was layered on the top of a 30% sucrose cushion and centrifuged for 1.5 h at 32000 rpm using a Beckman SW 32 Ti Rotor. The pellet was then resuspended in Lysis buffer and subjected to 15 seconds of sonication at low power setting to disperse any aggregates. Homogenate was then centrifuged at 15,000 rpm for 30 min. Clarified supernatant with CsCl added to a final concentration of 35% (wt/vol) was centrifuged at 50,000 rpm for 16 hours using a Beckman SW 60 Ti Rotor. Purified VLPs were collected by extracting the top band from the CsCl gradients. Recovered VLPs were dialyzed into PBS overnight and stored at 4° C. Protein concentration was determined by Agilent Bioanalyzer. Samples for electron microscopy were prepared as described in Example 3 and imaged at 200,000× (scale-bar 100 nm). After dialysis, VLPs in PBS were formulated with aluminium hydroxide gel (colloidal Al(OH)$_3$) to give a final dose of 50 μL consisting of 77 μg (protein equivalent) of VLP and 45 μg Al(OH)$_3$, balance PBS. FIG. 16 shows EM images of VP1-H3-S1A VLPs. FIG. 17 shows EM images of VP1-H3-S1B VLPs.

Example 9

Construction and Sequencing of Vectors Carrying HA Epitopes of Loop A and Loop B of Influenza Strain H5N1 Inserted in S4

FIG. 18 shows sequence alignment of HA loop A and loop B of influenza strain H5N1 inserted in S4 of VP1. Resulting constructs are pGEX4T1-VP1 S4A, pGEX4T1-VP1 S4B and pGEX4T1-VP1 S4hM2e.

Example 10

Expression and Purification of GST-VP1-S4A and GST-VP1-S4B and Assembly of VP1-S4A and VP1-S4B into Multimerically Defined VLPs The following VP1 variants were processed:
GST-VP1 (wild-type protein with no inserted antigen; control)
GST-VP1-S4A
GST-VP1-S4B The purpose of this example is to demonstrate that multimerically defined VLPs can be obtained using the same process used for unmodified VP1 protein, even after very different insertions (A or B) into site S4 of VP1.

In this example, "A" in the above constructs refers to antigenic peptide taken from influenza virus H5N1 corresponding to loop A in the HA protein, as in example 2 (7 amino acids, PYNGKSS). "B" in the above constructs refers to antigenic peptide taken from influenza virus H5N1 corresponding to loop B in the HA protein, as in example 2 (17 amino acids, PNDAAEQTKLYQNPTTY).

For each construct, protein was expressed as described in Example 2.

For purification of each construct, a pellet from 800 mL of culture was re-suspended in 40 mL of buffer L (200 mM NaCl, 40 mM Tris, 1 mM EDTA, 5 mM dithiothreitol, 5% v/v glycerol, pH 8 with HCl). The cell suspension was passed through a high-pressure homogenizer (Niro-Soavi) once at 1000 bar. The homogenate was diluted with L buffer and centrifuged. Supernatant containing soluble VP1 fusion protein was filtered through two 0.45 µm syringe filters (Millipore), giving a recovery of 100-125 mL per construct examined. Protein purification was performed with an Äkta Explorer system from GE Healthcare. 100 mL of filtered homogenate containing the selected GST-VP1 fusion protein (listed above) was loaded onto a GSTrap™ HP 5 mL column from GE Healthcare pre-equilibrated with buffer L (FIGS. 19A and B). The bound GST-VP1 fusion protein was eluted with elution buffer (Buffer L with 10 mM reduced glutathione). Eluted fractions of 250 µL were stored at −80° C. until required.

The eluate from above was thawed on ice and thrombin (50 U/mL, Sigma) was added followed by 2 h incubation at room temperature on a roller. 200 µL of thrombin-treated capsomere was injected onto a Superdex S200 10/300 GL size exclusion column (GE Healthcare) equilibrated in buffer L, to separate capsomeres from aggregates, GST and thrombin (FIGS. 20A and B). Capsomere fractions (150 µL) were assembled by dialysis against buffer 1 (0.5 M $(NH_4)_2SO_4$, 20 mM Tris, pH 7.4, 5% (v/v) glycerol, 1 mM $CaCl_2$) for 17 h, and then against buffer 2 (200 mM NaCl, 20 mM Tris, pH 7.4, 5% (v/v) glycerol, 1 mM $CaCl_2$) for another 24 hours. Dialysis was at room temperature with a 10,000 MWCO dialysis membrane.

Comparison of GST-VP1 with GST-VP1-S4A and GST-VP1-S4B by Bioanalyzer analysis is shown in FIG. 21.

Assembled VLPs were analysed by both asymmetric field-flow fractionation (AFFF, Wyatt Technologies) (FIG. 22) and electron microscopy (EM) as described in Example 3 (see FIGS. 23 A, B and C).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

---

SEQUENCE LISTING

```
<160> NUMBER OF SEQ ID NOS: 145

<210> SEQ ID NO 1
<211> LENGTH: 7
<212> TYPE: PRT
<213> ORGANISM: Influenza A virus

<400> SEQUENCE: 1

Pro Tyr Asn Gly Lys Ser Ser
1               5

<210> SEQ ID NO 2
<211> LENGTH: 7
<212> TYPE: PRT
<213> ORGANISM: Influenza A virus

<400> SEQUENCE: 2

Ser Tyr Leu Gly Lys Pro Ser
1               5

<210> SEQ ID NO 3
<211> LENGTH: 7
<212> TYPE: PRT
<213> ORGANISM: Influenza A virus

<400> SEQUENCE: 3

Pro Tyr Leu Gly Lys Ser Ser
1               5

<210> SEQ ID NO 4
<211> LENGTH: 7
<212> TYPE: PRT
```

<213> ORGANISM: Influenza A virus

<400> SEQUENCE: 4

Pro Tyr Gln Gly Arg Ser Ser
1               5

<210> SEQ ID NO 5
<211> LENGTH: 7
<212> TYPE: PRT
<213> ORGANISM: Influenza A virus

<400> SEQUENCE: 5

Pro Tyr Gln Gly Lys Ser Ser
1               5

<210> SEQ ID NO 6
<211> LENGTH: 7
<212> TYPE: PRT
<213> ORGANISM: Influenza A virus

<400> SEQUENCE: 6

Pro Tyr Gln Gly Lys Ser Ser
1               5

<210> SEQ ID NO 7
<211> LENGTH: 7
<212> TYPE: PRT
<213> ORGANISM: Influenza A virus

<400> SEQUENCE: 7

Pro Tyr Asn Gly Lys Ser Ser
1               5

<210> SEQ ID NO 8
<211> LENGTH: 7
<212> TYPE: PRT
<213> ORGANISM: Influenza A virus

<400> SEQUENCE: 8

Pro Tyr Gln Gly Lys Pro Ser
1               5

<210> SEQ ID NO 9
<211> LENGTH: 7
<212> TYPE: PRT
<213> ORGANISM: Influenza A virus

<400> SEQUENCE: 9

Pro Tyr His Gly Arg Ser Ser
1               5

<210> SEQ ID NO 10
<211> LENGTH: 7
<212> TYPE: PRT
<213> ORGANISM: Influenza A virus

<400> SEQUENCE: 10

Pro Tyr Gln Gly Ser Pro Ser
1               5

<210> SEQ ID NO 11
<211> LENGTH: 7
<212> TYPE: PRT
<213> ORGANISM: Influenza A virus

<400> SEQUENCE: 11

```
Pro Tyr Gln Gly Lys Pro Ser
1               5

<210> SEQ ID NO 12
<211> LENGTH: 7
<212> TYPE: PRT
<213> ORGANISM: Influenza A virus

<400> SEQUENCE: 12

Pro Tyr Leu Gly Lys Pro Ser
1               5

<210> SEQ ID NO 13
<211> LENGTH: 7
<212> TYPE: PRT
<213> ORGANISM: Influenza A virus

<400> SEQUENCE: 13

Pro Tyr Leu Gly Lys Pro Ser
1               5

<210> SEQ ID NO 14
<211> LENGTH: 7
<212> TYPE: PRT
<213> ORGANISM: Influenza A virus

<400> SEQUENCE: 14

Pro Tyr Gln Gly Asn Pro Ser
1               5

<210> SEQ ID NO 15
<211> LENGTH: 7
<212> TYPE: PRT
<213> ORGANISM: Influenza A virus

<400> SEQUENCE: 15

Pro Tyr Gln Gly Lys Ser Ser
1               5

<210> SEQ ID NO 16
<211> LENGTH: 7
<212> TYPE: PRT
<213> ORGANISM: Influenza A virus

<400> SEQUENCE: 16

Pro Tyr Gln Gly Lys Ser Ser
1               5

<210> SEQ ID NO 17
<211> LENGTH: 7
<212> TYPE: PRT
<213> ORGANISM: Influenza A virus

<400> SEQUENCE: 17

Pro Tyr Gln Gly Lys Ser Ser
1               5

<210> SEQ ID NO 18
<211> LENGTH: 7
<212> TYPE: PRT
<213> ORGANISM: Influenza A virus

<400> SEQUENCE: 18

Pro Tyr Gln Gly Lys Ser Ser
1               5
```

```
<210> SEQ ID NO 19
<211> LENGTH: 7
<212> TYPE: PRT
<213> ORGANISM: Influenza A virus

<400> SEQUENCE: 19

Pro Tyr Gln Gly Arg Ser Ser
1               5

<210> SEQ ID NO 20
<211> LENGTH: 7
<212> TYPE: PRT
<213> ORGANISM: Influenza A virus

<400> SEQUENCE: 20

Pro Tyr Gln Gly Arg Ser Ser
1               5

<210> SEQ ID NO 21
<211> LENGTH: 7
<212> TYPE: PRT
<213> ORGANISM: Influenza A virus

<400> SEQUENCE: 21

Pro Tyr Gln Gly Arg Ser Ser
1               5

<210> SEQ ID NO 22
<211> LENGTH: 7
<212> TYPE: PRT
<213> ORGANISM: Influenza A virus

<400> SEQUENCE: 22

Pro Tyr Gln Gly Arg Ser Ser
1               5

<210> SEQ ID NO 23
<211> LENGTH: 7
<212> TYPE: PRT
<213> ORGANISM: Influenza A virus

<400> SEQUENCE: 23

Pro Tyr Gln Gly Arg Ser Ser
1               5

<210> SEQ ID NO 24
<211> LENGTH: 17
<212> TYPE: PRT
<213> ORGANISM: Influenza A virus

<400> SEQUENCE: 24

Pro Asn Asp Ala Ala Glu Gln Thr Lys Leu Tyr Gln Asn Pro Ile Thr
1               5                   10                  15

Tyr

<210> SEQ ID NO 25
<211> LENGTH: 17
<212> TYPE: PRT
<213> ORGANISM: Influenza A virus

<400> SEQUENCE: 25

Pro Asn Asp Glu Ala Glu Gln Ile Lys Ile Tyr Gln Asn Pro Thr Thr
1               5                   10                  15
```

Tyr

<210> SEQ ID NO 26
<211> LENGTH: 17
<212> TYPE: PRT
<213> ORGANISM: Influenza A virus

<400> SEQUENCE: 26

Pro Asn Asp Ala Ala Glu Gln Ile Lys Leu Tyr Gln Asn Pro Thr Thr
1               5                   10                  15

Tyr

<210> SEQ ID NO 27
<211> LENGTH: 17
<212> TYPE: PRT
<213> ORGANISM: Influenza A virus

<400> SEQUENCE: 27

Pro Asn Asp Ala Ala Glu Gln Thr Arg Leu Tyr Gln Asn Pro Thr Thr
1               5                   10                  15

Tyr

<210> SEQ ID NO 28
<211> LENGTH: 17
<212> TYPE: PRT
<213> ORGANISM: Influenza A virus

<400> SEQUENCE: 28

Pro Asn Asp Ala Ala Glu Gln Thr Lys Leu Tyr Gln Asn Pro Thr Thr
1               5                   10                  15

Tyr

<210> SEQ ID NO 29
<211> LENGTH: 17
<212> TYPE: PRT
<213> ORGANISM: Influenza A virus

<400> SEQUENCE: 29

Pro Asn Asp Ala Ala Glu Gln Thr Lys Leu Tyr Gln Asn Pro Thr Thr
1               5                   10                  15

Tyr

<210> SEQ ID NO 30
<211> LENGTH: 17
<212> TYPE: PRT
<213> ORGANISM: Influenza A virus

<400> SEQUENCE: 30

Pro Asn Asp Ala Ala Glu Gln Thr Arg Leu Tyr Gln Asn Pro Ile Thr
1               5                   10                  15

Tyr

<210> SEQ ID NO 31
<211> LENGTH: 17
<212> TYPE: PRT
<213> ORGANISM: Influenza A virus

<400> SEQUENCE: 31

Pro Asn Asp Ala Ala Glu Gln Thr Lys Leu Tyr Gln Asn Pro Thr Thr
1               5                   10                  15

Tyr

<210> SEQ ID NO 32
<211> LENGTH: 17
<212> TYPE: PRT
<213> ORGANISM: Influenza A virus

<400> SEQUENCE: 32

Pro Asn Asp Ala Ala Glu Gln Thr Lys Leu Tyr Gln Asn Pro Thr Thr
1               5                   10                  15

Tyr

<210> SEQ ID NO 33
<211> LENGTH: 17
<212> TYPE: PRT
<213> ORGANISM: Influenza A virus

<400> SEQUENCE: 33

Pro Asn Asp Ala Ala Glu Gln Thr Lys Leu Tyr Gln Asn Pro Thr Thr
1               5                   10                  15

Tyr

<210> SEQ ID NO 34
<211>

```
<211> LENGTH: 17
<212> TYPE: PRT
<213> ORGANISM: Influenza A virus

<400> SEQUENCE: 38

Pro Asn Asp Ala Ala Glu Gln Thr Lys Leu Tyr Gln Asn Pro Thr Thr
1               5                   10                  15

Tyr

<210> SEQ ID NO 39
<211> LENGTH: 17
<212> TYPE: PRT
<213> ORGANISM: Influenza A virus

<400> SEQUENCE: 39

Pro Asn Asp Ala Ala Glu Gln Thr Lys Leu Tyr Gln Asn Pro Thr Thr
1               5                   10                  15

Tyr

<210> SEQ ID NO 40
<211> LENGTH: 17
<212> TYPE: PRT
<213> ORGANISM: Influenza A virus

<400> SEQUENCE: 40

Pro Asn Asp Ala Ala Glu Gln Thr Lys Leu Tyr Gln Asn Pro Thr Thr
1               5                   10                  15

Tyr

<210> SEQ ID NO 41
<211> LENGTH: 17
<212> TYPE: PRT
<213> ORGANISM: Influenza A virus

<400> SEQUENCE: 41

Pro Asn Asp Ala Ala Glu Gln Thr Lys Leu Tyr Gln Asn Pro Thr Thr
1               5                   10                  15

Tyr

<210> SEQ ID NO 42
<211> LENGTH: 17
<212> TYPE: PRT
<213> ORGANISM: Influenza A virus

<400> SEQUENCE: 42

Pro Asn Asp Ala Ala Glu Gln Thr Arg Leu Tyr Gln Asn Pro Thr Thr
1               5                   10                  15

Tyr

<210> SEQ ID NO 43
<211> LENGTH: 17
<212> TYPE: PRT
<213> ORGANISM: Influenza A virus

<400> SEQUENCE: 43

Pro Asn Asp Ala Ala Glu Gln Thr Arg Leu Tyr Gln Asn Pro Thr Thr
1               5                   10                  15

Tyr

<210> SEQ ID NO 44
<211> LENGTH: 17
<212> TYPE: PRT
```

<213> ORGANISM: Influenza A virus

<400> SEQUENCE: 44

Pro Asn Asp Ala Ala Glu Gln Thr Arg Leu Tyr Gln Asn Pro Thr Thr
1               5                   10                  15

Tyr

<210> SEQ ID NO 45
<211> LENGTH: 17
<212> TYPE: PRT
<213> ORGANISM: Influenza A virus

<400> SEQUENCE: 45

Pro Asn Asp Ala Ala Glu Gln Thr Arg Leu Tyr Gln Asn Pro Thr Thr
1               5                   10                  15

Tyr

<210> SEQ ID NO 46
<211> LENGTH: 17
<212> TYPE: PRT
<213> ORGANISM: Influenza A virus

<400> SEQUENCE: 46

Pro Asn Asp Ala Ala Glu Gln Thr Arg Leu Tyr Gln Asn Pro Thr Thr
1               5                   10                  15

Tyr

<210> SEQ ID NO 47
<211> LENGTH: 7
<212> TYPE: PRT
<213> ORGANISM: Influenza A virus

<400> SEQUENCE: 47

Lys Arg Gly Ser Val Lys Ser
1               5

<210> SEQ ID NO 48
<211> LENGTH: 7
<212> TYPE: PRT
<213> ORGANISM: Influenza A virus

<400> SEQUENCE: 48

Lys Arg Gly Pro Gly Ser Gly
1               5

<210> SEQ ID NO 49
<211> LENGTH: 7
<212> TYPE: PRT
<213> ORGANISM: Influenza A virus

<400> SEQUENCE: 49

Lys Arg Gly Pro Gly Ser Gly
1               5

<210> SEQ ID NO 50
<211> LENGTH: 7
<212> TYPE: PRT
<213> ORGANISM: Influenza A virus

<400> SEQUENCE: 50

Lys Arg Gly Pro Gly Ser Gly
1               5

<210> SEQ ID NO 51
<211> LENGTH: 7
<212> TYPE: PRT
<213> ORGANISM: Influenza A virus

<400> SEQUENCE: 51

Lys Arg Gly Pro Asp Ser Gly
1               5

<210> SEQ ID NO 52
<211> LENGTH: 7
<212> TYPE: PRT
<213> ORGANISM: Influenza A virus

<400> SEQUENCE: 52

Lys Arg Arg Ser Asn Lys Ser
1               5

<210> SEQ ID NO 53
<211> LENGTH: 7
<212> TYPE: PRT
<213> ORGANISM: Influenza A virus

<400> SEQUENCE: 53

Lys Arg Gly Ser Val Asn Ser
1               5

<210> SEQ ID NO 54
<211> LENGTH: 7
<212> TYPE: PRT
<213> ORGANISM: Influenza A virus

<400> SEQUENCE: 54

Lys Arg Gly Ser Val Lys Ser
1               5

<210> SEQ ID NO 55
<211> LENGTH: 7
<212> TYPE: PRT
<213> ORGANISM: Influenza A virus

<400> SEQUENCE: 55

Lys Arg Gly Ser Asp Asn Ser
1               5

<210> SEQ ID NO 56
<211> LENGTH: 7
<212> TYPE: PRT
<213> ORGANISM: Influenza A virus

<400> SEQUENCE: 56

Lys Arg Gly Ser Val Lys Ser
1               5

<210> SEQ ID NO 57
<211> LENGTH: 7
<212> TYPE: PRT
<213> ORGANISM: Influenza A virus

<400> SEQUENCE: 57

Lys Arg Gly Ser Val Lys Ser
1               5

<210> SEQ ID NO 58
<211> LENGTH: 7
<212> TYPE: PRT

<213> ORGANISM: Influenza A virus

<400> SEQUENCE: 58

Lys Arg Arg Ser Ile Lys Ser
1               5

<210> SEQ ID NO 59
<211> LENGTH: 7
<212> TYPE: PRT
<213> ORGANISM: Influenza A virus

<400> SEQUENCE: 59

Lys Arg Gly Ser Val Asn Ser
1               5

<210> SEQ ID NO 60
<211> LENGTH: 7
<212> TYPE: PRT
<213> ORGANISM: Influenza A virus

<400> SEQUENCE: 60

Lys Arg Gly Pro Asp Ser Gly
1               5

<210> SEQ ID NO 61
<211> LENGTH: 17
<212> TYPE: PRT
<213> ORGANISM: Influenza A virus

<400> SEQUENCE: 61

Pro Ser Thr Asp Arg Glu Gln Thr Lys Leu Tyr Val Arg Ala Ser Gly
1               5                   10                  15

Arg

<210> SEQ ID NO 62
<211> LENGTH: 17
<212> TYPE: PRT
<213> ORGANISM: Influenza A virus

<400> SEQUENCE: 62

Pro Ser Thr Asn Gln Glu Gln Thr Ser Leu Tyr Val Gln Ala Ser Gly
1               5                   10                  15

Arg

<210> SEQ ID NO 63
<211> LENGTH: 17
<212> TYPE: PRT
<213> ORGANISM: Influenza A virus

<400> SEQUENCE: 63

Pro Ser Thr Asn Gln Glu Gln Thr Ser Leu Tyr Val Gln Ala Ser Gly
1               5                   10                  15

Arg

<210> SEQ ID NO 64
<211> LENGTH: 17
<212> TYPE: PRT
<213> ORGANISM: Influenza A virus

<400> SEQUENCE: 64

Pro Ser Thr Asn Gln Glu Gln Thr Ser Leu Tyr Val Gln Ala Ser Gly
1               5                   10                  15

Arg

-continued

```
<210> SEQ ID NO 65
<211> LENGTH: 17
<212> TYPE: PRT
<213> ORGANISM: Influenza A virus

<400> SEQUENCE: 65

Pro Ser Thr Asp Gln Glu Gln Thr Ser Leu Tyr Val Gln Ala Ser Gly
1               5                   10                  15
Arg

<210> SEQ ID NO 66
<211> LENGTH: 17
<212> TYPE: PRT
<213> ORGANISM: Influenza A virus

<400> SEQUENCE: 66

Pro Ser Thr Asp Ser Asp Gln Ile Ser Ile Tyr Ala Gln Ala Ser Gly
1               5                   10                  15
Arg

<210> SEQ ID NO 67
<211> LENGTH: 17
<212> TYPE: PRT
<213> ORGANISM: Influenza A virus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 67

Pro Xaa Thr Glu Lys Glu Gln Thr Asn Leu Tyr Val Arg Ala Ser Gly
1               5                   10                  15
Arg

<210> SEQ ID NO 68
<211> LENGTH: 17
<212> TYPE: PRT
<213> ORGANISM: Influenza A virus

<400> SEQUENCE: 68

Pro Ser Thr Asp Arg Glu Gln Thr Asn Leu Tyr Val Arg Ala Ser Gly
1               5                   10                  15
Arg

<210> SEQ ID NO 69
<211> LENGTH: 17
<212> TYPE: PRT
<213> ORGANISM: Influenza A virus

<400> SEQUENCE: 69

Pro Ser Thr Asp Lys Glu Gln Thr Lys Leu Tyr Val Arg Ala Ser Gly
1               5                   10                  15
Arg

<210> SEQ ID NO 70
<211> LENGTH: 17
<212> TYPE: PRT
<213> ORGANISM: Influenza A virus

<400> SEQUENCE: 70

Pro Ser Thr Asp Arg Asp Gln Thr Ser Leu Tyr Val Gln Ala Ser Gly
1               5                   10                  15
```

Arg

<210> SEQ ID NO 71
<211> LENGTH: 17
<212> TYPE: PRT
<213> ORGANISM: Influenza A virus

<400> SEQUENCE: 71

Pro Ser Thr Asp Arg Asp Gln Thr Ser Leu Tyr Val Gln Ala Ser Gly
1               5                   10                  15

Arg

<210> SEQ ID NO 72
<211> LENGTH: 17
<212> TYPE: PRT
<213> ORGANISM: Influenza A virus

<400> SEQUENCE: 72

Pro Ser Thr Asp Ser Asp Gln Thr Ser Leu Tyr Ala Gln Ala Ser Gly
1               5                   10                  15

Arg

<210> SEQ ID NO 73
<211> LENGTH: 17
<212> TYPE: PRT
<213> ORGANISM: Influenza A virus

<400> SEQUENCE: 73

Pro Ser Thr Asp Ser Asp Gln Thr Ser Leu Tyr Val Gln Ala Ser Gly
1               5                   10                  15

Arg

<210> SEQ ID NO 74
<211> LENGTH: 17
<212> TYPE: PRT
<213> ORGANISM: Influenza A virus

<400> SEQUENCE: 74

Pro Ser Thr Asp Gln Glu Gln Thr Ser Leu Tyr Val Gln Ala Ser Gly
1               5                   10                  15

Arg

<210> SEQ ID NO 75
<211> LENGTH: 7
<212> TYPE: PRT
<213> ORGANISM: Influenza A virus

<400> SEQUENCE: 75

Pro Tyr Gln Gly Lys Ser Ser
1               5

<210> SEQ ID NO 76
<211> LENGTH: 17
<212> TYPE: PRT
<213> ORGANISM: Influenza A virus

<400> SEQUENCE: 76

Pro Asn Asp Ala Ala Glu Gln Thr Lys Leu Tyr Gln Asn Pro Thr Thr
1               5                   10                  15

Tyr

```
<210> SEQ ID NO 77
<211> LENGTH: 7
<212> TYPE: PRT
<213> ORGANISM: Influenza A virus

<400> SEQUENCE: 77

Lys Arg Gly Pro Gly Ser Gly
1               5

<210> SEQ ID NO 78
<211> LENGTH: 17
<212> TYPE: PRT
<213> ORGANISM: Influenza A virus

<400> SEQUENCE: 78

Pro Ser Thr Asn Gln Glu Gln Thr Ser Leu Tyr Val Gln Ala Ser Gly
1               5                   10                  15

Arg

<210> SEQ ID NO 79
<211> LENGTH: 7
<212> TYPE: PRT
<213> ORGANISM: Influenza A virus

<400> SEQUENCE: 79

Ser His Lys Gly Lys Ser Ser
1               5

<210> SEQ ID NO 80
<211> LENGTH: 17
<212> TYPE: PRT
<213> ORGANISM: Influenza A virus

<400> SEQUENCE: 80

Pro Ser Asn Ile Glu Asp Gln Lys Thr Ile Tyr Arg Lys Glu Asn Ala
1               5                   10                  15

Tyr

<210> SEQ ID NO 81
<211> LENGTH: 7
<212> TYPE: PRT
<213> ORGANISM: Influenza A virus

<400> SEQUENCE: 81

Pro Tyr Asn Gly Lys Ser Ser
1               5

<210> SEQ ID NO 82
<211> LENGTH: 7
<212> TYPE: PRT
<213> ORGANISM: Influenza A virus

<400> SEQUENCE: 82

Lys Arg Gly Pro Gly Ser Gly
1               5

<210> SEQ ID NO 83
<211> LENGTH: 23
<212> TYPE: PRT
<213> ORGANISM: Influenza A virus

<400> SEQUENCE: 83

Ser Leu Leu Thr Glu Val Glu Thr Pro Thr Arg Asn Glu Trp Glu Cys
1               5                   10                  15
```

-continued

```
Arg Cys Ser Asp Ser Ser Asp
            20

<210> SEQ ID NO 84
<211> LENGTH: 23
<212> TYPE: PRT
<213> ORGANISM: Influenza A virus

<400> SEQUENCE: 84

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 85
<211> LENGTH: 7
<212> TYPE: PRT
<213> ORGANISM: Influenza A virus

<400> SEQUENCE: 85

Ser His Lys Gly Lys Ser Ser
1               5

<210> SEQ ID NO 86
<211> LENGTH: 17
<212> TYPE: PRT
<213> ORGANISM: Influenza A virus

<400> SEQUENCE: 86

Pro Ser Asn Ile Glu Asp Gln Lys Thr Ile Tyr Arg Lys Glu Asn Ala
1               5                   10                  15

Tyr

<210> SEQ ID NO 87
<211> LENGTH: 384
<212> TYPE: PRT
<213> ORGANISM: Polyomavirus sp

<400> SEQUENCE: 87

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
```

```
                    165                 170                 175
Gly Leu Val Thr Asp Ala Arg Thr Lys Tyr Lys Glu Glu Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Asn Tyr Asp Val His His Trp Arg Gly Leu Pro
    290                 295                 300

Arg Tyr Phe Lys Ile Thr Leu Arg Lys Arg Trp Val Lys Asn Pro Tyr
305                 310                 315                 320

Pro Met Ala Ser Leu Ile Ser Ser Leu Phe Asn Asn Met Leu Pro Gln
                325                 330                 335

Val Gln Gly Gln Pro Met Glu Gly Glu Asn Thr Gln Val Glu Glu Val
            340                 345                 350

Arg Val Tyr Asp Gly Thr Glu Pro Val Pro Gly Asp Pro Asp Met Thr
        355                 360                 365

Arg Tyr Val Asp Arg Phe Gly Lys Thr Lys Thr Val Phe Pro Gly Asn
    370                 375                 380

<210> SEQ ID NO 88
<211> LENGTH: 385
<212> TYPE: PRT
<213> ORGANISM: Polyomavirus sp

<400> SEQUENCE: 88

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Gly Thr Glu Asp Ser Pro Gly Asn Asn Thr
                85                  90                  95

Leu Pro Thr Trp Ser Met Ala Lys Leu Gln Leu Pro Met Leu Asn Glu
            100                 105                 110

Asp Leu Thr Cys Asp Thr Leu Gln Met Trp Glu Ala Val Ser Val Lys
        115                 120                 125

Thr Glu Val Val Gly Ser Gly Ser Leu Leu Asp Val His Gly Phe Asn
    130                 135                 140

Lys Pro Thr Asp Thr Val Asn Thr Lys Gly Ile Ser Thr Pro Val Glu
145                 150                 155                 160

Gly Ser Gln Tyr His Val Phe Ala Val Gly Gly Glu Pro Leu Asp Leu
```

```
                    165                 170                 175
Gln Gly Leu Val Thr Asp Ala Arg Thr Lys Tyr Lys Glu Glu Gly Val
                180                 185                 190

Val Thr Ile Lys Thr Ile Thr Lys Lys Asp Met Val Asn Lys Asp Gln
            195                 200                 205

Val Leu Asn Pro Ile Ser Lys Ala Lys Leu Asp Lys Asp Gly Met Tyr
        210                 215                 220

Pro Val Glu Ile Trp His Pro Asp Pro Ala Lys Asn Glu Asn Thr Arg
225                 230                 235                 240

Tyr Phe Gly Asn Tyr Thr Gly Gly Thr Thr Pro Pro Val Leu Gln
                245                 250                 255

Phe Thr Asn Thr Leu Thr Thr Val Leu Leu Asp Glu Asn Gly Val Gly
            260                 265                 270

Pro Leu Cys Lys Gly Glu Gly Leu Tyr Leu Ser Cys Val Asp Ile Met
        275                 280                 285

Gly Trp Arg Val Thr Arg Asn Tyr Asp Val His His Trp Arg Gly Leu
                290                 295                 300

Pro Arg Tyr Phe Lys Ile Thr Leu Arg Lys Arg Trp Val Lys Asn Pro
305                 310                 315                 320

Tyr Pro Met Ala Ser Leu Ile Ser Ser Leu Phe Asn Asn Met Leu Pro
                325                 330                 335

Gln Val Gln Gly Gln Pro Met Glu Gly Glu Asn Thr Gln Val Glu Glu
            340                 345                 350

Val Arg Val Tyr Asp Gly Thr Glu Pro Val Pro Gly Asp Pro Asp Met
        355                 360                 365

Thr Arg Tyr Val Asp Arg Phe Gly Lys Thr Lys Thr Val Phe Pro Gly
        370                 375                 380

Asn
385

<210> SEQ ID NO 89
<211> LENGTH: 385
<212> TYPE: PRT
<213> ORGANISM: Polyomavirus sp

<400> SEQUENCE: 89

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
```

```
                145                 150                 155                 160
Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
                180                 185                 190

Thr Ile Lys Thr Ile Thr Lys Lys Asp Met Val Asn Lys Asp Gln Val
                195                 200                 205

Leu Asn Pro Ile Ser Lys Ala Lys Leu Asp Lys Asp Gly Met Tyr Pro
            210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Ser Ala Tyr Asp Val His His Trp Arg Gly Leu
    290                 295                 300

Pro Arg Tyr Phe Lys Ile Thr Leu Arg Lys Arg Trp Val Lys Asn Pro
305                 310                 315                 320

Tyr Pro Met Ala Ser Leu Ile Ser Ser Leu Phe Asn Asn Met Leu Pro
                325                 330                 335

Gln Val Gln Gly Gln Pro Met Glu Gly Glu Asn Thr Gln Val Glu Glu
            340                 345                 350

Val Arg Val Tyr Asp Gly Thr Glu Pro Val Pro Gly Asp Pro Asp Met
        355                 360                 365

Thr Arg Tyr Val Asp Arg Phe Gly Lys Thr Lys Thr Val Phe Pro Gly
    370                 375                 380

Asn
385

<210> SEQ ID NO 90
<211> LENGTH: 385
<212> TYPE: PRT
<213> ORGANISM: Polyomavirus sp

<400> SEQUENCE: 90

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
                20                  25                  30

Gly Gly Met Glu Val Leu Asp Leu Val Thr Gly Pro Asp Ser Val Thr
            35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
                100                 105                 110

Leu Thr Cys Asp Thr Leu Gln Met Trp Glu Ala Val Ser Val Lys Thr
            115                 120                 125

Glu Val Val Gly Ser Gly Ser Leu Leu Asp Val His Gly Phe Asn Lys
```

```
            130                 135                 140
Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr His Val Thr Pro Pro Val Leu Gln
                245                 250                 255

Phe Thr Asn Thr Leu Thr Thr Val Leu Leu Asp Glu Asn Gly Val Gly
            260                 265                 270

Pro Leu Cys Lys Gly Glu Gly Leu Tyr Leu Ser Cys Val Asp Ile Met
        275                 280                 285

Gly Trp Arg Val Thr Arg Asn Tyr Asp Val His His Trp Arg Gly Leu
    290                 295                 300

Pro Arg Tyr Phe Lys Ile Thr Leu Arg Lys Arg Trp Val Lys Asn Pro
305                 310                 315                 320

Tyr Pro Met Ala Ser Leu Ile Ser Ser Leu Phe Asn Asn Met Leu Pro
                325                 330                 335

Gln Val Gln Gly Gln Pro Met Glu Gly Glu Asn Thr Gln Val Glu Glu
            340                 345                 350

Val Arg Val Tyr Asp Gly Thr Glu Pro Val Pro Gly Asp Pro Asp Met
        355                 360                 365

Thr Arg Tyr Val Asp Arg Phe Gly Lys Thr Lys Thr Val Phe Pro Gly
    370                 375                 380

Asn
385

<210> SEQ ID NO 91
<211> LENGTH: 387
<212> TYPE: PRT
<213> ORGANISM: Polyomavirus sp

<400> SEQUENCE: 91

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Gly Thr Glu Asp Ser Pro Gly Asn Asn Thr
                85                  90                  95

Leu Pro Thr Trp Ser Met Ala Lys Leu Gln Leu Pro Met Leu Asn Glu
            100                 105                 110

Asp Leu Thr Cys Asp Thr Leu Gln Met Trp Glu Ala Val Ser Val Lys
```

```
                115                 120                 125
Thr Glu Val Val Gly Ser Gly Ser Leu Leu Asp Val His Gly Phe Asn
            130                 135                 140
Lys Pro Thr Asp Thr Val Asn Thr Lys Gly Ile Ser Thr Pro Val Glu
145                 150                 155                 160
Gly Ser Gln Tyr His Val Phe Ala Val Gly Gly Glu Pro Leu Asp Leu
                165                 170                 175
Gln Gly Leu Val Thr Asp Ala Arg Thr Lys Tyr Lys Glu Glu Gly Val
            180                 185                 190
Val Thr Ile Lys Thr Ile Thr Lys Lys Asp Met Val Asn Lys Asp Gln
            195                 200                 205
Val Leu Asn Pro Ile Ser Lys Ala Lys Leu Asp Lys Asp Gly Met Tyr
            210                 215                 220
Pro Val Glu Ile Trp His Pro Asp Pro Ala Lys Asn Glu Asn Thr Arg
225                 230                 235                 240
Tyr Phe Gly Asn Tyr Thr Gly Gly Thr His Val Thr Pro Pro Val Leu
                245                 250                 255
Gln Phe Thr Asn Thr Leu Thr Thr Val Leu Leu Asp Glu Asn Gly Val
            260                 265                 270
Gly Pro Leu Cys Lys Gly Glu Gly Leu Tyr Leu Ser Cys Val Asp Ile
            275                 280                 285
Met Gly Trp Arg Val Thr Arg Ser Ala Tyr Asp Val His His Trp Arg
            290                 295                 300
Gly Leu Pro Arg Tyr Phe Lys Ile Thr Leu Arg Lys Arg Trp Val Lys
305                 310                 315                 320
Asn Pro Tyr Pro Met Ala Ser Leu Ile Ser Ser Leu Phe Asn Asn Met
                325                 330                 335
Leu Pro Gln Val Gln Gly Gln Pro Met Glu Gly Glu Asn Thr Gln Val
            340                 345                 350
Glu Glu Val Arg Val Tyr Asp Gly Thr Glu Pro Val Pro Gly Asp Pro
            355                 360                 365
Asp Met Thr Arg Tyr Val Asp Arg Phe Gly Lys Thr Lys Thr Val Phe
            370                 375                 380
Pro Gly Asn
385

<210> SEQ ID NO 92
<211> LENGTH: 402
<212> TYPE: PRT
<213> ORGANISM: Polyomavirus sp

<400> SEQUENCE: 92

Met Ala Pro Lys Arg Lys Ser Gly Val Ser Lys Cys Glu Thr Lys Cys
1               5                   10                  15
Thr Lys Ala Cys Pro Arg Pro Ala Pro Val Pro Lys Leu Leu Ile Lys
            20                  25                  30
Gly Gly Met Glu Val Leu Asp Leu Val Thr Gly Pro Asp Ser Val Thr
        35                  40                  45
Glu Ile Glu Ala Phe Leu Asn Pro Arg Met Gly Gln Pro Pro Thr Pro
    50                  55                  60
Glu Ser Leu Thr Glu Gly Gly Gln Tyr Tyr Gly Trp Ser Arg Gly Ile
65                  70                  75                  80
Asn Leu Ala Thr Ser Ala Pro Asn Asp Ala Ala Glu Gln Thr Lys Leu
                85                  90                  95
Tyr Gln Asn Pro Thr Thr Tyr Gly Thr Glu Asp Ser Pro Gly Asn Asn
```

```
                      100                 105                 110
Thr Leu Pro Thr Trp Ser Met Ala Lys Leu Gln Leu Pro Met Leu Asn
            115                 120                 125

Glu Asp Leu Thr Cys Asp Thr Leu Gln Met Trp Glu Ala Val Ser Val
130                 135                 140

Lys Thr Glu Val Val Gly Ser Gly Leu Leu Asp Val His Gly Phe
145                 150                 155                 160

Asn Lys Pro Thr Asp Thr Val Asn Thr Lys Gly Ile Ser Thr Pro Val
            165                 170                 175

Glu Gly Ser Gln Tyr His Val Phe Ala Val Gly Gly Glu Pro Leu Asp
        180                 185                 190

Leu Gln Gly Leu Val Thr Asp Ala Arg Thr Lys Tyr Lys Glu Glu Gly
    195                 200                 205

Val Val Thr Ile Lys Thr Ile Thr Lys Lys Asp Met Val Asn Lys Asp
210                 215                 220

Gln Val Leu Asn Pro Ile Ser Lys Ala Lys Leu Asp Lys Asp Gly Met
225                 230                 235                 240

Tyr Pro Val Glu Ile Trp His Pro Asp Pro Ala Lys Asn Glu Asn Thr
                245                 250                 255

Arg Tyr Phe Gly Asn Tyr Thr Gly Gly Thr Thr Thr Pro Pro Val Leu
            260                 265                 270

Gln Phe Thr Asn Thr Leu Thr Thr Val Leu Leu Asp Glu Asn Gly Val
        275                 280                 285

Gly Pro Leu Cys Lys Gly Glu Gly Leu Tyr Leu Ser Cys Val Asp Ile
    290                 295                 300

Met Gly Trp Arg Val Thr Arg Asn Tyr Asp Val His His Trp Arg Gly
305                 310                 315                 320

Leu Pro Arg Tyr Phe Lys Ile Thr Leu Arg Lys Arg Trp Val Lys Asn
                325                 330                 335

Pro Tyr Pro Met Ala Ser Leu Ile Ser Ser Leu Phe Asn Asn Met Leu
            340                 345                 350

Pro Gln Val Gln Gly Gln Pro Met Glu Gly Glu Asn Thr Gln Val Glu
        355                 360                 365

Glu Val Arg Val Tyr Asp Gly Thr Glu Pro Val Pro Gly Asp Pro Asp
    370                 375                 380

Met Thr Arg Tyr Val Asp Arg Phe Gly Lys Thr Lys Thr Val Phe Pro
385                 390                 395                 400

Gly Asn

<210> SEQ ID NO 93
<211> LENGTH: 392
<212> TYPE: PRT
<213> ORGANISM: Polyomavirus sp

<400> SEQUENCE: 93

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80
```

Asn Leu Ala Thr Ser Ala Pro Tyr Asn Gly Lys Ser Ser Gly Thr Glu
                85                  90                  95

Asp Ser Pro Gly Asn Asn Thr Leu Pro Thr Trp Ser Met Ala Lys Leu
            100                 105                 110

Gln Leu Pro Met Leu Asn Glu Asp Leu Thr Cys Asp Thr Leu Gln Met
        115                 120                 125

Trp Glu Ala Val Ser Val Lys Thr Glu Val Val Gly Ser Gly Ser Leu
130                 135                 140

Leu Asp Val His Gly Phe Asn Lys Pro Thr Asp Thr Val Asn Thr Lys
145                 150                 155                 160

Gly Ile Ser Thr Pro Val Gly Ser Gln Tyr His Val Phe Ala Val
                165                 170                 175

Gly Gly Glu Pro Leu Asp Leu Gln Gly Leu Val Thr Asp Ala Arg Thr
            180                 185                 190

Lys Tyr Lys Glu Glu Gly Val Val Thr Ile Lys Thr Ile Thr Lys Lys
        195                 200                 205

Asp Met Val Asn Lys Asp Gln Val Leu Asn Pro Ile Ser Lys Ala Lys
210                 215                 220

Leu Asp Lys Asp Gly Met Tyr Pro Val Glu Ile Trp His Pro Asp Pro
225                 230                 235                 240

Ala Lys Asn Glu Asn Thr Arg Tyr Phe Gly Asn Tyr Thr Gly Gly Thr
                245                 250                 255

Thr Thr Pro Pro Val Leu Gln Phe Thr Asn Thr Leu Thr Thr Val Leu
            260                 265                 270

Leu Asp Glu Asn Gly Val Gly Pro Leu Cys Lys Gly Glu Gly Leu Tyr
        275                 280                 285

Leu Ser Cys Val Asp Ile Met Gly Trp Arg Val Thr Arg Asn Tyr Asp
290                 295                 300

Val His His Trp Arg Gly Leu Pro Arg Tyr Phe Lys Ile Thr Leu Arg
305                 310                 315                 320

Lys Arg Trp Val Lys Asn Pro Tyr Pro Met Ala Ser Leu Ile Ser Ser
                325                 330                 335

Leu Phe Asn Asn Met Leu Pro Gln Val Gln Gly Gln Pro Met Glu Gly
            340                 345                 350

Glu Asn Thr Gln Val Glu Glu Val Arg Val Tyr Asp Gly Thr Glu Pro
        355                 360                 365

Val Pro Gly Asp Pro Asp Met Thr Arg Tyr Val Asp Arg Phe Gly Lys
370                 375                 380

Thr Lys Thr Val Phe Pro Gly Asn
385                 390

<210> SEQ ID NO 94
<211> LENGTH: 408
<212> TYPE: PRT
<213> ORGANISM: Polyomavirus sp

<400> SEQUENCE: 94

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Ser Leu Leu Thr Glu Val Glu Thr Pro Thr
            85                  90                  95

Arg Asn Glu Trp Glu Cys Arg Cys Ser Asp Ser Ser Asp Gly Thr Glu
            100                 105                 110

Asp Ser Pro Gly Asn Asn Thr Leu Pro Thr Trp Ser Met Ala Lys Leu
            115                 120                 125

Gln Leu Pro Met Leu Asn Glu Asp Leu Thr Cys Asp Thr Leu Gln Met
            130                 135                 140

Trp Glu Ala Val Ser Val Lys Thr Glu Val Val Gly Ser Gly Ser Leu
145                 150                 155                 160

Leu Asp Val His Gly Phe Asn Lys Pro Thr Asp Thr Val Asn Thr Lys
                165                 170                 175

Gly Ile Ser Thr Pro Val Glu Gly Ser Gln Tyr His Val Phe Ala Val
                180                 185                 190

Gly Gly Glu Pro Leu Asp Leu Gln Gly Leu Val Thr Asp Ala Arg Thr
                195                 200                 205

Lys Tyr Lys Glu Glu Gly Val Val Thr Ile Lys Thr Ile Thr Lys Lys
210                 215                 220

Asp Met Val Asn Lys Asp Gln Val Leu Asn Pro Ile Ser Lys Ala Lys
225                 230                 235                 240

Leu Asp Lys Asp Gly Met Tyr Pro Val Glu Ile Trp His Pro Asp Pro
                245                 250                 255

Ala Lys Asn Glu Asn Thr Arg Tyr Phe Gly Asn Tyr Thr Gly Gly Thr
                260                 265                 270

Thr Thr Pro Pro Val Leu Gln Phe Thr Asn Thr Leu Thr Thr Val Leu
                275                 280                 285

Leu Asp Glu Asn Gly Val Gly Pro Leu Cys Lys Gly Glu Gly Leu Tyr
                290                 295                 300

Leu Ser Cys Val Asp Ile Met Gly Trp Arg Val Thr Arg Asn Tyr Asp
305                 310                 315                 320

Val His His Trp Arg Gly Leu Pro Arg Tyr Phe Lys Ile Thr Leu Arg
                325                 330                 335

Lys Arg Trp Val Lys Asn Pro Tyr Pro Met Ala Ser Leu Ile Ser Ser
                340                 345                 350

Leu Phe Asn Asn Met Leu Pro Gln Val Gln Gly Gln Pro Met Glu Gly
                355                 360                 365

Glu Asn Thr Gln Val Glu Glu Val Arg Val Tyr Asp Gly Thr Glu Pro
                370                 375                 380

Val Pro Gly Asp Pro Asp Met Thr Arg Tyr Val Asp Arg Phe Gly Lys
385                 390                 395                 400

Thr Lys Thr Val Phe Pro Gly Asn
                405

<210> SEQ ID NO 95
<211> LENGTH: 408
<212> TYPE: PRT
<213> ORGANISM: Polyomavirus sp

<400> SEQUENCE: 95

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
            35                  40                  45

Glu Ile Glu Ala Phe Leu Asn Pro Arg Met Gly Gln Pro Pro Thr Pro
 50                  55                  60

Glu Ser Leu Thr Glu Gly Gly Gln Tyr Tyr Gly Trp Ser Arg Gly Ile
 65                  70                  75                  80

Asn Leu Ala Thr Ser Ala Ser Leu Leu Thr Glu Val Glu Thr Pro Ile
                85                  90                  95

Arg Asn Glu Trp Gly Cys Arg Cys Asn Asp Ser Ser Asp Gly Thr Glu
            100                 105                 110

Asp Ser Pro Gly Asn Asn Thr Leu Pro Thr Trp Ser Met Ala Lys Leu
            115                 120                 125

Gln Leu Pro Met Leu Asn Glu Asp Leu Thr Cys Asp Thr Leu Gln Met
            130                 135                 140

Trp Glu Ala Val Ser Val Lys Thr Glu Val Val Gly Ser Gly Ser Leu
145                 150                 155                 160

Leu Asp Val His Gly Phe Asn Lys Pro Thr Asp Thr Val Asn Thr Lys
                165                 170                 175

Gly Ile Ser Thr Pro Val Glu Gly Ser Gln Tyr His Val Phe Ala Val
                180                 185                 190

Gly Gly Glu Pro Leu Asp Leu Gln Gly Leu Val Thr Asp Ala Arg Thr
            195                 200                 205

Lys Tyr Lys Glu Glu Gly Val Val Thr Ile Lys Thr Ile Thr Lys Lys
210                 215                 220

Asp Met Val Asn Lys Asp Gln Val Leu Asn Pro Ile Ser Lys Ala Lys
225                 230                 235                 240

Leu Asp Lys Asp Gly Met Tyr Pro Val Glu Ile Trp His Pro Asp Pro
                245                 250                 255

Ala Lys Asn Glu Asn Thr Arg Tyr Phe Gly Asn Tyr Thr Gly Gly Thr
            260                 265                 270

Thr Thr Pro Pro Val Leu Gln Phe Thr Asn Thr Leu Thr Thr Val Leu
            275                 280                 285

Leu Asp Glu Asn Gly Val Gly Pro Leu Cys Lys Gly Glu Gly Leu Tyr
290                 295                 300

Leu Ser Cys Val Asp Ile Met Gly Trp Arg Val Thr Arg Asn Tyr Asp
305                 310                 315                 320

Val His His Trp Arg Gly Leu Pro Arg Tyr Phe Lys Ile Thr Leu Arg
                325                 330                 335

Lys Arg Trp Val Lys Asn Pro Tyr Pro Met Ala Ser Leu Ile Ser Ser
            340                 345                 350

Leu Phe Asn Asn Met Leu Pro Gln Val Gln Gly Gln Pro Met Glu Gly
            355                 360                 365

Glu Asn Thr Gln Val Glu Glu Val Arg Val Tyr Asp Gly Thr Glu Pro
            370                 375                 380

Val Pro Gly Asp Pro Asp Met Thr Arg Tyr Val Asp Arg Phe Gly Lys
385                 390                 395                 400

Thr Lys Thr Val Phe Pro Gly Asn
                405

<210> SEQ ID NO 96
<211> LENGTH: 568
<212> TYPE: PRT
<213> ORGANISM: Influenza A virus

<400> SEQUENCE: 96

```
Met Glu Arg Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Ala
            20                  25                  30

Asp Thr Ile Met Glu Lys Asn Val Thr Val Thr His Ala Gln Asn Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Glu Ala Ser
    130                 135                 140

Ser Gly Val Arg Ser Ala Cys Pro Tyr Asn Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Ile Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Arg Ala Ile Asp Gly Val Thr Asn Lys Val Asn Ser
385                 390                 395                 400

Ile Ile Gly Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
```

```
                   420                 425                 430
Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Arg Tyr Ser Glu Glu Ala
            500                 505                 510

Arg Leu Asn Arg Glu Glu Ile Ser Gly Val Lys Leu Glu Ser Met Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 97
<211> LENGTH: 568
<212> TYPE: PRT
<213> ORGANISM: Influenza A virus

<400> SEQUENCE: 97

Met Glu Arg Ile Val Leu Leu Ala Ile Ile Gly Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asn Pro Asp Gly Val Lys
    50                  55                  60

Pro Leu Ile Leu Lys Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Gly Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Gly Ala Ser
    130                 135                 140

Ser Gly Val Ser Ser Ala Cys Ser Tyr Leu Gly Lys Pro Ser Phe Phe
145                 150                 155                 160

Arg Asn Val Val Trp Leu Ile Lys Lys Asn Asn Thr Tyr Pro Pro Ile
                165                 170                 175

Lys Val Ser Tyr Asn Asn Thr Asn Gln Glu Asp Leu Leu Val Leu Trp
            180                 185                 190

Gly Ile His His Pro Asn Asp Glu Ala Glu Gln Ile Lys Ile Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
```

```
                225                 230                 235                 240
Arg Met Glu Phe Phe Trp Thr Ile Leu Lys Pro Asn Asp Ala Ile Asn
                    245                 250                 255
Phe Asp Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
            275                 280                 285
Asn Cys Asn Thr Lys Cys Gln Thr Pro Met Gly Ala Ile Asn Ser Ser
        290                 295                 300
Met Pro Phe His Asn Ile His Pro Leu Thr Val Gly Glu Cys Pro Lys
305                 310                 315                 320
Tyr Val Lys Ser Asn Arg Leu Val Leu Ala Thr Gly Leu Arg Asn Ala
                325                 330                 335
Pro Gln Arg Glu Gly Gly Arg Lys Lys Arg Gly Leu Phe Gly Ala Ile
                340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Lys
            370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
                420                 425                 430
Gly Phe Leu Asp Val Trp Thr Tyr Asn Ala Glu Leu Leu Val Leu Met
            435                 440                 445
Glu Asn Glu Arg Thr Leu Asp Phe His Asp Ser Asn Val Lys Asn Leu
        450                 455                 460
Tyr Glu Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Lys Asn Gly Thr Tyr Asp Tyr Pro Gln Tyr Ser Glu Glu Ala
                500                 505                 510
Arg Leu Asn Arg Glu Glu Ile Ser Gly Val Lys Leu Glu Ser Met Gly
            515                 520                 525
Thr Tyr Gln Ile Leu Ser Ile Tyr Ser Thr Val Ala Ser Ser Leu Ala
        530                 535                 540
Leu Ala Ile Met Val Ala Gly Leu Ser Leu Trp Met Cys Ser Asn Gly
545                 550                 555                 560
Ser Leu Gln Cys Arg Ile Cys Ile
                565

<210> SEQ ID NO 98
<211> LENGTH: 568
<212> TYPE: PRT
<213> ORGANISM: Influenza A virus

<400> SEQUENCE: 98

Met Glu Gly Thr Val Leu Leu Leu Ala Ile Ile Ser Leu Val Lys Ser
1               5                   10                  15
Asp Gln Ile Cys Ile Gly Tyr His Ala Asn Asn Ser Thr Glu Gln Val
            20                  25                  30
Asp Thr Ile Met Glu Lys Asn Val Thr Val Thr His Ala Gln Asp Ile
```

```
            35                  40                  45
Leu Glu Lys Thr His Asn Gly Lys Leu Cys Asp Leu Asp Gly Val Lys
 50                  55                  60
Pro Leu Ile Leu Arg Asp Cys Ser Val Ala Gly Trp Leu Leu Gly Asn
 65                  70                  75                  80
Pro Met Cys Asp Glu Phe Ile Asn Val Pro Glu Trp Ser Tyr Ile Val
                 85                  90                  95
Glu Lys Ala Ser Pro Ala Asn Asp Leu Cys Tyr Pro Gly Asp Phe Asn
                100                 105                 110
Asp Tyr Glu Glu Leu Lys His Leu Leu Ser Arg Ile Asn His Phe Glu
                115                 120                 125
Lys Ile Gln Ile Ile Pro Lys Ser Ser Trp Ser Asn His Glu Ala Ser
130                 135                 140
Ser Gly Val Ser Ser Ala Cys Pro Tyr Leu Gly Lys Ser Ser Phe Phe
145                 150                 155                 160
Arg Asn Val Val Trp Leu Ile Lys Lys Asn Ser Ala Tyr Pro Thr Ile
                165                 170                 175
Lys Arg Ser Tyr Asn Asn Thr Asn Gln Glu Asp Leu Leu Val Leu Trp
                180                 185                 190
Gly Ile His His Pro Asn Asp Ala Ala Glu Gln Ile Lys Leu Tyr Gln
                195                 200                 205
Asn Pro Thr Thr Tyr Ile Ser Val Gly Thr Ser Thr Leu Asn Gln Arg
                210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
                275                 280                 285
Asn Cys Asn Thr Lys Cys Gln Thr Pro Met Gly Ala Ile Asn Ser Ser
290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Thr
                325                 330                 335
Pro Gln Arg Glu Arg Arg Lys Lys Arg Gly Leu Phe Gly Ala Ile
                340                 345                 350
Ala Gly Phe Ile Glu Gly Gly Trp Gln Gly Met Val Asp Gly Trp Tyr
                355                 360                 365
Gly Tyr His His Ser Asn Glu Gln Gly Ser Gly Tyr Ala Ala Asp Lys
                370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
                420                 425                 430
Gly Phe Leu Asp Val Trp Thr Tyr Asn Ala Glu Leu Leu Val Leu Met
                435                 440                 445
Glu Asn Glu Arg Thr Leu Asp Phe His Asp Ser Asn Val Lys Asn Leu
450                 455                 460
```

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
            485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Met Gly
            515                 520                 525

Thr Tyr Gln Ile Leu Ser Ile Tyr Ser Thr Val Val Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
            565

<210> SEQ ID NO 99
<211> LENGTH: 568
<212> TYPE: PRT
<213> ORGANISM: Influenza A virus

<400> SEQUENCE: 99

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
            195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
                275                 280                 285

Asn Cys Asn Thr Lys Cys Gln Thr Pro Ile Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
                515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 100
<211> LENGTH: 568
<212> TYPE: PRT
<213> ORGANISM: Influenza A virus

<400> SEQUENCE: 100

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
                35                  40                  45

Leu Glu Lys Thr His Asn Gly Lys Leu Cys Asp Leu Asp Gly Val Lys
            50                  55                  60

Pro Leu Ile Leu Arg Asp Cys Ser Val Ala Gly Trp Leu Leu Gly Asn
65                  70                  75                  80

```
Pro Met Cys Asp Glu Phe Ile Asn Val Pro Glu Trp Ser Tyr Ile Val
                85                  90                  95
Glu Lys Ala Asn Pro Val Asn Asp Leu Cys Tyr Pro Gly Asp Phe Asn
            100                 105                 110
Asp Tyr Glu Glu Leu Lys His Leu Leu Ser Arg Ile Asn His Phe Glu
        115                 120                 125
Lys Ile Gln Ile Ile Pro Lys Ser Ser Trp Ser Ser His Glu Ala Ser
    130                 135                 140
Leu Gly Val Ser Ser Ala Cys Pro Tyr Gln Gly Lys Ser Ser Phe Phe
145                 150                 155                 160
Arg Asn Val Val Trp Leu Ile Lys Lys Asn Ser Thr Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Lys Leu Tyr Gln
        195                 200                 205
Asn Pro Thr Thr Tyr Ile Ser Val Gly Thr Ser Thr Leu Asn Gln Arg
    210                 215                 220
Leu Val Pro Arg Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
            260                 265                 270
Val Lys Lys Gly Asp Ser Thr Ile Met Lys Ser Glu Leu Glu Tyr Gly
        275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
        355                 360                 365
Gly Tyr His His Ser Asn Glu Gln Gly Ser Gly Tyr Ala Ala Asp Lys
    370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
        435                 440                 445
Glu Asn Glu Arg Thr Leu Asp Phe His Asp Ser Asn Val Lys Asn Leu
    450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Arg Asn Gly Thr Tyr Asp Tyr Pro Gln Tyr Ser Glu Glu Ala
            500                 505                 510
```

```
Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
            565
```

<210> SEQ ID NO 101
<211> LENGTH: 568
<212> TYPE: PRT
<213> ORGANISM: Influenza A virus

<400> SEQUENCE: 101

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320
```

Tyr Val Lys Ser Asn Arg Leu Val Leu Ala Thr Gly Leu Arg Asn Ser
            325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
                515                 520                 525

Ile Tyr Gln Ile Leu Ser Ile Tyr Ser Thr Val Ala Ser Ser Leu Ala
                530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 102
<211> LENGTH: 568
<212> TYPE: PRT
<213> ORGANISM: Influenza A virus

<400> SEQUENCE: 102

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asn Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

```
Lys Ile Gln Ile Ile Pro Lys Ser Ser Trp Ser Asn His Glu Ala Ser
            130                 135                 140

Ser Gly Val Ser Ser Ala Cys Pro Tyr Asn Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Pro Asn Asp Ala Ala Glu Gln Thr Arg Leu Tyr Gln
            195                 200                 205

Asn Pro Ile Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Gly Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Arg Tyr Ser Glu Glu Ala
            500                 505                 510

Arg Leu Asn Arg Glu Glu Ile Ser Gly Val Lys Leu Glu Ser Met Gly
            515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
```

```
                    545                 550                 555                 560

Ser Leu Gln Cys Arg Ile Cys Ile
                565

<210> SEQ ID NO 103
<211> LENGTH: 568
<212> TYPE: PRT
<213> ORGANISM: Influenza A virus

<400> SEQUENCE: 103

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Pro Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Val Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Lys Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
```

```
                  355                 360                 365
Gly Tyr His His Ser Asn Lys Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 104
<211> LENGTH: 568
<212> TYPE: PRT
<213> ORGANISM: Influenza A virus

<400> SEQUENCE: 104

Met Glu Lys Thr Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Thr Asn Val Pro Glu Trp Ser Tyr Ile Val
                85                  90                  95

Glu Lys Ala Ser Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asn His Asp Ala Ser
    130                 135                 140

Ser Gly Val Ser Ser Ala Cys Pro Tyr His Gly Arg Ser Ser Phe Phe
145                 150                 155                 160

Arg Asn Val Val Trp Leu Ile Lys Lys Asn Ser Thr Tyr Pro Thr Ile
```

165                 170                 175
Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
            210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Ser Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Met Gly
            515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 105
<211> LENGTH: 568

<212> TYPE: PRT
<213> ORGANISM: Influenza A virus

<400> SEQUENCE: 105

```
Met Glu Lys Ile Val

-continued

```
Ile Ile Asp Lys Met Asn Thr Gln Phe Glu Ala Val Gly Arg Glu Phe
            405                 410                 415

Asn Asn Leu Glu Arg Arg Ile Glu Leu Asn Lys Lys Met Glu Asp
        420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Glu Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
                500                 505                 510

Arg Leu Asn Arg Glu Glu Ile Ser Gly Val Lys Leu Glu Ser Ile Gly
            515                 520                 525

Thr Tyr Gln Ile Leu Ser Ile Tyr Ser Thr Val Val Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 106
<211> LENGTH: 568
<212> TYPE: PRT
<213> ORGANISM: Influenza A virus

<400> SEQUENCE: 106

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Arg Ile Ile Pro Lys Ser Ser Trp Ser Asn His Asp Ala Ser
    130                 135                 140

Ser Gly Val Ser Ser Ala Cys Pro Tyr Gln Gly Lys Pro Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Pro Glu Asp Leu Leu Val Leu Trp
            180                 185                 190

Gly Ile His His Pro Asn Asp Ala Ala Glu Gln Ile Lys Leu Tyr Gln
        195                 200                 205
```

```
Asn Pro Thr Thr Tyr Ile Ser Val Gly Thr Ser Thr Leu Asn Gln Arg
    210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
            275                 280                 285
Asn Cys Asn Thr Lys Cys Gln Thr Pro Met Gly Ala Ile Asn Ser Ser
    290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Gly Arg Arg Lys Lys Arg Gly Leu Phe Gly Ala Ile
            340                 345                 350
Ala Gly Phe Ile Glu Gly Gly Trp Gln Gly Met Val Asp Gly Trp Tyr
    355                 360                 365
Gly Tyr His His Ser Asn Glu Gln Gly Ser Gly Tyr Ala Ala Asp Lys
    370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                405                 410                 415
Asn Asn Leu Glu Arg Arg Ile Glu Asn Leu Asn Lys Lys Met Glu Asp
            420                 425                 430
Gly Phe Leu Asp Val Trp Thr Tyr Asn Ala Glu Leu Leu Val Leu Met
    435                 440                 445
Glu Asn Glu Arg Thr Leu Asp Phe His Asp Ser Asn Val Lys Asn Leu
    450                 455                 460
Tyr Glu Lys Val Arg Leu Gln Leu Arg Asp Asn Ala Lys Glu Leu Gly
465                 470                 475                 480
Asn Gly Cys Phe Glu Phe Tyr His Lys Cys Asp Asn Glu Cys Met Glu
                485                 490                 495
Ser Val Lys Asn Gly Thr Tyr Asp Tyr Pro Gln Tyr Thr Glu Glu Ala
                500                 505                 510
Arg Leu Asn Arg Glu Glu Ile Ser Gly Val Lys Leu Glu Ser Ile Gly
            515                 520                 525
Thr Tyr Gln Ile Leu Ser Ile Tyr Ser Thr Val Val Ser Ser Leu Ala
    530                 535                 540
Leu Ala Ile Met Val Ala Gly Leu Ser Leu Trp Met Cys Ser Asn Gly
545                 550                 555                 560
Ser Leu Gln Cys Arg Ile Cys Ile
                565

<210> SEQ ID NO 107
<211> LENGTH: 8
<212> TYPE: PRT
<213> ORGANISM: Nocardia aerocolonigenes

<400> SEQUENCE: 107

Leu Ala Thr Ser Asp Thr Glu Asp
1               5
```

-continued

```
<210> SEQ ID NO 108
<211> LENGTH: 568
<212> TYPE: PRT
<213> ORGANISM: Influenza A virus

<400> SEQUENCE: 108
```

| | | | | | | | | | | | | | | | |
|---|---|---|---|---|---|---|---|---|---|---|---|---|---|---|---|
| Met | Glu | Lys | Ile | Val | Leu | Leu | Leu | Ala | Ile | Val | Ser | Leu | Val | Lys | Ser |
| 1 | | | | 5 | | | | | 10 | | | | | 15 | |
| Asp | Gln | Ile | Cys | Ile | Gly | Tyr | His | Ala | Asn | Asn | Ser | Thr | Glu | Gln | Val |
| | | | 20 | | | | | 25 | | | | | 30 | | |
| Asp | Thr | Ile | Met | Glu | Lys | Asn | Val | Thr | Val | Thr | His | Ala | Gln | Asp | Ile |
| | | | 35 | | | | 40 | | | | | 45 | | | |
| Leu | Glu | Lys | Thr | His | Asn | Gly | Lys | Leu | Cys | Asp | Leu | Asp | Gly | Val | Lys |
| 50 | | | | | 55 | | | | | 60 | | | | | |
| Pro | Leu | Ile | Leu | Lys | Asp | Cys | Ser | Val | Ala | Gly | Trp | Leu | Leu | Gly | Asn |
| 65 | | | | | 70 | | | | | 75 | | | | | 80 |
| Pro | Met | Cys | Asp | Glu | Phe | Ile | Asn | Val | Pro | Glu | Trp | Ser | Tyr | Ile | Val |
| | | | | 85 | | | | | 90 | | | | | 95 | |
| Glu | Lys | Ala | Ser | Pro | Ala | Asn | Asp | Leu | Cys | Tyr | Pro | Gly | Asp | Phe | Asn |
| | | | | 100 | | | | | 105 | | | | | 110 | |
| Asp | Tyr | Glu | Glu | Leu | Lys | His | Leu | Leu | Ser | Arg | Ile | Asn | His | Phe | Glu |
| | | | 115 | | | | | 120 | | | | | 125 | | |
| Lys | Ile | Gln | Ile | Ile | Pro | Lys | Ser | Ser | Trp | Ser | Asp | His | Glu | Ala | Ser |
| | 130 | | | | | 135 | | | | | 140 | | | | |
| Ser | Gly | Val | Ser | Ser | Ala | Cys | Pro | Tyr | Leu | Gly | Lys | Pro | Ser | Phe | Phe |
| 145 | | | | | 150 | | | | | 155 | | | | | 160 |
| Arg | Asn | Val | Val | Trp | Leu | Ile | Lys | Lys | Asn | Ser | Thr | Tyr | Pro | Thr | Ile |
| | | | | 165 | | | | | 170 | | | | | 175 | |
| Lys | Arg | Gly | Tyr | Asn | Asn | Thr | Asn | Gln | Glu | Asp | Leu | Leu | Val | Leu | Trp |
| | | | 180 | | | | | 185 | | | | | 190 | | |
| Gly | Ile | His | His | Pro | Asn | Asp | Ala | Ala | Glu | Gln | Ile | Lys | Leu | Tyr | Gln |
| | | | 195 | | | | | 200 | | | | | 205 | | |
| Asn | Pro | Thr | Thr | Tyr | Ile | Ser | Val | Gly | Thr | Ser | Thr | Leu | Asn | Gln | Arg |
| | 210 | | | | | 215 | | | | | 220 | | | | |
| Leu | Val | Pro | Lys | Ile | Ala | Thr | Arg | Ser | Lys | Val | Asn | Gly | Gln | Ser | Gly |
| 225 | | | | | 230 | | | | | 235 | | | | | 240 |
| Arg | Met | Glu | Phe | Phe | Trp | Thr | Ile | Leu | Lys | Pro | Asn | Asp | Ala | Ile | Asn |
| | | | | 245 | | | | | 250 | | | | | 255 | |
| Phe | Glu | Ser | Asn | Gly | Asn | Phe | Ile | Ala | Pro | Glu | Tyr | Ala | Tyr | Lys | Ile |
| | | | 260 | | | | | 265 | | | | | 270 | | |
| Val | Lys | Lys | Gly | Asp | Ser | Ala | Ile | Met | Lys | Ser | Glu | Leu | Glu | Tyr | Gly |
| | | 275 | | | | | 280 | | | | | 285 | | | |
| Asn | Cys | Asn | Thr | Lys | Cys | Gln | Thr | Pro | Val | Gly | Ala | Ile | Asn | Ser | Ser |
| | 290 | | | | | 295 | | | | | 300 | | | | |
| Met | Pro | Phe | His | Asn | Ile | His | Pro | Leu | Thr | Ile | Gly | Glu | Cys | Pro | Lys |
| 305 | | | | | 310 | | | | | 315 | | | | | 320 |
| Tyr | Val | Lys | Ser | Asn | Arg | Leu | Val | Leu | Ala | Thr | Gly | Leu | Arg | Asn | Ala |
| | | | | 325 | | | | | 330 | | | | | 335 | |
| Pro | Gln | Arg | Glu | Gly | Arg | Arg | Lys | Lys | Arg | Gly | Leu | Phe | Gly | Ala | Ile |
| | | | 340 | | | | | 345 | | | | | 350 | | |
| Ala | Gly | Phe | Ile | Glu | Gly | Gly | Trp | Gln | Gly | Met | Val | Asp | Gly | Trp | Tyr |
| | | | 355 | | | | | 360 | | | | | 365 | | |
| Gly | Tyr | His | His | Ser | Asn | Glu | Gln | Gly | Ser | Gly | Tyr | Ala | Ala | Asp | Lys |
| | | 370 | | | | | 375 | | | | | 380 | | | |

```
Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Glu Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Arg Leu Asp Ser Glu Glu Ala
            500                 505                 510

Arg Leu Asn Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 109
<211> LENGTH: 568
<212> TYPE: PRT
<213> ORGANISM: Influenza A virus

<400> SEQUENCE: 109

Met Glu Lys Ile Val Leu Leu Arg Ala Met Ile Asn Leu Val Lys Ser
1               5                   10                  15

Asp Gln Ile Gly Val Gly Tyr His Ala Asp Tyr Ser Thr Glu Gln Gly
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Lys Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Leu Gly Lys Pro Ser Phe Phe
145                 150                 155                 160

Arg Asn Val Val Trp Leu Ile Lys Lys Asn Ser Thr Tyr Pro Thr Ile
                165                 170                 175

Lys Arg Gly Tyr Asn Asn Thr Asn Pro Glu Asp Leu Leu Val Leu Trp
            180                 185                 190
```

```
Gly Ile His His Pro Asn Asp Ala Ala Glu Gln Ile Lys Leu Tyr Gln
            195                 200                 205

Asn Pro Thr Thr Tyr Ile Ser Val Gly Thr Ser Thr Leu Asn Gln Arg
        210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Gln Ile
                    260                 265                 270

Val Lys Lys Gly Asp Ser Ala Ile Met Lys Ser Glu Leu Glu Tyr Gly
                275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                    325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                    420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
            450                 455                 460

Tyr Glu Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
                    500                 505                 510

Arg Leu Asn Arg Glu Glu Ile Ser Gly Val Lys Leu Glu Ser Ile Gly
                515                 520                 525

Thr Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 110
<211> LENGTH: 568
<212> TYPE: PRT
<213> ORGANISM: Influenza A virus

<400> SEQUENCE: 110
```

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Val
        35                  40                  45

Leu Asp Lys Thr His Asn Gly Lys Leu Cys Glu Leu Asp Gly Val Lys
    50                  55                  60

Pro Leu Ile Leu Arg Asp Cys Ser Val Ala Gly Trp Leu Leu Gly Asn
65              70                  75                  80

Pro Met Cys Asp Glu Phe Ile Asn Val Pro Glu Trp Ser Tyr Ile Val
            85                  90                  95

Glu Lys Ala Ser Pro Ala Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Asn Pro Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Ala Asp Leu Leu Val Leu Trp
                180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
            405                 410                 415

Asn Asn Leu Glu Arg Arg Ile Glu Asn Leu Asn Lys Lys Met Glu Asp
            420                 425                 430
```

-continued

```
Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
450                 455                 460

Tyr Glu Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 111
<211> LENGTH: 568
<212> TYPE: PRT
<213> ORGANISM: Influenza A virus

<400> SEQUENCE: 111

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240
```

```
Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
            275                 280                 285

Asn Cys Asn Thr Lys Cys Gln Thr Pro Met Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
            325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
            405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
            450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
            485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
            565

<210> SEQ ID NO 112
<211> LENGTH: 568
<212> TYPE: PRT
<213> ORGANISM: Influenza A virus

<400> SEQUENCE: 112

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45
```

```
Leu Glu Lys Thr His Asn Gly Lys Leu Cys Asp Leu Asp Gly Val Lys
     50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Val Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
        130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
```

```
                465                 470                 475                 480
Asn Gly Cys Phe Glu Phe Tyr His Lys Cys Asp Asn Glu Cys Met Glu
                    485                 490                 495

Ser Val Arg Asn Gly Thr Tyr Asp Tyr Pro Gln Tyr Ser Glu Glu Ala
                    500                 505                 510

Arg Leu Lys Arg Glu Glu Ile Ser Gly Val Lys Leu Glu Ser Ile Gly
                    515                 520                 525

Ile Tyr Gln Ile Leu Ser Ile Tyr Ser Thr Val Ala Ser Ser Leu Ala
                    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                    565

<210> SEQ ID NO 113
<211> LENGTH: 568
<212> TYPE: PRT
<213> ORGANISM: Influenza A virus

<400> SEQUENCE: 113

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Le

-continued

```
                275                 280                 285
Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Ala Lys
                370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
                435                 440                 445

Glu Asn Glu Arg Thr Leu Asp Phe His Asp Ser Asn Val Lys Asn Leu
                450                 455                 460

Tyr Asp Lys Val Arg Leu Gln Leu Lys Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
                515                 520                 525

Ile Tyr Gln Ile Leu Ser Ile Tyr Ser Thr Val Ala Ser Ser Leu Ala
                530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 114
<211> LENGTH: 567
<212> TYPE: PRT
<213> ORGANISM: Influenza A virus

<400> SEQUENCE: 114

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
                35                  40                  45

Leu Glu Lys Thr His Asn Gly Lys Leu Cys Asp Leu Asp Gly Val Lys
                50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
```

-continued

```
                85                  90                  95
Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Leu Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile Ala
            340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
    370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Lys
            500                 505                 510
```

```
Leu Lys Arg Gly Glu Ile Ser Gly Val Lys Leu Glu Ser Ile Gly Ile
        515                 520                 525

Tyr Gln Ile Leu Ser Ile Tyr Ser Thr Val Ala Ser Ser Leu Ala Leu
        530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 115
<211> LENGTH: 568
<212> TYPE: PRT
<213> ORGANISM: Influenza A virus

<400> SEQUENCE: 115

Met Glu Lys Ile Val Leu Leu Ala Ile Val Ser Leu Val Lys Ser
1               5                  10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
        290                 295                 300

Met Pro Phe His Asn Ile His Pro Leu Thr Ile Gly Glu Cys Pro Lys
305                 310                 315                 320
```

```
Tyr Val Lys Ser Asn Arg Leu Val Leu Ala Thr Gly Leu Arg Asn Ser
            325                 330                 335

Pro Gln Gly Glu Arg Arg Arg Lys Arg Gly Leu Phe Gly Ala Ile
        340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
        530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 116
<211> LENGTH: 568
<212> TYPE: PRT
<213> ORGANISM: Influenza A virus

<400> SEQUENCE: 116

Met Glu Asn Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
        50                  55                  60

Pro Leu Ile Leu Arg Asn Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125
```

-continued

```
Lys Ile Gln Ile Ile Pro Lys Ser Ser Trp Ser Asp His Glu Ala Ser
            130                 135                 140
Ser Gly Val Ser Ser Ala Cys Pro Tyr Gln Gly Arg Ser Ser Phe Phe
145                 150                 155                 160
Arg Asn Val Val Trp Leu Ile Lys Lys Asp Asn Ala Tyr Pro Thr Ile
                    165                 170                 175
Lys Arg Ser Tyr Asn Asn Thr Asn Gln Glu Asp Leu Leu Val Leu Trp
                180                 185                 190
Gly Ile His His Pro Asn Asp Ala Ala Glu Gln Thr Arg Leu Tyr Gln
            195                 200                 205
Asn Pro Thr Thr Tyr Ile Ser Val Gly Thr Ser Thr Leu Asn Gln Arg
210                 215                 220
Leu Val Pro Lys Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                    245                 250                 255
Phe Glu Ser Asn Gly Asn Phe Ile Ala Pro Glu Asn Ala Tyr Lys Ile
                260                 265                 270
Val Lys Lys Gly Asp Ser Thr Ile Met Lys Ser Glu Leu Glu Tyr Gly
            275                 280                 285
Asn Cys Asn Thr Lys Cys Gln Thr Pro Ile Gly Ala Ile Asn Ser Ser
290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                    325                 330                 335
Pro Gln Gly Glu Arg Arg Arg Lys Arg Gly Leu Phe Gly Ala Ile
                340                 345                 350
Ala Gly Phe Ile Glu Gly Gly Trp Gln Gly Met Val Asp Gly Trp Tyr
            355                 360                 365
Gly Tyr His His Ser Asn Glu Gln Gly Ser Gly Tyr Ala Ala Asp Lys
370                 375                 380
Glu Ser Thr Gln Lys Ala Ile Asp Gly Val Thr Asn Lys Val Asn Ser
385                 390                 395                 400
Ile Ile Asp Lys Met Asn Thr Gln Phe Glu Ala Val Gly Arg Glu Phe
                    405                 410                 415
Asn Asn Leu Glu Arg Arg Ile Glu Asn Leu Asn Lys Lys Met Glu Asp
                420                 425                 430
Gly Phe Leu Asp Val Trp Thr Tyr Asn Ala Glu Leu Leu Val Leu Met
            435                 440                 445
Glu Asn Glu Arg Thr Leu Asp Phe His Asp Ser Asn Val Lys Asn Leu
450                 455                 460
Tyr Asp Lys Val Arg Leu Gln Leu Arg Asp Asn Ala Lys Glu Leu Gly
465                 470                 475                 480
Asn Gly Cys Phe Glu Phe Tyr His Arg Cys Asp Asn Glu Cys Met Glu
                    485                 490                 495
Ser Val Arg Asn Gly Thr Tyr Asp Tyr Pro Gln Tyr Ser Glu Glu Ala
                500                 505                 510
Arg Leu Lys Arg Glu Glu Ile Ser Gly Val Lys Leu Glu Ser Ile Gly
            515                 520                 525
Thr Tyr Gln Ile Leu Ser Ile Tyr Ser Thr Val Ala Ser Ser Leu Ala
530                 535                 540
Leu Ala Ile Met Val Ala Gly Leu Ser Leu Trp Met Cys Ser Asn Gly
545                 550                 555                 560
```

Ser Leu Gln Cys Arg Ile Cys Ile
                565

<210> SEQ ID NO 117
<211> LENGTH: 568
<212> TYPE: PRT
<213> ORGANISM: Influenza A virus

<400> SEQUENCE: 117

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Arg Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

```
Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 118
<211> LENGTH: 568
<212> TYPE: PRT
<213> ORGANISM: Influenza A virus

<400> SEQUENCE: 118

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175
```

```
Lys Arg Ser Tyr Asn Asn Thr Asn Gln Glu Asp Leu Val Leu Trp
            180                 185                 190

Gly Ile His His Pro Asn Asp Ala Ala Glu Gln Thr Arg Leu Tyr Gln
            195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Ile Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
                260                 265                 270

Val Lys Lys Gly Asp Ser Thr Ile Met Lys Ser Glu Leu Glu Tyr Gly
                275                 280                 285

Asn Cys Asn Thr Lys Cys Gln Thr Pro Ile Gly Ala Ile Asn Ser Ser
            290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Gly Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
                355                 360                 365

Gly Tyr His His Ser Asn Glu Gln Gly Ser Gly Tyr Ala Ala Asp Lys
            370                 375                 380

Glu Ser Thr Gln Lys Ala Ile Tyr Gly Val Thr Asn Thr Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Arg Cys Asp Asn Glu Cys Met Glu
                485                 490                 495

Ser Val Arg Asn Gly Thr Tyr Asp Tyr Pro Gln Tyr Ser Glu Glu Ala
                500                 505                 510

Arg Leu Lys Arg Glu Glu Ile Ser Gly Val Lys Leu Glu Ser Ile Gly
                515                 520                 525

Thr Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 119
<211> LENGTH: 567
<212> TYPE: PRT
```

<213> ORGANISM: Influenza A virus

<400> SEQUENCE: 119

Met Glu Lys Ile Val Leu Leu Ala Ile Val Ser

```
                   405                 410                 415
Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
            450                 455                 460

Asp Lys Val Arg Leu Gln Leu Arg Asp Asn Ala Lys Glu Leu Gly Asn
465                 470                 475                 480

Gly Cys Phe Glu Phe Tyr His Arg Cys Asp Asn Glu Cys Ile Glu Ser
                485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
            530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 120
<211> LENGTH: 566
<212> TYPE: PRT
<213> ORGANISM: Influenza A virus

<400> SEQUENCE: 120

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Asn Glu Asp Phe Asn Trp Thr
130                 135                 140

Gly Val Ala Gln Ser Gly Glu Ser Tyr Ala Cys Lys Arg Gly Ser Val
145                 150                 155                 160

Lys Ser Phe Phe Ser Arg Leu Asn Trp Leu His Glu Ser Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Arg Glu Gln Thr
            195                 200                 205

Lys Leu Tyr Val Arg Ala Ser Gly Arg Val Thr Val Ser Thr Lys Arg
```

```
            210                 215                 220
Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Thr Gly Lys Ser Ser Ile Met Arg Ser Asp Ala
            275                 280                 285

Pro Ile Gly Thr Cys Ser Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asn Gly Trp Tyr Gly
            355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
435                 440                 445

Asn Gln His Thr Ile Asp Leu Thr Asp Ser Glu Met Asn Lys Leu Phe
            450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 121
<211> LENGTH: 566
<212> TYPE: PRT
<213> ORGANISM: Influenza A virus

<400> SEQUENCE: 121

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
```

```
                  20                  25                  30
His His Ala Val Pro Asn Gly Thr Leu Val Lys Thr Ile Thr Asp Asp
         35                  40                  45

Gln Ile Glu Val Thr Asn Ala Thr Glu Leu Val Gln Ser Ser Ser Thr
         50                  55                  60

Gly Lys Ile Cys Asn Asn Pro His Arg Ile Leu Asp Gly Ile Asp Cys
65                   70                  75                  80

Thr Leu Ile Asp Ala Leu Leu Gly Asp Pro His Cys Asp Val Phe Gln
                     85                  90                  95

Asn Glu Thr Trp Asp Leu Phe Val Glu Arg Ser Lys Ala Phe Ser Asn
                    100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Thr Glu Gly Phe Thr Trp Thr
            130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                    165                 170                 175

Tyr Pro Val Leu Asn Val Thr Met Pro Asn Asn Asp Asn Phe Asp Lys
                180                 185                 190

Leu Tyr Ile Trp Gly Ile His His Pro Ser Thr Asn Gln Glu Gln Thr
                195                 200                 205

Ser Leu Tyr Val Gln Ala Ser Gly Arg Val Thr Val Ser Thr Arg Arg
        210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
                260                 265                 270

Tyr Phe Lys Met Arg Thr Gly Lys Ser Ser Ile Met Arg Ser Asp Ala
                275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
            325                 330                 335

Arg Asn Val Pro Glu Lys Gln Thr Arg Gly Leu Phe Gly Ala Ile Ala
                340                 345                 350

Gly Phe Ile Glu Asn Gly Trp Glu Gly Met Ile Asp Gly Trp Tyr Gly
            355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445
```

```
Asn Gln His Thr Ile Asp Leu Thr Asp Ser Glu Met Asn Lys Leu Phe
            450                 455                 460
Glu Lys Thr Arg Arg Gln Leu Arg Glu Asn Ala Glu Glu Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
530                 535                 540
Val Val Leu Leu Gly Phe Ile Met Trp Ala Cys Gln Arg Gly Asn Ile
545                 550                 555                 560
Arg Cys Asn Ile Cys Ile
                565

<210> SEQ ID NO 122
<211> LENGTH: 566
<212> TYPE: PRT
<213> ORGANISM: Influenza A virus

<400> SEQUENCE: 122

Met Lys Thr Ile Ile Ala Leu Ser His Ile Phe Cys Leu Val Leu Gly
1               5                   10                  15
Gln Tyr Leu Pro Gly Asn Asp Asn Ser Thr Ala Thr Leu Cys Leu Gly
                20                  25                  30
His His Ala Val Pro Asn Gly Thr Leu Val Lys Thr Ile Thr Asn Asp
            35                  40                  45
Gln Ile Glu Val Thr Asn Ala Thr Glu Leu Val Gln Ser Ser Ser Thr
50                  55                  60
Gly Lys Ile Cys Asn Asn Pro His Arg Ile Leu Asp Gly Ile Asp Cys
65                  70                  75                  80
Thr Leu Ile Asp Ala Leu Leu Gly Asp Pro His Cys Asp Gly Phe Gln
                85                  90                  95
Asn Glu Thr Trp Asp Leu Phe Val Glu Arg Ser Lys Ala Phe Ser Asn
            100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Ile Thr Glu Gly Phe Thr Trp Thr
130                 135                 140
Gly Val Thr Gln Asn Gly Gly Ser Asn Ala Cys Lys Arg Gly Pro Gly
145                 150                 155                 160
Ser Gly Phe Phe Ser Arg Leu Asn Trp Leu Thr Lys Ser Glu Ser Thr
                165                 170                 175
Tyr Pro Val Leu Asn Val Thr Met Pro Asn Asn Asp Asn Phe Asp Lys
            180                 185                 190
Leu Tyr Ile Trp Gly Val His His Pro Ser Thr Asn Gln Glu Gln Thr
            195                 200                 205
Ser Leu Tyr Val Gln Ala Ser Gly Arg Val Thr Val Ser Thr Arg Arg
210                 215                 220
Ser Gln Gln Thr Ile Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                245                 250                 255
```

-continued

```
Asp Val Leu Val Ile Asn Ser Asn Ala Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Arg Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr Asp Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 123
<211> LENGTH: 566
<212> TYPE: PRT
<213> ORGANISM: Influenza A virus

<400> SEQUENCE: 123

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60
```

```
Gly Lys Ile Cys Asn Asn Pro His Arg Ile Leu Asp Gly Ile Asp Cys
 65                  70                  75                  80

Thr Leu Ile Asp Ala Leu Leu Gly Asp Pro His Cys Asp Val Phe Gln
                 85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Ile His His Pro Ser Thr Asn Gln Glu Gln Thr
        195                 200                 205

Ser Leu Tyr Val Gln Ala Ser Gly Arg Val Thr Val Ser Thr Arg Arg
210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Arg Arg Gln Leu Arg Glu Asn Ala Glu Glu Met Gly Asn
465                 470                 475                 480

Gly Cys Phe Lys Ile Tyr His Lys Cys Asp Asn Ala Cys Ile Glu Ser
                485                 490                 495
```

```
Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 124
<211> LENGTH: 566
<212> TYPE: PRT
<213> ORGANISM: Influenza A virus

<400> SEQUENCE: 124

Met Lys Thr Ile Ile Ala Leu Ser Tyr Ile Phe Cys Leu Val Leu Gly
1               5                   10                  15

Gln Asp Phe Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Gly Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Ser Glu Gly Phe Thr Trp Thr
    130                 135                 140

Gly Val Thr Gln Asn Gly Gly Ser Asn Ala Cys Lys Arg Gly Pro Asp
145                 150                 155                 160

Ser Gly Phe Phe Ser Arg Leu Asn Trp Leu Tyr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asp Gln Glu Gln Thr
        195                 200                 205

Ser Leu Tyr Val Gln Ala Ser Gly Arg Val Thr Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Gly Thr Cys Ile Ser Glu Cys Ile Thr Pro Asn Gly Ser Ile
    290                 295                 300
```

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 125
<211> LENGTH: 566
<212> TYPE: PRT
<213> ORGANISM: Influenza A virus

<400> SEQUENCE: 125

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Arg Ser Asn
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Glu Lys Phe Asp Lys
            180                 185                 190

Leu Tyr Ile Trp Gly Val His His Pro Ser Thr Asp Ser Asp Gln Ile
    195                 200                 205

Ser Ile Tyr Ala Gln Ala Ser Gly Arg Val Thr Val Ser Thr Lys Arg
    210                 215                 220

Ser Gln Gln Thr Val Ile Pro Asn Ile Gly Ser Ser Pro Trp Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
    275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
    355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
    435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
    515                 520                 525

Asp Trp Ile Leu Trp Ile Ser Phe Ala Ile Ser Cys Phe Leu Leu Cys

```
                530                 535                 540
Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 126
<211> LENGTH: 566
<212> TYPE: PRT
<213> ORGANISM: Influenza A virus
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid

<400> SEQUENCE: 126

Met Lys Thr Ile Ile Ala Leu Ser Tyr Ile Phe Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Ile Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Gly Phe Asn Trp Thr
130                 135                 140

Gly Val Thr Gln Ser Gly Gly Ser Tyr Xaa Cys Lys Arg Gly Ser Val
145                 150                 155                 160

Asn Ser Phe Phe Ser Arg Leu Asn Trp Leu Tyr Glu Ser Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Xaa Thr Glu Lys Glu Gln Thr
        195                 200                 205

Asn Leu Tyr Val Arg Ala Ser Gly Arg Val Thr Val Ser Thr Lys Arg
    210                 215                 220

Ser Gln Gln Thr Val Ile Pro Asn Ile Gly Ser Xaa Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Thr Gly Lys Ser Ser Ile Met Arg Ser Asp Ala
```

```
                275                 280                 285
Pro Ile Gly Thr Cys Ser Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Thr Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln Tyr Thr Ile Asp Leu Thr Asp Ser Glu Met Asn Lys Leu Phe
                450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 127
<211> LENGTH: 566
<212> TYPE: PRT
<213> ORGANISM: Influenza A virus

<400> SEQUENCE: 127

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
                35                  40                  45

Gln Ile Glu Val Thr Asn Ala Thr Glu Leu Val Gln Ser Ser Ser Thr
                50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
```

-continued

```
                    85                  90                  95
Asn Lys Glu Trp Asp Leu Phe Val Arg Ser Lys Ala Tyr Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Asn Glu Asp Phe Asn Trp Thr
130                 135                 140

Gly Val Ala Gln Ser Gly Glu Ser Tyr Ala Cys Lys Arg Gly Ser Val
145                 150                 155                 160

Lys Ser Phe Phe Ser Arg Leu Asn Trp Leu His Glu Ser Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Arg Glu Gln Thr
        195                 200                 205

Asn Leu Tyr Val Arg Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510
```

```
Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 128
<211> LENGTH: 566
<212> TYPE: PRT
<213> ORGANISM: Influenza A virus

<400> SEQUENCE: 128

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Gly Phe Asn Trp Thr
    130                 135                 140

Gly Val Thr Gln Ser Gly Gly Ser Tyr Ala Cys Lys Arg Gly Ser Asp
145                 150                 155                 160

Asn Ser Phe Phe Ser Arg Leu Asn Trp Leu Tyr Glu Ser Glu Ser Lys
                165                 170                 175

Tyr Pro Val Leu Asn Val Thr Met Pro Asn Asn Gly Asn Phe Asp Lys
            180                 185                 190

Leu Tyr Ile Trp Gly Val His His Pro Ser Thr Asp Lys Glu Gln Thr
        195                 200                 205

Lys Leu Tyr Val Arg Ala Ser Gly Arg Val Thr Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Gly Ile Ser Ile Tyr Trp Thr Ile Val Lys Pro Gly
                245                 250                 255

Asp Ile Leu Leu Ile Asn Ser Asn Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320
```

-continued

```
Cys Pro Lys Tyr Val Lys Gln Asn Thr Leu Lys Leu Ala Thr Gly Met
            325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Thr Gly Gln Ala Ala Asp Leu Lys
            370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Lys Gly Asn Ile
545                 550                 555                 560

Arg Cys Asn Ile Cys Ile
            565
```

<210> SEQ ID NO 129
<211> LENGTH: 566
<212> TYPE: PRT
<213> ORGANISM: Influenza A virus

<400> SEQUENCE: 129

```
Met Lys Thr Ile Ile Ala Phe Ser Tyr Ile Leu Cys Leu Ile Phe Ala
1               5                   10                  15

Gln Lys Ile Pro Gly Ser Asp Asn Ser Met Ala Thr Leu Cys Leu Gly
            20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Gln Ser Ser Ser Thr
            50                  55                  60

Gly Arg Ile Cys Asn Ser Pro His Gln Ile Leu Asp Gly Lys Asn Cys
65                  70                  75                  80

Thr Leu Ile Asp Ala Leu Leu Gly Asp Pro His Cys Asp Asp Phe Gln
            85                  90                  95

Asn Lys Glu Trp Asp Leu Phe Val Glu Arg Ser Thr Ala Tyr Ser Asn
            100                 105                 110

Cys Tyr Pro Tyr Asp Val Pro Asp Tyr Ala Ser Leu Arg Ser Leu Val
            115                 120                 125
```

-continued

Ala Ser Ser Gly Thr Leu Glu Phe Thr Gln Glu Ser Phe Asn Trp Thr
            130                 135                 140

Gly Val Ala Gln Asp Gly Thr Ser Ser Ala Cys Lys Arg Gly Ser Val
145                 150                 155                 160

Lys Ser Phe Phe Ser Arg Leu Asn Trp Leu His Glu Leu Gly Tyr Lys
                165                 170                 175

Tyr Pro Ala Leu Asn Val Thr Met Pro Asn Asn Asp Lys Phe Asp Lys
            180                 185                 190

Leu Tyr Ile Trp Gly Val His His Pro Ser Thr Asp Arg Asp Gln Thr
        195                 200                 205

Ser Leu Tyr Val Gln Ala Ser Gly Arg Val Thr Val Ser Thr Lys Arg
    210                 215                 220

Ser Gln Gln Thr Val Ile Pro Asn Ile Gly Phe Arg Pro Trp Val Arg
225                 230                 235                 240

Gly Ile Ser Ser Ile Ile Ser Ile Tyr Trp Thr Ile Val Lys Pro Gly
                245                 250                 255

Asp Ile Leu Leu Ile Thr Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Asp Asn Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Thr Gly Lys Leu Asn Arg Val
385                 390                 395                 400

Ile Lys Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
            565

<210> SEQ ID NO 130
<211> LENGTH: 566
<212> TYPE: PRT
<213> ORGANISM: Influenza A virus

<400> SEQUENCE: 130

Met Lys Thr Ile Ile Ala Phe Ser Tyr Ile Leu Cys Leu Ile Phe Ala
1               5                   10                  15

Gln Lys Ile Pro Gly Ser Asp Asn Ser Met Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Arg Ile Cys Asn Ser Pro His Gln Ile Leu Asp Gly Lys Asn Cys
65                  70                  75                  80

Thr Leu Ile Asp Ala Leu Leu Gly Asp Pro His Cys Asp Asp Phe Gln
                85                  90                  95

Asn Lys Glu Trp Asp Leu Phe Val Glu Arg Ser Thr Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Thr Gln Ser Phe Asn Trp Thr
    130                 135                 140

Gly Val Ala Gln Asp Gly Thr Ser Ser Ala Cys Lys Arg Gly Ser Val
145                 150                 155                 160

Lys Ser Phe Phe Ser Arg Leu Asn Trp Leu His Glu Leu Gly Tyr Lys
                165                 170                 175

Tyr Pro Ala Leu Asn Val Thr Met Pro Asn Asn Asp Lys Phe Asp Lys
            180                 185                 190

Leu Tyr Ile Trp Gly Val His His Pro Ser Thr Asp Arg Asp Gln Thr
        195                 200                 205

Ser Leu Tyr Val Gln Ala Ser Gly Arg Val Thr Val Ser Thr Lys Arg
    210                 215                 220

Ser Gln Gln Thr Val Ile Pro Asn Ile Gly Phe Arg Pro Trp Val Arg
225                 230                 235                 240

Gly Ile Ser Ser Ile Ile Ser Ile Tyr Trp Thr Ile Val Lys Pro Gly
                245                 250                 255

Asp Ile Leu Leu Ile Thr Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Asp Asn Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

```
Phe Arg His Gln Asn Ser Glu Gly Thr Gly Gln Ala Ala Asp Leu Lys
    370                 375                 380

Ser Thr Gln Ala Ala Ile Asn Gln Ile Thr Gly Lys Leu Asn Arg Val
385                 390                 395                 400

Ile Lys Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
435                 440                 445

Asn Gln His Thr Ile Asp Leu Thr Asp Ser Glu Met Asn Lys Leu Phe
        450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 131
<211> LENGTH: 566
<212> TYPE: PRT
<213> ORGANISM: Influenza A virus

<400> SEQUENCE: 131

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Asp Arg Ile Cys Asp Ser Pro His Arg Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Gln Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Tyr Ala Cys Lys Arg Arg Ser Ile
145                 150                 155                 160

Lys Ser Phe Phe Ser Arg Leu Asn Trp Leu His Gln Leu Lys Tyr Lys
                165                 170                 175
```

Tyr Pro Ala Leu Asn Val Thr Met Pro Asn Asn Asp Lys Phe Asp Lys
            180                 185                 190

Leu Tyr Ile Trp Gly Val His His Pro Ser Thr Asp Ser Asp Gln Thr
        195                 200                 205

Ser Leu Tyr Ala Gln Ala Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
                260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
        290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 132
<211> LENGTH: 566
<212> TYPE: PRT

<213> ORGANISM: Influenza A virus

<400> SEQUENCE: 132

Met Lys Thr Ile Ile Ala Leu Ser Tyr

```
                            405                 410                 415
Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asn His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 133
<211> LENGTH: 566
<212> TYPE: PRT
<213> ORGANISM: Influenza A virus
<220> FEATURE:
<221> NAME/KEY: misc_feature
<222> LOCATION: (318)..(318)
<223> OTHER INFORMATION: Xaa can be any naturally occurring amino acid

<400> SEQUENCE: 133

Met Lys Thr Ile Ile Ala Leu Ser Tyr Ile Phe Cys Leu Val Leu Gly
1               5                   10                  15

Gln Asp Phe Pro Gly Asn Asp Asn Ser Thr Ala Thr Leu Cys Leu Gly
                20                  25                  30

His His Ala Val Pro Asn Gly Thr Leu Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Gly Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Ser Glu Gly Phe Thr Trp Thr
130                 135                 140

Gly Val Thr Gln Asn Gly Gly Ser Asn Ala Cys Lys Arg Gly Pro Asp
145                 150                 155                 160

Ser Gly Phe Phe Ser Arg Leu Asn Trp Leu Tyr Lys Ser Gly Ser Thr
                165                 170                 175

Tyr Pro Val Leu Asn Val Thr Met Pro Asn Asn Asp Asn Phe Asp Lys
            180                 185                 190
```

```
Leu Tyr Ile Trp Gly Val His His Pro Ser Thr Asp Gln Glu Gln Thr
        195                 200                 205

Ser Leu Tyr Val Gln Ala Ser Gly Arg Val Thr Val Ser Thr Lys Arg
210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Ile Leu Val Ile Asn Ser Asn Gly Asn Leu Ile Ala Pro Arg Gly
                260                 265                 270

Tyr Phe Lys Met Arg Thr Gly Lys Ser Ser Ile Met Arg Ser Asp Ala
                275                 280                 285

Pro Ile Gly Thr Cys Ile Ser Glu Cys Ile Thr Pro Asn Gly Ser Ile
290                 295                 300

Pro Asn Asp Lys Pro Phe Gln Asn Val Asn Lys Ile Thr Xaa Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Ser Ala Ile Ala
                340                 345                 350

Gly Phe Ile Glu Asn Gly Trp Glu Gly Met Ile Asp Gly Trp Tyr Gly
                355                 360                 365

Phe Arg His Gln Asn Ser Glu Gly Thr Gly Gln Pro Ala Asp Leu Lys
                370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Lys Thr Ser Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Val Leu Leu Gly Phe Ile Met Thr Ala Cys Gln Lys Gly Asn Ile
545                 550                 555                 560

Arg Cys Asn Ile Cys Ile
                565

<210> SEQ ID NO 134
<211> LENGTH: 392
<212> TYPE: PRT
<213> ORGANISM: Polyomavirus sp

<400> SEQUENCE: 134
```

```
Met Ala Pro Lys Arg Lys Ser Gly Val Ser Lys Cys Glu Thr Lys Cys
1               5                   10                  15

Thr Lys Ala Cys Pro Arg Pro Ala Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Lys Arg Gly Pro Ser Gly Gly Thr Glu
                85                  90                  95

Asp Ser Pro Gly Asn Asn Thr Leu Pro Thr Trp Ser Met Ala Lys Leu
            100                 105                 110

Gln Leu Pro Met Leu Asn Glu Asp Leu Thr Cys Asp Thr Leu Gln Met
        115                 120                 125

Trp Glu Ala Val Ser Val Lys Thr Glu Val Val Gly Ser Gly Ser Leu
    130                 135                 140

Leu Asp Val His Gly Phe Asn Lys Pro Thr Asp Thr Val Asn Thr Lys
145                 150                 155                 160

Gly Ile Ser Thr Pro Val Glu Gly Ser Gln Tyr His Val Phe Ala Val
            165                 170                 175

Gly Gly Glu Pro Leu Asp Leu Gln Gly Leu Val Thr Asp Ala Arg Thr
        180                 185                 190

Lys Tyr Lys Glu Glu Gly Val Val Thr Ile Lys Thr Ile Thr Lys Lys
    195                 200                 205

Asp Met Val Asn Lys Asp Gln Val Leu Asn Pro Ile Ser Lys Ala Lys
210                 215                 220

Leu Asp Lys Asp Gly Met Tyr Pro Val Glu Ile Trp His Pro Asp Pro
225                 230                 235                 240

Ala Lys Asn Glu Asn Thr Arg Tyr Phe Gly Asn Tyr Thr Gly Gly Thr
            245                 250                 255

Thr Thr Pro Pro Val Leu Gln Phe Thr Asn Thr Leu Thr Thr Val Leu
        260                 265                 270

Leu Asp Glu Asn Gly Val Gly Pro Leu Cys Lys Gly Glu Gly Leu Tyr
    275                 280                 285

Leu Ser Cys Val Asp Ile Met Gly Trp Arg Val Thr Arg Asn Tyr Asp
290                 295                 300

Val His His Trp Arg Gly Leu Pro Arg Tyr Phe Lys Ile Thr Leu Arg
305                 310                 315                 320

Lys Arg Trp Val Lys Asn Pro Tyr Pro Met Ala Ser Leu Ile Ser Ser
            325                 330                 335

Leu Phe Asn Asn Met Leu Pro Gln Val Gln Gly Gln Pro Met Glu Gly
        340                 345                 350

Glu Asn Thr Gln Val Glu Glu Val Arg Val Tyr Asp Gly Thr Glu Pro
    355                 360                 365

Val Pro Gly Asp Pro Asp Met Thr Arg Tyr Val Asp Arg Phe Gly Lys
370                 375                 380

Thr Lys Thr Val Phe Pro Gly Asn
385                 390

<210> SEQ ID NO 135
<211> LENGTH: 402
<212> TYPE: PRT
<213> ORGANISM: Polyomavirus sp
```

<400> SEQUENCE: 135

```
Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Pro Ser Thr Asn Gln Glu Gln Thr Ser Leu
                85                  90                  95

Tyr Val Gln Ala Ser Gly Arg Gly Thr Glu Asp Ser Pro Gly Asn Asn
            100                 105                 110

Thr Leu Pro Thr Trp Ser Met Ala Lys Leu Gln Leu Pro Met Leu Asn
        115                 120                 125

Glu Asp Leu Thr Cys Asp Thr Leu Gln Met Trp Glu Ala Val Ser Val
    130                 135                 140

Lys Thr Glu Val Val Gly Ser Gly Ser Leu Leu Asp Val His Gly Phe
145                 150                 155                 160

Asn Lys Pro Thr Asp Thr Val Asn Thr Lys Gly Ile Ser Thr Pro Val
                165                 170                 175

Glu Gly Ser Gln Tyr His Val Phe Ala Val Gly Gly Glu Pro Leu Asp
            180                 185                 190

Leu Gln Gly Leu Val Thr Asp Ala Arg Thr Lys Tyr Lys Glu Glu Gly
        195                 200                 205

Val Val Thr Ile Lys Thr Ile Thr Lys Lys Asp Met Val Asn Lys Asp
    210                 215                 220

Gln Val Leu Asn Pro Ile Ser Lys Ala Lys Leu Asp Lys Asp Gly Met
225                 230                 235                 240

Tyr Pro Val Glu Ile Trp His Pro Asp Pro Ala Lys Asn Glu Asn Thr
                245                 250                 255

Arg Tyr Phe Gly Asn Tyr Thr Gly Gly Thr Thr Thr Pro Pro Val Leu
            260                 265                 270

Gln Phe Thr Asn Thr Leu Thr Thr Val Leu Leu Asp Glu Asn Gly Val
        275                 280                 285

Gly Pro Leu Cys Lys Gly Glu Gly Leu Tyr Leu Ser Cys Val Asp Ile
    290                 295                 300

Met Gly Trp Arg Val Thr Arg Asn Tyr Asp Val His His Trp Arg Gly
305                 310                 315                 320

Leu Pro Arg Tyr Phe Lys Ile Thr Leu Arg Lys Arg Trp Val Lys Asn
                325                 330                 335

Pro Tyr Pro Met Ala Ser Leu Ile Ser Ser Leu Phe Asn Asn Met Leu
            340                 345                 350

Pro Gln Val Gln Gly Gln Pro Met Glu Gly Asn Thr Gln Val Glu
        355                 360                 365

Glu Val Arg Val Tyr Asp Gly Thr Glu Pro Val Pro Gly Asp Pro Asp
    370                 375                 380

Met Thr Arg Tyr Val Asp Arg Phe Gly Lys Thr Lys Thr Val Phe Pro
385                 390                 395                 400

Gly Asn
```

<210> SEQ ID NO 136
<211> LENGTH: 392
<212> TYPE: PRT
<213> ORGANISM: Polyomavirus sp

<400> SEQUENCE: 136

```
Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Ser Lys Arg Gly Pro Gly Ser Gly Ala Tyr Asp
    290                 295                 300

Val His His Trp Arg Gly Leu Pro Arg Tyr Phe Lys Ile Thr Leu Arg
305                 310                 315                 320

Lys Arg Trp Val Lys Asn Pro Tyr Pro Met Ala Ser Leu Ile Ser Ser
                325                 330                 335

Leu Phe Asn Asn Met Leu Pro Gln Val Gln Gly Gln Pro Met Glu Gly
            340                 345                 350

Glu Asn Thr Gln Val Glu Glu Val Arg Val Tyr Asp Gly Thr Glu Pro
        355                 360                 365

Val Pro Gly Asp Pro Asp Met Thr Arg Tyr Val Asp Arg Phe Gly Lys
    370                 375                 380
```

Thr Lys Thr Val Phe Pro Gly Asn
385                 390

<210> SEQ ID NO 137
<211> LENGTH: 402
<212> TYPE: PRT
<213> ORGANISM: Polyomavirus sp

<400> SEQUENCE: 137

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Ser Pro Ser Thr Asn Gln Glu Gln Thr Ser Leu
290                 295                 300

Tyr Val Gln Ala Ser Gly Arg Ala Tyr Asp Val His His Trp Arg Gly
305                 310                 315                 320

Leu Pro Arg Tyr Phe Lys Ile Thr Leu Arg Lys Arg Trp Val Lys Asn
                325                 330                 335

Pro Tyr Pro Met Ala Ser Leu Ile Ser Ser Leu Phe Asn Asn Met Leu
            340                 345                 350

Pro Gln Val Gln Gly Gln Pro Met Glu Gly Glu Asn Thr Gln Val Glu
        355                 360                 365

```
Glu Val Arg Val Tyr Asp Gly Thr Glu Pro Val Pro Gly Asp Pro Asp
            370                 375                 380

Met Thr Arg Tyr Val Asp Arg Phe Gly Lys Thr Lys Thr Val Phe Pro
385                 390                 395                 400

Gly Asn

<210> SEQ ID NO 138
<211> LENGTH: 392
<212> TYPE: PRT
<213> ORGANISM: Polyomavirus sp

<400> SEQUENCE: 138

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Ser Pro Tyr Asn Gly Lys Ser Ser Ala Tyr Asp
    290                 295                 300

Val His His Trp Arg Gly Leu Pro Arg Tyr Phe Lys Ile Thr Leu Arg
305                 310                 315                 320

Lys Arg Trp Val Lys Asn Pro Tyr Pro Met Ala Ser Leu Ile Ser Ser
                325                 330                 335

Leu Phe Asn Asn Met Leu Pro Gln Val Gln Gly Gln Pro Met Glu Gly
```

```
                     340                 345                 350
Glu Asn Thr Gln Val Glu Val Arg Val Tyr Asp Gly Thr Glu Pro
            355                 360                 365

Val Pro Gly Asp Pro Asp Met Thr Arg Tyr Val Asp Arg Phe Gly Lys
370                 375                 380

Thr Lys Thr Val Phe Pro Gly Asn
385                 390

<210> SEQ ID NO 139
<211> LENGTH: 402
<212> TYPE: PRT
<213> ORGANISM: Polyomavirus sp

<400> SEQUENCE: 139

Glu Ala Phe Leu Asn Pro Arg Met Gly Gln Pro Pro Thr Pro Glu Ser
1               5                   10                  15

Leu Thr Glu Gly Gly Gln Tyr Tyr Gly Trp Ser Arg Gly Ile Asn Leu
            20                  25                  30

Ala Thr Ser Asp Thr Glu Asp Ser Pro Gly Asn Asn Thr Leu Pro Thr
        35                  40                  45

Trp Ser Met Ala Lys Leu Gln Leu Pro Met Leu Asn Glu Asp Leu Thr
50                  55                  60

Cys Asp Thr Leu Gln Met Trp Glu Ala Val Ser Val Lys Thr Glu Val
65                  70                  75                  80

Val Gly Ser Gly Ser Leu Leu Asp Val His Gly Phe Asn Lys Pro Thr
                85                  90                  95

Asp Thr Val Asn Thr Lys Gly Ile Ser Thr Pro Val Glu Gly Ser Gln
            100                 105                 110

Tyr His Val Phe Ala Val Gly Gly Glu Pro Leu Asp Leu Gln Gly Leu
        115                 120                 125

Val Thr Asp Ala Arg Thr Lys Tyr Lys Glu Glu Gly Val Val Thr Ile
130                 135                 140

Lys Thr Ile Thr Lys Lys Asp Met Val Asn Lys Asp Gln Val Leu Asn
145                 150                 155                 160

Pro Ile Ser Lys Ala Lys Leu Asp Lys Asp Gly Met Tyr Pro Val Glu
                165                 170                 175

Ile Trp His Pro Asp Pro Ala Lys Asn Glu Asn Thr Arg Tyr Phe Gly
            180                 185                 190

Asn Tyr Thr Gly Gly Thr Thr Thr Pro Pro Val Leu Gln Phe Thr Asn
        195                 200                 205

Thr Leu Thr Thr Val Leu Leu Asp Glu Asn Gly Val Gly Pro Leu Cys
210                 215                 220

Lys Gly Glu Gly Leu Tyr Leu Ser Cys Val Asp Ile Met Gly Trp Arg
225                 230                 235                 240

Val Thr Arg Ser Pro Asn Asp Ala Ala Glu Gln Thr Lys Leu Tyr Gln
                245                 250                 255

Asn Pro Thr Thr Tyr Ala Tyr Asp Val His His Trp Arg Gly Leu Pro
            260                 265                 270

Arg Tyr Phe Lys Ile Thr Leu Arg Lys Arg Trp Val Lys Asn Pro Tyr
        275                 280                 285

Pro Met Ala Ser Leu Ile Ser Ser Leu Phe Asn Asn Met Leu Pro Gln
        290                 295                 300

Val Gln Gly Gln Pro Met Glu Gly Glu Asn Thr Gln Val Glu Glu Val
305                 310                 315                 320

Arg Val Tyr Asp Gly Thr Glu Pro Val Pro Gly Asp Pro Asp Met Thr
```

```
                    325                 330                 335
Arg Tyr Val Asp Arg Phe Gly Lys Thr Lys Thr Val Phe Pro Gly Asn
                340                 345                 350

Met Ala Pro Lys Arg Lys Ser Gly Val Ser Lys Cys Glu Thr Lys Cys
                355                 360                 365

Thr Lys Ala Cys Pro Arg Pro Ala Pro Val Pro Lys Leu Leu Ile Lys
            370                 375                 380

Gly Gly Met Glu Val Leu Asp Leu Val Thr Gly Pro Asp Ser Val Thr
385                 390                 395                 400

Glu Ile

<210> SEQ ID NO 140
<211> LENGTH: 408
<212> TYPE: PRT
<213> ORGANISM: Polyomavirus sp

<400> SEQUENCE: 140

Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Ser Ser Leu Leu Thr Glu Val Glu Thr Pro Ile
    290                 295                 300
```

```
Arg Asn Glu Trp Gly Cys Arg Cys Asn Asp Ser Ser Asp Ala Tyr Asp
305                 310                 315                 320

Val His His Trp Arg Gly Leu Pro Arg Tyr Phe Lys Ile Thr Leu Arg
                325                 330                 335

Lys Arg Trp Val Lys Asn Pro Tyr Pro Met Ala Ser Leu Ile Ser Ser
            340                 345                 350

Leu Phe Asn Asn Met Leu Pro Gln Val Gln Gly Gln Pro Met Glu Gly
        355                 360                 365

Glu Asn Thr Gln Val Glu Glu Val Arg Val Tyr Asp Gly Thr Glu Pro
    370                 375                 380

Val Pro Gly Asp Pro Asp Met Thr Arg Tyr Val Asp Arg Phe Gly Lys
385                 390                 395                 400

Thr Lys Thr Val Phe Pro Gly Asn
                405
```

<210> SEQ ID NO 141
<211> LENGTH: 9
<212> TYPE: PRT
<213> ORGANISM: Nocardia aerocolonigenes

<400> SEQUENCE: 141

```
Leu Ala Thr Ser Ala Gly Thr Glu Asp
1               5
```

<210> SEQ ID NO 142
<211> LENGTH: 3
<212> TYPE: PRT
<213> ORGANISM: Pseudomonas sp

<400> SEQUENCE: 142

```
Gly Thr Thr
1
```

<210> SEQ ID NO 143
<211> LENGTH: 4
<212> TYPE: PRT
<213> ORGANISM: Pseudomonas sp.

<400> SEQUENCE: 143

```
Gly Thr His Val
1
```

<210> SEQ ID NO 144
<211> LENGTH: 6
<212> TYPE: PRT
<213> ORGANISM: Alcaligenes faecalis

<400> SEQUENCE: 144

```
Thr Arg Asn Tyr Asp Val
1               5
```

<210> SEQ ID NO 145
<211> LENGTH: 7
<212> TYPE: PRT
<213> ORGANISM: Alcaligenes faecalis

<400> SEQUENCE: 145

```
Thr Arg Ser Ala Tyr Asp Val
1               5
```

The invention claimed is:

1. An isolated protein comprising a murine polyomavirus VP1 amino acid sequence, or a fragment thereof, wherein one or more exposed loops of said murine polyomavirus VP1 amino acid sequence has an insertion of an amino acid sequence of a virus protein other than murine polyomavirus VP1, or a fragment of said virus protein other than murine polyomavirus VP1.

2. The isolated protein of claim 1, wherein the one or more exposed loops of said murine polyomavirus VP1 amino acid sequence comprise an insertion site selected from the group consisting of site 1, site 3 and site 4.

3. The isolated protein of claim 1, wherein the insertion site is selected from the group consisting of site 1 and site 4.

4. The isolated protein of claim 2, wherein the virus protein other than murine polyomavirus VP1 or a fragment thereof, is an influenza virus protein.

5. The isolated protein of claim 4, wherein the influenza virus protein is selected from the group consisting of HA, NP, NA, M2 and M1.

6. The isolated protein of claim 5, wherein the influenza virus protein is selected from the group consisting of HA and M2.

7. The isolated protein of claim 2, wherein the virus protein other than murine polyomavirus VP1 is an exposed loop of HA selected from the group consisting of loop A, loop B, loop C, loop D and loop E, or a fragment thereof.

8. The isolated protein of claim 7, wherein the exposed loop of HA is selected from the group consisting of loop A and loop B, or a fragment thereof.

9. The isolated protein of claim 8, wherein the fragment of loop A is an antigenic epitope comprising an amino acid sequence selected from the group consisting of SEQ ID NO: 75, SEQ ID NO: 77 and SEQ ID NO: 79, or a variant thereof.

10. The isolated protein of claim 9, wherein the variant comprises an amino acid sequence selected from the group consisting of SEQ ID NO: 1; SEQ ID NO:2; SEQ ID NO:3; SEQ ID NO:4; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:19; SEQ ID NO:20; SEQ ID NO:22; SEQ ID NO:23; SEQ ID NO:47; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59 and SEQ ID NO:60.

11. The isolated protein of claim 9, wherein the variant has at least 30% sequence identity to the amino acid sequence selected from the group consisting of SEQ ID NO: 75, SEQ ID NO: 77 and SEQ ID NO: 79.

12. The isolated protein of claim 8, wherein the fragment of loop B is an antigenic epitope comprising an amino acid sequence selected from the group consisting of SEQ ID NO: 76, SEQ ID NO: 78 and SEQ ID NO: 80, or a variant thereof.

13. The isolated protein of claim 12, wherein the variant comprises an amino acid sequence selected from the group consisting of SEQ ID NO:25; SEQ ID NO:26; SEQ ID NO:27; SEQ ID NO:30; SEQ ID NO:34; SEQ ID NO:35; SEQ ID NO:36; SEQ ID NO:42; SEQ ID NO:43; SEQ ID NO:44; SEQ ID NO:45; SEQ ID NO:46; SEQ ID NO:61; SEQ ID NO:65; SEQ ID NO:66; SEQ ID NO:67; SEQ ID NO:69; SEQ ID NO:70; SEQ ID NO:71; SEQ ID NO:72; SEQ ID NO:73 and SEQ ID NO:74.

14. The isolated protein of claim 12, wherein the variant has at least 30% sequence identity to the amino acid sequence selected from the group consisting of SEQ ID NO: 76, SEQ ID NO: 78 and SEQ ID NO: 80.

15. The isolated protein of claim 2, wherein the said virus protein other than murine polyomavirus VP1, or a fragment thereof, is a single protein or a plurality of proteins.

16. A virus-like particle comprising one or more isolated proteins of claim 1.

17. A virus-like particle produced according to a method comprising:

(a) introducing an isolated nucleic acid comprising a nucleotide sequence encoding the isolated protein of claim 1 into a host cell;

(b) culturing said host cell under conditions which facilitate production of the protein encoded by the nucleic acid;

(c) optionally purifying the protein; and (d) assembling the protein purified according to step (c) to produce the virus-like particle.

18. A composition comprising a murine polyomavirus VP1 amino acid sequence, or a fragment thereof, wherein one or more exposed loops of said murine polyomavirus VP1 amino acid sequence has an insertion of an amino acid sequence of a virus protein other than murine polyomavirus VP1, or a fragment of said virus protein other than murine polyomavirus VP1, and a pharmaceutically-acceptable carrier, diluent or excipient.

19. The composition of claim 18, wherein the composition is an immunotherapeutic composition.

20. A method of immunizing an animal, said method comprising the step of administering the composition of claim 18 to said animal to thereby induce immunity in said animal.

21. The method of claim 20, wherein the animal is a mammal.

22. The method of claim 21, wherein the mammal is a human.

23. The composition of claim 18, wherein the one or more exposed loops of said murine polyomavirus VP1 amino acid sequence comprise an insertion site selected from the group consisting of site 1, site 3 and site 4.

24. The composition of claim 18, wherein the insertion site is selected from the group consisting of site 1 and site 4.

25. The composition of claim 23, wherein the virus protein other than murine polyomavirus VP1 or a fragment thereof, is an influenza virus protein.

26. The composition of claim 25, wherein the influenza virus protein is selected from the group consisting of HA, NP, NA, M2 and M1.

27. The composition of claim 26, wherein the influenza virus protein is selected from the group consisting of HA and M2.

28. A method of immunizing an animal, said method comprising the step of administering the composition of claim 25 to said animal to thereby induce immunity against an influenza virus in said animal.

29. The method of claim 28, wherein the influenza virus is avian influenza virus.

30. The composition of claim 23, wherein the virus protein other than murine polyomavirus VP1 is an exposed loop of HA selected from the group consisting of loop A, loop B, loop C, loop D and loop E, or a fragment thereof.

31. The composition of claim 30, wherein the exposed loop of HA is selected from the group consisting of loop A and loop B, or a fragment thereof.

32. The composition of claim 31, wherein the fragment of loop A is an antigenic epitope comprising an amino acid sequence selected from the group consisting of SEQ ID NO: 75, SEQ ID NO: 77 and SEQ ID NO: 79, or a variant thereof.

33. The composition of claim 32, wherein the variant comprises an amino acid sequence selected from the group consisting of SEQ ID NO: 1; SEQ ID NO:2; SEQ ID NO:3; SEQ ID NO:4; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:19; SEQ ID NO:20; SEQ ID NO:22; SEQ ID NO:23; SEQ ID NO:47; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59 and SEQ ID NO:60.

34. The composition of claim 32, wherein the variant has at least 30% sequence identity to the amino acid sequence selected from the group consisting of SEQ ID NO: 75, SEQ ID NO: 77 and SEQ ID NO: 79.

35. The composition of claim 31, wherein the fragment of loop B is an antigenic epitope comprising an amino acid sequence selected from the group consisting of SEQ ID NO: 76, SEQ ID NO: 78 and SEQ ID NO: 80, or a variant thereof.

36. The composition of claim 35, wherein the variant comprises an amino acid sequence selected from the group consisting of SEQ ID NO:25; SEQ ID NO:26; SEQ ID NO:27; SEQ ID NO:30; SEQ ID NO:34; SEQ ID NO:35; SEQ ID NO:36; SEQ ID NO:42; SEQ ID NO:43; SEQ ID NO:44; SEQ ID NO:45; SEQ ID NO:46; SEQ ID NO:61; SEQ ID NO:65; SEQ ID NO:66; SEQ ID NO:67; SEQ ID NO:69; SEQ ID NO:70; SEQ ID NO:71; SEQ ID NO:72; SEQ ID NO:73 and SEQ ID NO:74.

37. The composition of claim 35, wherein the variant has at least 30% sequence identity to the amino acid sequence selected from the group consisting of SEQ ID NO: 76, SEQ ID NO: 78 and SEQ ID NO: 80.

38. The composition of claim 23, wherein the said virus protein other than murine polyomavirus VP1, or a fragment thereof, is a single protein or a plurality of proteins.

39. The method of claim 20, wherein the one or more exposed loops of said murine polyomavirus VP1 amino acid sequence comprise an insertion site selected from the group consisting of site 1, site 3 and site 4.

40. The method of claim 20, wherein the insertion site is selected from the group consisting of site 1 and site 4.

41. The method of claim 39, wherein the virus protein other than murine polyomavirus VP1 or a fragment thereof, is an influenza virus protein.

42. The method of claim 41, wherein the influenza virus protein is selected from the group consisting of HA, NP, NA, M2 and M1.

43. The method of claim 42, wherein the influenza virus protein is selected from the group consisting of HA and M2.

44. The method of claim 39, wherein the virus protein other than murine polyomavirus VP1 is an exposed loop of HA selected from the group consisting of loop A, loop B, loop C, loop D and loop E, or a fragment thereof.

45. The method of claim 44, wherein the exposed loop of HA is selected from the group consisting of loop A and loop B, or a fragment thereof.

46. The method of claim 45, wherein the fragment of loop A is an antigenic epitope comprising an amino acid sequence selected from the group consisting of SEQ ID NO: 75, SEQ ID NO: 77 and SEQ ID NO: 79, or a variant thereof.

47. The method of claim 46, wherein the variant comprises an amino acid sequence selected from the group consisting of SEQ ID NO: 1; SEQ ID NO:2; SEQ ID NO:3; SEQ ID NO:4; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:19; SEQ ID NO:20; SEQ ID NO:22; SEQ ID NO:23; SEQ ID NO:47; SEQ ID NO:51; SEQ ID NO:52; SEQ ID NO:53; SEQ ID NO:54; SEQ ID NO:55; SEQ ID NO:56; SEQ ID NO:57; SEQ ID NO:58; SEQ ID NO:59 and SEQ ID NO:60.

48. The method of claim 46, wherein the variant has at least 30% sequence identity to the amino acid sequence selected from the group consisting of SEQ ID NO: 75, SEQ ID NO: 77 and SEQ ID NO: 79.

49. The method of claim 45, wherein the fragment of loop B is an antigenic epitope comprising an amino acid sequence selected from the group consisting of SEQ ID NO: 76, SEQ ID NO: 78 and SEQ ID NO: 80, or a variant thereof.

50. The method of claim 49, wherein the variant comprises an amino acid sequence selected from the group consisting of SEQ ID NO:25; SEQ ID NO:26; SEQ ID NO:27; SEQ ID NO:30; SEQ ID NO:34; SEQ ID NO:35; SEQ ID NO:36; SEQ ID NO:42; SEQ ID NO:43; SEQ ID NO:44; SEQ ID NO:45; SEQ ID NO:46; SEQ ID NO:61; SEQ ID NO:65; SEQ ID NO:66; SEQ ID NO:67; SEQ ID NO:69; SEQ ID NO:70; SEQ ID NO:71; SEQ ID NO:72; SEQ ID NO:73 and SEQ ID NO:74.

51. The method of claim 49, wherein the variant has at least 30% sequence identity to the amino acid sequence selected from the group consisting of SEQ ID NO: 76, SEQ ID NO: 78 and SEQ ID NO: 80.

52. The method of claim 39, wherein the virus protein other than murine polyomavirus VP1, or a fragment thereof, is a single protein or a plurality of proteins.

* * * * *